(12) United States Patent
Thomas et al.

(10) Patent No.: US 11,000,406 B2
(45) Date of Patent: May 11, 2021

(54) HEATING DEVICES

(71) Applicant: Relief Technologies, Inc., San Francisco, CA (US)

(72) Inventors: Jonathan Moulton Thomas, San Francisco, CA (US); Brian James Krieger, San Francisco, CA (US); Richard Thomas Caligaris, Los Altos, CA (US); Elizabeth Ann Miracle, San Francisco, CA (US); Grace Hina Lee, San Francisco, CA (US)

(73) Assignee: Relief Technologies, Inc., San Francisco, CA (US)

( * ) Notice: Subject to any disclaimer, the term of this patent is extended or adjusted under 35 U.S.C. 154(b) by 445 days.

(21) Appl. No.: 15/863,296

(22) Filed: Jan. 5, 2018

(65) Prior Publication Data
US 2018/0193185 A1 Jul. 12, 2018

Related U.S. Application Data

(60) Provisional application No. 62/443,041, filed on Jan. 6, 2017.

(51) Int. Cl.
*A61F 7/00* (2006.01)
*H05B 3/34* (2006.01)
(Continued)

(52) U.S. Cl.
CPC ............ *A61F 7/007* (2013.01); *A61F 7/02* (2013.01); *H05B 1/025* (2013.01); *H05B 3/34* (2013.01);
(Continued)

(58) Field of Classification Search
CPC .... A61F 7/007; A61F 7/02; A61F 2007/0228; A61F 2007/0071; A61F 2007/0086;
(Continued)

(56) References Cited

U.S. PATENT DOCUMENTS 3,634,655 A * 1/1972 Jordan ............... H05B 3/342
219/527
4,243,041 A * 1/1981 Paul ..................... A61F 7/10
351/124
(Continued)

OTHER PUBLICATIONS

Brookstone Shiatsu Neck and Back Massager with Heat.pdf—copyright 2016, 2 pages.
(Continued)

*Primary Examiner* — Vishal Pancholi
*Assistant Examiner* — Bob Zadeh
(74) *Attorney, Agent, or Firm* — RMCK Law Group, PLC

(57) ABSTRACT

A heating device includes a heating unit and device electronics. The heating unit is configured to deliver heat to a user's body. The heating unit includes a substrate and a heating element supported by the substrate. The device electronics are coupled to the heating element and are configured to store a first heating profile that includes data indicating how power should be delivered to the heating element over a first period of time. The device electronics are configured to deliver power to the heating element according to the first heating profile. The device electronics are configured to wirelessly receive a second heating profile from an external computing device. The second heating profile includes data indicating how power should be delivered to the heating element over a second period of time. The device electronics are configured to deliver power to the heating element according to the second heating profile.

30 Claims, 38 Drawing Sheets

(51) Int. Cl.
*H05B 1/02* (2006.01)
*A61F 7/02* (2006.01)

(52) U.S. Cl.
CPC . *A61F 2007/003* (2013.01); *A61F 2007/0022* (2013.01); *A61F 2007/0023* (2013.01); *A61F 2007/0027* (2013.01); *A61F 2007/0071* (2013.01); *A61F 2007/0078* (2013.01); *A61F 2007/0086* (2013.01); *A61F 2007/0093* (2013.01); *A61F 2007/0096* (2013.01); *A61F 2007/0228* (2013.01); *A61F 2007/0236* (2013.01); *H05B 2203/003* (2013.01); *H05B 2203/013* (2013.01)

(58) Field of Classification Search
CPC ...... A61F 2007/0022; A61F 2007/0023; A61F 2007/0093; A61F 2007/003; A61F 2007/0027; A61F 2007/0078; A61F 2007/0096; A61F 2007/0236; H05B 1/025; H05B 3/34; H05B 2203/003; H05B 2203/013
See application file for complete search history.

(56) References Cited

U.S. PATENT DOCUMENTS

| | | | | |
|---|---|---|---|---|
| 6,068,606 | A * | 5/2000 | Castel | A61F 5/028 128/876 |
| 9,795,502 | B1 * | 10/2017 | Kopes | A61F 7/007 |
| 2002/0190059 | A1 * | 12/2002 | Lam | H05B 3/34 219/528 |
| 2006/0060576 | A1 * | 3/2006 | Haas | A41D 13/0051 219/543 |
| 2006/0195168 | A1 * | 8/2006 | Dunbar | A61M 35/00 607/108 |
| 2007/0016271 | A1 * | 1/2007 | Hammond | A61F 7/007 607/96 |
| 2011/0220634 | A1 * | 9/2011 | Yeh | A43B 3/0005 219/482 |
| 2013/0036549 | A1 * | 2/2013 | McKlarney | A47C 21/044 5/413 R |
| 2014/0209594 | A1 * | 7/2014 | Besner | A61N 5/06 219/217 |
| 2014/0350645 | A1 * | 11/2014 | Diller | A61F 7/08 607/96 |
| 2015/0083705 | A1 * | 3/2015 | Cronn | H05B 3/347 219/211 |
| 2016/0178251 | A1 * | 6/2016 | Johnson | A41D 27/06 62/3.5 |
| 2016/0374411 | A1 * | 12/2016 | Brooks | A41D 13/0053 165/104.21 |
| 2017/0028196 | A1 * | 2/2017 | Stopperan | A61N 1/36021 |
| 2017/0258629 | A1 * | 9/2017 | Awasthi | A61F 7/007 |
| 2020/0008973 | A1 * | 1/2020 | Dunbar | A61F 7/007 |

OTHER PUBLICATIONS

Palm NRG—Cordless heat pads—accessed on Jan. 2, 2018, https://web.archive.org/web/20160311234727/https://shop.palmnrg.net/products/cordless-heat-pads. The site is dated Mar. 11, 2016, 3 pages.
SoftHeat Soothing Therapy Mobile PowerWrap Manual.pdf—copyright 2013, 24 pages.
Sunbeam Heating Pad Instruction Manual—copyright 2008, 2 pages.
Versatile Body Wrap.pdf—the website http://qfiber.com/products/versatile-body-wrap.php was accessed Jan. 2, 2018 and is copyright 2015, 1 page.

* cited by examiner

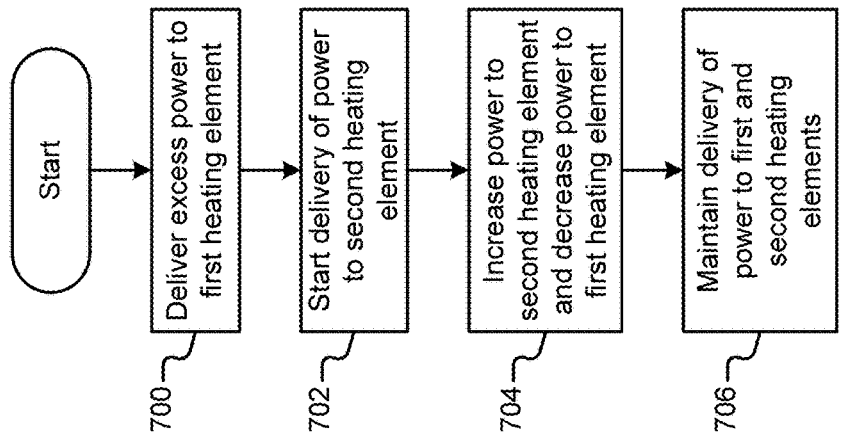
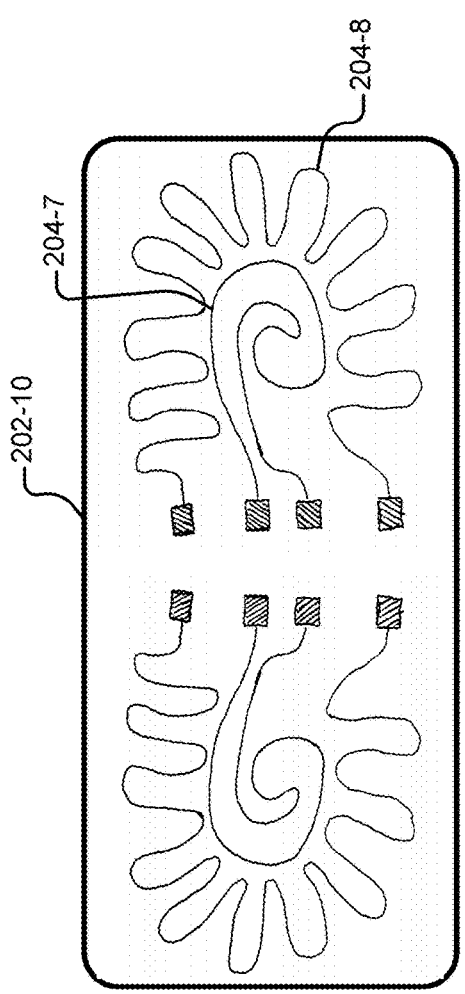
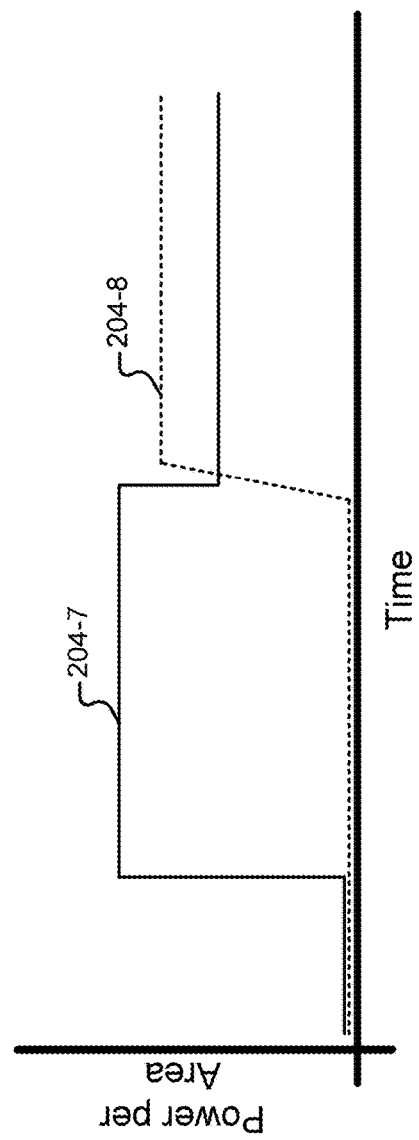
FIG. 7A
FIG. 7B
FIG. 7C

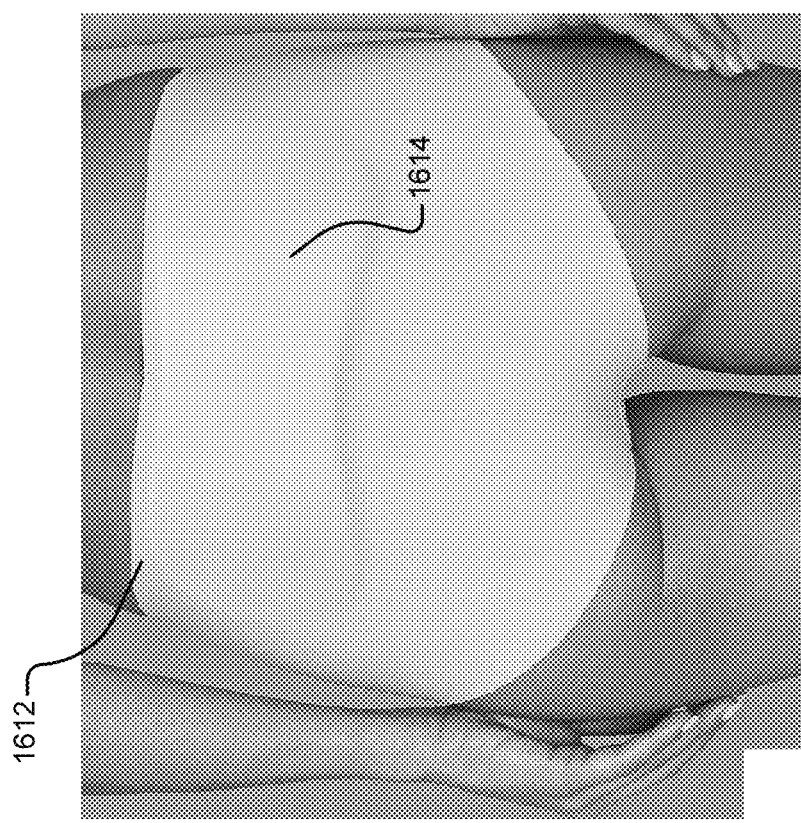

HEATING DEVICES

CROSS-REFERENCE TO RELATED APPLICATIONS

This application claims the benefit of U.S. Provisional Application No. 62/443,041, filed on Jan. 6, 2017. The disclosure of the above application is incorporated herein by reference in its entirety.

FIELD

The present disclosure relates to heating devices that provide heat to a user's body.

BACKGROUND

Heating therapy can be used to provide relief/rehabilitation for a variety of ailments, such as muscle ailments (e.g., soreness, tightness, or spasms), joint ailments (e.g., stiffness or arthritis), or other tissue ailments (e.g., tissue injuries). Heating therapy can be applied in a variety of manners, such as via direct contact with the skin (e.g., a hot cloth, pad, or hot water bath) or via infrared radiation. Heat therapy may increase tissue temperature, which may produce vasodilation that causes increased blood flow to affected areas, thereby increasing the supply of oxygen and nutrients to the affected areas. The therapeutic effects of heat may include a reduction in pain, stiffness, and inflammation in the affected areas.

SUMMARY

In one example, the present disclosure is directed to a heating device comprising a heating unit and device electronics. The heating unit is configured to deliver heat to a user's body. The heating unit comprises a substrate and a heating element supported by the substrate. The device electronics are coupled to the heating element. The device electronics are configured to store a first heating profile that includes data indicating how power should be delivered to the heating element over a first period of time. The device electronics are configured to deliver power to the heating element according to the first heating profile. The device electronics are configured to wirelessly receive a second heating profile from an external computing device. The second heating profile includes data indicating how power should be delivered to the heating element over a second period of time. The device electronics are configured to deliver power to the heating element according to the second heating profile.

In another example, the present disclosure is directed to a heating device comprising a first heating element, a second heating element, and device electronics. The first heating element is configured to deliver heat to a first portion of a user's body. The second heating element is configured to deliver heat to a second portion of the user's body. The device electronics are coupled to the first and second heating elements and configured to wirelessly communicate with an external computing device. The device electronics are configured to wirelessly receive a first user-input instruction from the external computing device, the first user-input instruction indicating a first amount of power to deliver to each of the first and second heating elements. The device electronics are configured to deliver power to the first and second heating elements based on the first user-input instruction. The device electronics are configured to wirelessly receive a second user-input instruction from the external computing device, the second user-input instruction indicating a second amount of power to deliver to the first heating element. The device electronics are configured to modify the delivery of power to the first heating element based on the second user-input instruction.

BRIEF DESCRIPTION OF THE DRAWINGS

The present disclosure will become more fully understood from the detailed description and the accompanying drawings.

FIGS. 7A-7C are directed to techniques for immediately heating a user.
FIGS. 16A-16E illustrate example sleeves and garments that hold heating devices.

In the drawings, reference numbers may be reused to identify similar and/or identical elements.

DETAILED DESCRIPTION

Figure 1A:
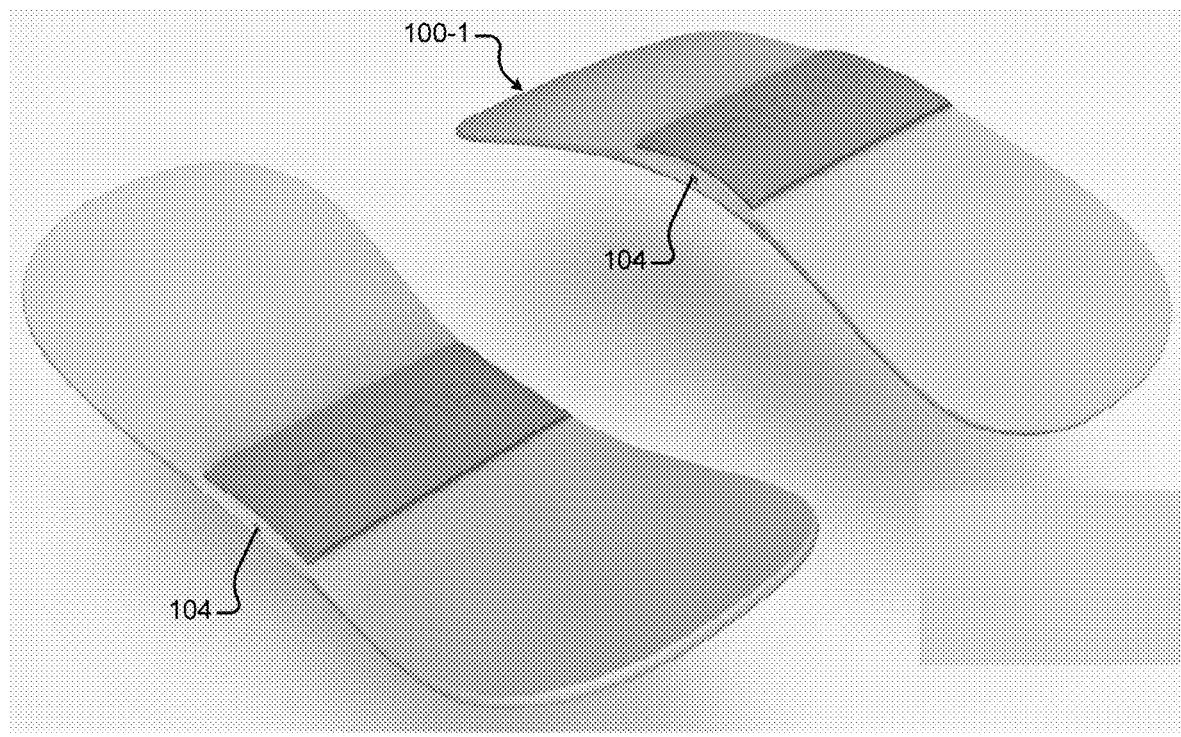
FIGS. 1A-1C illustrate a first example heating device.
Figure 1B:
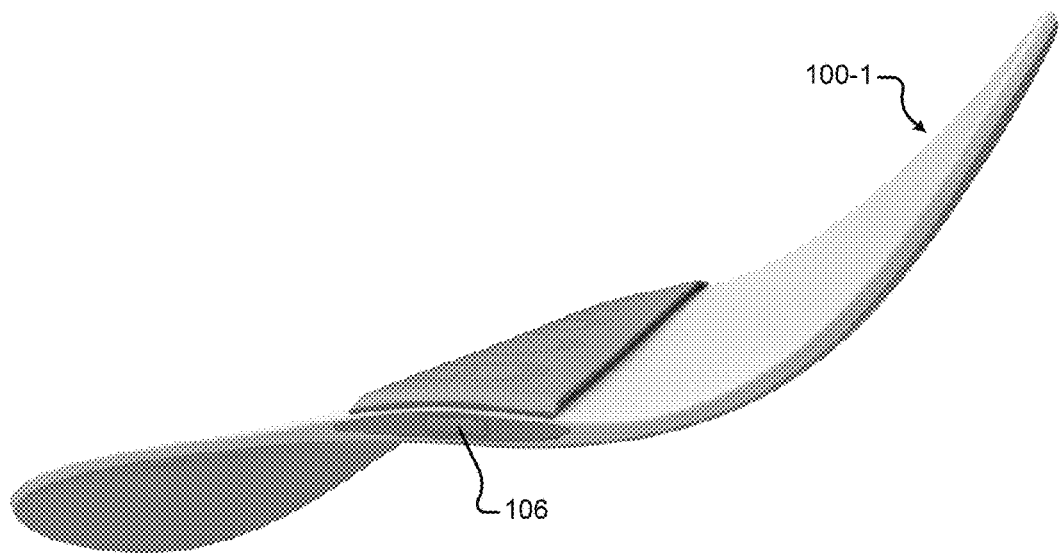

A heating device of the present disclosure (e.g., FIG. 1A) may be used to provide relief for a variety of different conditions including, but not limited to, muscle soreness, headaches, joint pain, and arthritis. The heating device may also be used to provide relief for pelvic pain conditions, such as chronic pelvic pain, dyspareunia, vulvodynia, endometriosis, and dysmenorrhea (menstrual pain). A variety of example heating devices 100-1, 100-2, . . . , 100-6 are illustrated and described herein (e.g., FIGS. 1A-1C and FIGS. 10A-15). A heating device 100 may generally refer to any of the example heating devices.

A heating device 100 (e.g., a heating pad) includes one or more heating units (e.g., heating unit 202-1 of FIG. 2B) that can generate heat for application to one or more areas of a user's body. The heating device 100 can include a device package (e.g., encapsulation 1006 of FIG. 10B) that houses the one or more heating units. A user can control the heating device manually. For example, the heating device 100 may include user input devices (e.g., manual controls) and/or be controlled via an external computing device 102, such as a user's phone (e.g., see FIG. 1C). In one specific example, the heating device 100-1 of FIG. 1B includes a user input button 106. The heating device 100 may also automatically run heating device profiles (e.g., FIGS. 5A-5E) that include data indicating how the heating device 100 should operate over time.

A heating unit can include a heating element and a substrate. Example heating units 202-1, 202-2, . . . , 202-13 (generally "heating unit 202") are illustrated herein (e.g., FIGS. 2C-2F). Example heating elements 204-1, 204-2, . . . , 204-8 (generally "heating element 204") are illustrated herein (e.g., FIGS. 2B-2F). Example substrates 200-1, 200-2, 200-3, 200-4 (generally "substrate 200") are illustrated herein (e.g., FIG. 2A).

The heating element 204 can generate heat that is applied to a user's body (e.g., via resistive heating). For example, the heating element 204 may include a metallic wire that generates heat when power is delivered to the heating element 204. The substrate 200 can provide support to the heating element 204 (e.g., to maintain shape) so that the heating element 204 can be positioned near the user's body. For example, the heating element 204 can be attached to the substrate 200 and/or formed on the substrate 200 (e.g., etched on the substrate). The substrate 200 can be composed of a flexible material and/or a rigid material.

The heating device 100 includes device electronics (e.g., device electronics 300 in FIGS. 3A-3D) that control the amount of heat generated by the heating elements 204. For example, the device electronics may control heat by controlling power (e.g., current or voltage) delivered to the heating elements 204. In some implementations, the heating device 100 may include one or more sensors (e.g., temperature, orientation, motion, and/or pressure sensors). In these implementations, the device electronics may control the amount of heat generated by the heating elements 204 based on data acquired from the one or more sensors. In some implementations, the heating device 100 may include a battery, such as battery 302 in FIGS. 3B-3D, FIG. 10B, and FIG. 13C. In these implementations, the device electronics can manage charging/discharging of the battery and control heating based on a variety of conditions, such as a state of charge of the battery, the currently running heating device profile, and/or a target device run time indicated by the user.

In some implementations, the heating device 100 may include user interface devices that allow the user to interact with the heating device 100. For example, the heating device 100 may include buttons, switches, touch sensitive controls, and/or a display that allow the user to control/monitor the amount of heat being generated by the heating device 100. The device electronics may communicate with the user interface devices in order to control heating of the heating elements 204 and provide output to the user. In some implementations, the device electronics may include electronics that can communicate with an external wired/wireless computing device 102, such as a user's cell phone (e.g., see FIG. 1C). In these implementations, the user may control/monitor the heat being generated by the heating device 100 using the external computing device 102. The external computing device 102 may be referred to herein as a "user device 102."

The heating device 100 can be powered in a variety of different ways. In some implementations, the heating device 100 can be configured to receive a battery 302 (e.g., rechargeable/non-rechargeable battery) from the user. The battery 302 may be removable by hand and/or fixed within the heating device 100 (e.g., accessible using tools). Additionally, or alternatively, the heating device 100 can be plugged into an external power source (e.g., via a power input port 104) that may power the heating device and/or charge the battery 302.

The arrangement of the one or more heating elements 204 may create one or more heating zones. A heating zone refers to an area of the heating device 100 in which heat is delivered to the user. A user may control the heat generated in a heating zone by controlling power delivered to the heating element(s) 204 making up the heating zone. In some cases, heating zones can be surrounded by cooler areas of the heating device 100 (e.g., areas not including heating elements 204). Put another way, if a heating device 100 has multiple heating zones, the heating zones can be separated from one another. In other cases, the heating zones may not be separated, but instead, some of the heating zones may merge together such that the two heating zones are bridged by a heated area instead of a cooler area.

The heating device 100 can be configured to operate in one or more of three modes, which may be referred to herein as a manual mode, an automatic mode, or a mixed mode. The heating device 100 can operate in a manual mode in which the heating device is configured to generate heat in response to a user's manual input. For example, while operating in the manual mode, a user can control heating using manual controls on the heating device 100 and/or using the user device 102. In a more specific example, the user can incrementally increase/decrease heating in different heating zones using manual controls and/or graphical controls rendered on a graphical user interface (GUI) of the user device 102. In the manual mode, the user may control one or more of the heating zones. If the heating device 100 has multiple heating zones, the user may manually control the heating zones independently or together.

The heating device 100 can operate in an automatic mode in which the heating device 100 generates heat according to a heating profile, or sequence of profiles, loaded on the heating device 100. The heating profile can include data indicating how the heating device 100 should heat the one or more heating zones. For example, if a heating device 100 includes a single heating element 204, the heating profile may include data that indicates how to heat the heating element 204. In this example, the heating profile may include data indicating the amount of power (e.g., voltage or current) to be delivered to the heating element 204 over a period of time. FIGS. 5A-5E illustrate example heating profiles that may be used by the heating device 100. In heating devices 100 including multiple heating elements 204, a heating profile can include data indicating the amount of power (e.g., voltage or current) to be delivered to each of the multiple heating elements 204. A heating profile may also indicate how the heating device 100 should operate in response to data acquired from one or more sensors included on the heating device 100. For example, the heating profile may indicate whether to increase/decrease the delivery of power based on a detected temperature.

The heating device 100 can store one or more heating profiles. In some implementations, the heating profiles may be stored permanently in memory (e.g., in a ROM), and the user can select from the heating profiles using manual controls and/or a GUI. In some implementations, the user can load different heating profiles onto the heating device 100 (e.g., from the user device 102) and then select from the loaded heating profiles.

The heating device 100 may operate in a mixed mode during which the user can modify/update a heating profile while the heating device 100 is controlling heat according to the heating profile. Modification of the heating profile may refer to a situation where any portion of the heating profile is changed by the user. The user can modify the heating profile in a variety of different ways. For example, the user may modify a heating profile by: 1) adjusting the amount of heat generated (e.g., the voltage or current) by one or more heating elements 204, 2) adjusting the frequency of the heat generated (e.g., frequency of heating pulses) in one or more heating elements 204, 3) adjusting timing delays between the one or more heating elements 204, and/or 4) loading a new heating profile for one or more of the heating elements 204. In some mixed mode implementations, the heating device 100 may memorize a heating profile generated by the user. For example, the user may modify the amplitude of heat generated by the heating device 100 (e.g., using the user device 102 and/or manual controls) in one or more heating elements 204 and the heating device 100 may store a heating profile that corresponds to the user's heating pattern.

In some implementations, the heating device 100 can be configured to operate in any of the three modes. For example, the heating device 100 can be configured to allow the user to select the mode (e.g., using a button or GUI). In some implementations, the heating device 100 can have more limited functionality. For example, the heating device 100 may be configured to operate in one or two of the modes, but not the other mode(s). For example, the heating device 100 may be configured to operate in the manual mode, but not the automatic or mixed modes.

The user can generate new heating profiles in a variety of different ways. In some implementations, the user can create a new heating profile using a computing device other than the heating device 100, such as a cell phone or laptop computer. The user can then load the newly created heating profile onto the heating device 100 (e.g., using the user device 102). In some implementations, the user can create a new heating profile from scratch (e.g., without using another existing heating profile). In other implementations, the user can create a new heating profile by modifying an existing heating profile. For example, the user can modify an existing heating profile running on the heating device 100 (e.g., in the mixed mode) and then save the modified heating profile as a new heating profile. As another example, the user may load an existing heating profile on an external computing device, modify the loaded heating profile, and then save the modified heating profile on the heating device 100 as a new heating profile. The user may also use the heating device 100 (e.g., a user input device such as a touchscreen) to generate new heating profiles and/or modify existing heating profiles.

Figure 4:
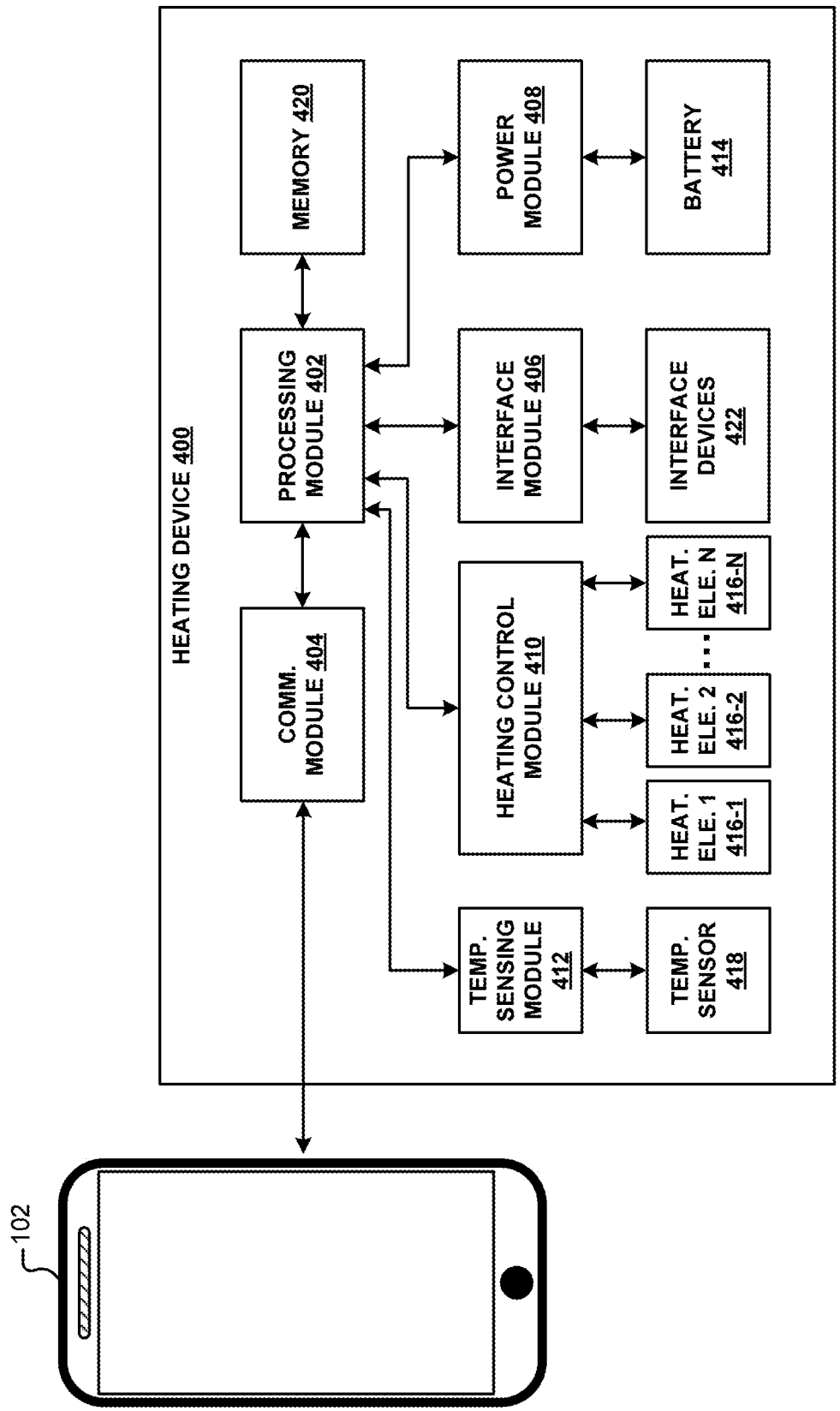
FIG. 4 is a functional block diagram of an example heating device.

The heating device 100 can store one or more heating profiles in memory (e.g., memory 420 of FIG. 4). The heating device 100 can update the stored heating profiles over time. For example, the heating device 100 can delete stored heating profiles and add additional heating profiles to memory. The heating device 100 can acquire heating profiles from different sources. For example, if the heating device 100 includes wired/wireless communication technology (e.g., WiFi, Bluetooth, etc.), the heating device 100 can retrieve heating profiles via the internet (e.g., from the remote server 802 of FIG. 8) and/or the user device 102.

In some implementations, the heating device 100 can include one or more sensors. The sensors may include, but are not limited to, a temperature sensor (e.g., FIG. 4), a motion sensor, an orientation sensor, and a pressure/force sensor. A temperature sensor may indicate the temperature of an area of the heating device 100 in the location of the temperature sensor. Example temperature sensors may include, but are not limited to, thermocouples, thermistors, resistance temperature detectors, and semiconductor based temperature sensors. A motion sensor may generate a motion signal that indicates an amount of motion of the heating device 100 (e.g., rotation/translation). Example motion sensors may include, but are not limited to, linear or angular accelerometers, gyroscopes, magnetometers, or integrated inertial measurement units. An orientation sensor may generate an orientation signal that indicates the orientation of the heating device 100 (e.g., indicating a user's posture). Example orientation sensors may include, but are not limited to, linear or angular accelerometers, gyroscopes, magnetometers, or integrated inertial measurement units. A pressure/force sensor may indicate an amount of pressure/force in an area of the heating device 100.

One or more sensors may be located on or within the substrate 200. The temperature sensors may be positioned near heating elements 204 so that the temperature indicated by the temperature sensors reflect the temperature near one or more heating elements 204. Integrating the temperature sensors onto the substrate 200 may be beneficial in some implementations. For example, integrating a temperature sensor onto the substrate (e.g., 310 in FIG. 3C) may provide for more accurate temperature sensing at the location where heat is being delivered to the user. Additionally, or alternatively, the temperature sensors may be located farther from the heating elements, such as along with the device electronics on the substrate or off the substrate. In some implementations, a temperature sensor can be placed in contact with a user's body. For example, a temperature sensor may be embedded in the substrate or device package in contact with the user's body. As another example, a temperature sensor may be attached externally to the heating device via a wire and sandwiched between the user and the heating device during use.

The orientation/motion sensors may also be included on the substrate 200 and/or along with the device electronics 300 in order to detect the orientation/motion of the heating device 100 (i.e., the user). In some implementations, an orientation/motion sensor may be included on the user device 102 (e.g., a cell phone) which may be carried by the user (e.g., in their hand or pocket) and, therefore, detect the orientation/motion of the user. In these implementations, the user device 102 may communicate with the heating device 100 so that the heating device 100 can modify heating based on the user's orientation/motion as determined by the user device 102.

The device electronics 300 may control heating based on data acquired from the sensors. For example, with respect to a temperature sensor, the device electronics 300 may control the heating device 100 to maintain a target temperature. As another example, the device electronics 300 may control the heating device 100 to maintain a temperature that is less than a threshold temperature (e.g., a maximum user comfort temperature and/or a maximum heating device temperature). With respect to the orientation/motion sensors, the device electronics 300 may change heating profiles/intensity based on a user's orientation and/or amount of motion. In a specific example, if a motion sensor detects changes indicative of user movement, the device electronics 300 may be configured to generate a greater amount of heat to alleviate discomfort resulting from movement. In a different specific example, the device electronics 300 may be configured to generate a greater amount of heat when a user is seated (e.g., as detected by the orientation/motion sensors) in order to alleviate discomfort resulting from sitting for long periods of time.

The heating device 100 can determine a user status based on data acquired from one or more sensors. The heating device 100 may load different heating profiles corresponding to the different user statuses. For example, the heating device 100 may include a seated heating profile, a standing heating profile, a walking heating profile, and a running heating profile that may be loaded in response to the heating device 100 detecting a corresponding user status. In a specific example, if the heating device 100 determines that a user is seated (e.g., upright posture with little motion), the heating device 100 may load a seated heating profile. At a later time, if the heating device 100 detects that a user transitions from a seated position to walking, the heating device 100 may load the walking heating profile. The user may configure the different heating profiles for different statuses. In some cases, the user may configure the heating device 100 to cease heating during some user activities and provide heating during other activities. For example, the heating device 100 may be configured to remain in a standby state (e.g., where heating is turned off) when the user is seated, and then provide heating when the user is standing. A user may configure the heating device 100 in such a manner when the user feels little or no discomfort when seated, but then feels discomfort when standing. Additional user statuses can include user posture, such as whether the user is upright or leaning to one side. In some implementations, instead of loading a different profile for a different status, the heating device 100 can be configured to adjust parameters of the heating profile, such as the amplitude of the heating, the frequency of heating pulses, or the phase difference between different heating zones.

The heating device 100 can be configured to operate with varying degrees of autonomy with respect to a user device 102. In some implementations, the heating device 100 can be configured to operate without any communication with the user device 102. For example, the heating device 100 may not include wired/wireless communication technology for communicating with a user device 102. In other implementations, the heating device 100 may be configured to communicate with the user device 102, but operate autonomously without further communication with the user device 102. For example, the heating device 100 may be configured to receive heating profiles from the user device 102 and then operate according to the heating profiles without additional communication with the user device 102. In other implementations, the heating device 100 may be configured to make intermittent communication with the user device 102 and operate according to instructions and/or heating profiles received from the user device 102. In these examples, the heating device 100 may intermittently communicate with the user device 102 to receive instructions, such as instructions for increasing/decreasing the amount of heat to be generated. Accordingly, in some cases, the user device 102 can adjust operation of the heating device 100 over time while the heating device 100 is operating (e.g., in the automatic and/or mixed mode).

In some examples, the user device 102 may generate instructions based on user input received on the user device 102, such as user input received from a GUI in FIGS. 9A-9K. The user device 102 may then wirelessly transmit the user-input instructions to the heating device 100. The heating device 100 may control the amount of power to the heating elements 204 based on the received user-input instructions (e.g., to increase/decrease heating).

The user device 102 and heating device 100 can communicate using a variety of different communication protocols. In some implementations, communication between the user device 102 and the heating device 100 may involve pairing followed by periodic polling/updating of data. The connection between the user device 102 and the heating device 100 may be continuous (e.g., streaming data and/or control). Alternatively, the connection between the user device 102 and the heating device 100 may be intermittent (e.g. downloading of a profile and/or instructions).

Figure 8:
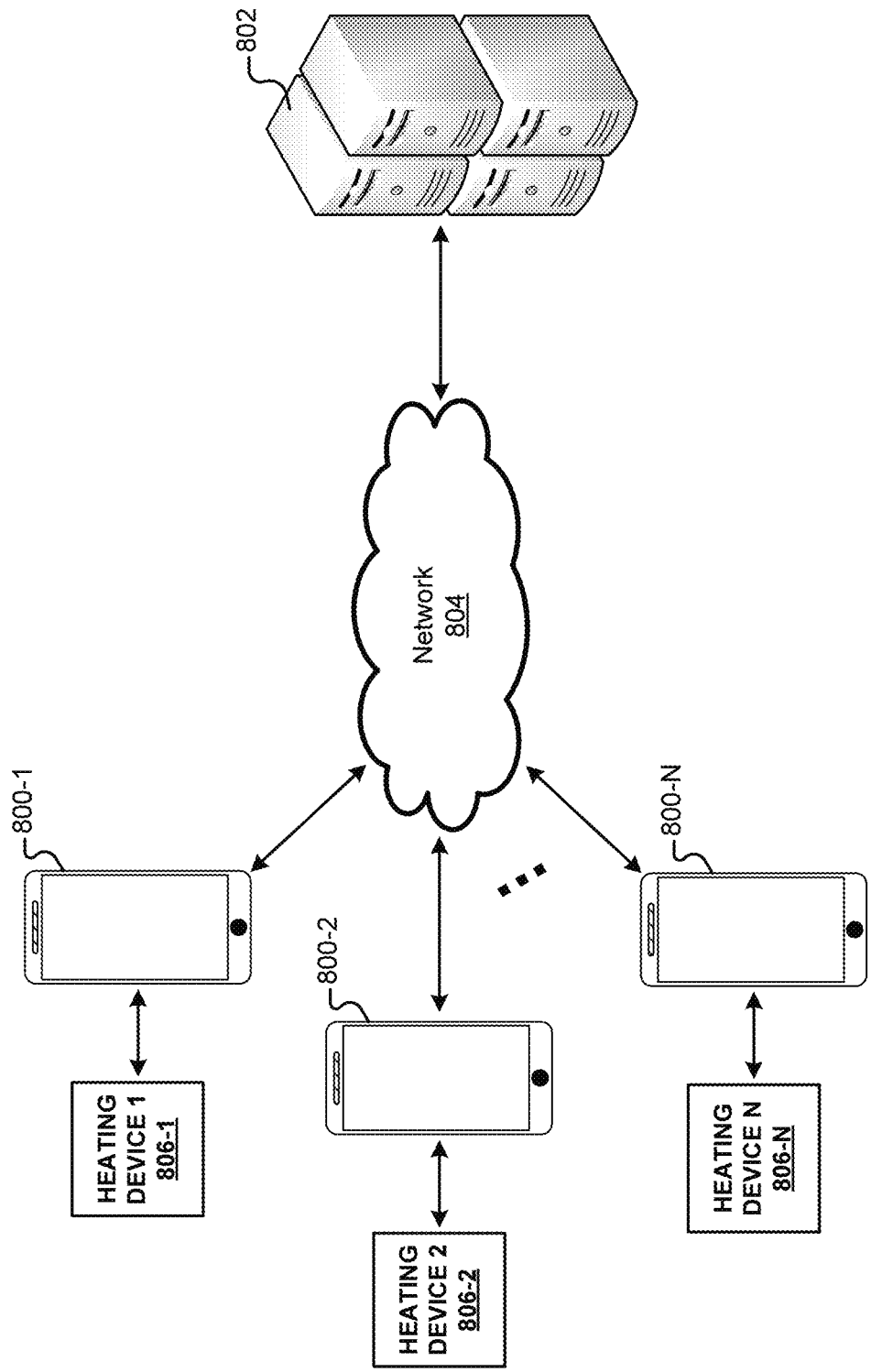
FIG. 8 illustrates communication between a plurality of heating devices and a remote server.

FIGS. 1A-16E illustrate features of example heating devices 100. FIGS. 1A-1C and 10A-15 illustrate different example heating device form factors. FIGS. 2A-2F illustrate example heating units. FIGS. 3A-3D illustrate example heating units connected to other components, such as device electronics, a battery, and a sensor. FIG. 4 is an example functional block diagram of a heating device. FIGS. 5A-5E illustrate example heating profiles that may run on a heating device 100. FIGS. 6A-6C illustrate example methods describing different heating device modes of operation. FIGS. 7A-7C are directed to providing immediate heating. FIG. 8 illustrates a plurality of heating devices in communication with a remote server via a plurality of user devices. FIGS. 9A-9K illustrate example GUIs on a user device that the user may interact with in order to control/monitor the heating device. FIGS. 16A-16E illustrate example sleeves and garments that may hold the heating device.

Figure 2A:
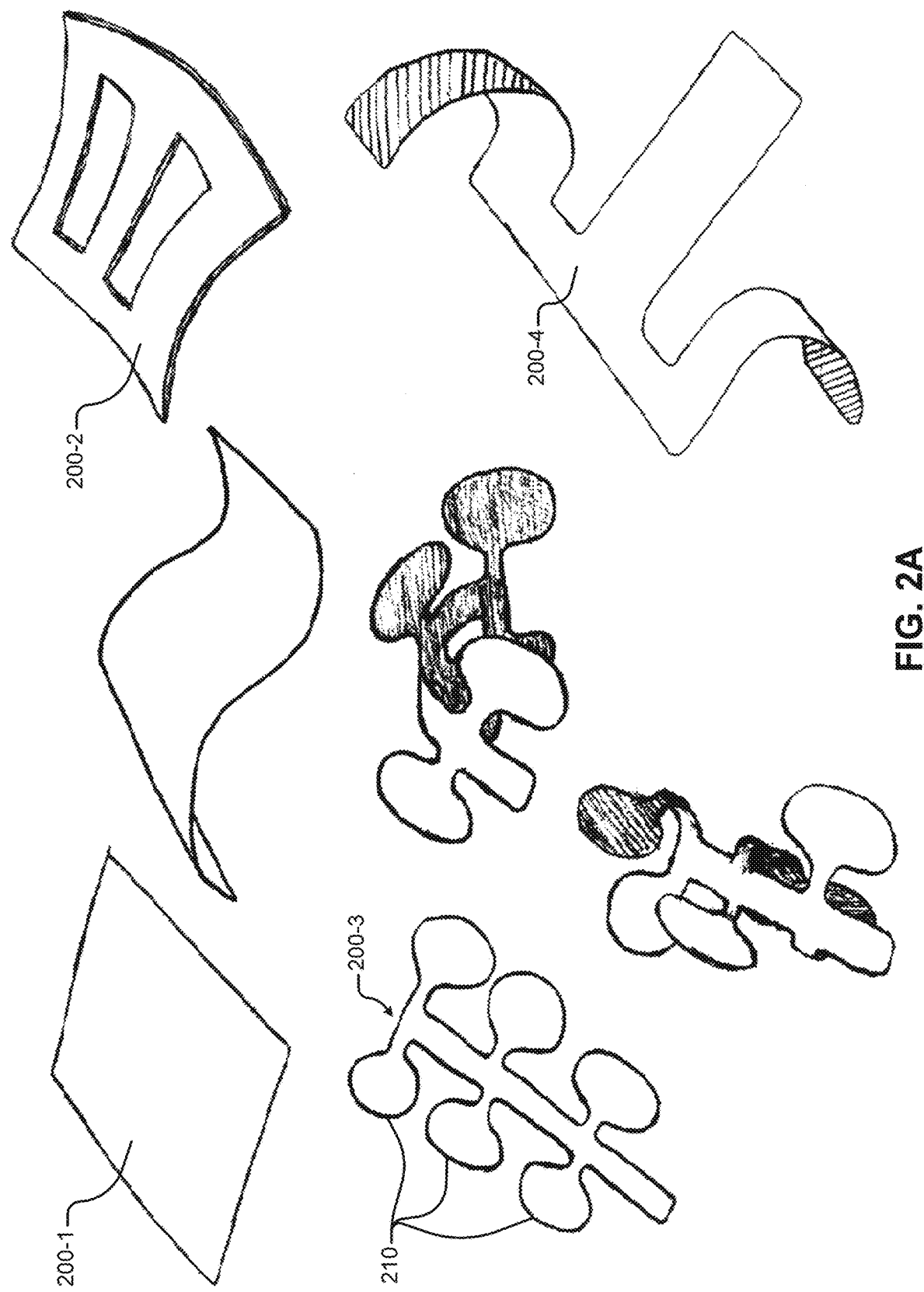
FIGS. 2A-2F illustrate example heating units.

FIGS. 2A-2F illustrate a variety of different substrates 200 having different shapes and arrangements of heating elements 204. FIG. 2A illustrates a variety of different substrate shapes and features, such as rectangular substrates 200-1, a substrate including cutouts 200-2, substrates including protrusions 200-3 (e.g., lobes), and a substrate 200-4 including strips. Although not illustrated, the substrates 200 of FIG. 2A may include heating elements 204 (e.g., in the substrate or on one surface of the substrate).

A substrate 200 may be flexible or rigid. In some implementations, the entire substrate may be flexible. Although some of the substrates 200 in FIGS. 2A-2F are illustrated as being flexed, any of the substrates in FIGS. 2A-2F may be flexible. Flexibility may allow the substrate to conform to the user's body during use. In other implementations, the entire substrate may be rigid. In still other implementations, the substrate may include portions that are rigid and portions that are flexible. The entire substrate may be formed from the same material in some cases. In other cases, the substrate may include portions that are formed from different materials. A flexible portion of substrate may be made rigid by reinforcing a portion of the substrate with additional material and/or different material. FIGS. 3A-3B illustrate a substrate that is partially rigid and partially flexible. The rigid portion of the substrate in FIGS. 3A-3B includes device electronics 300.

A substrate 200 can be formed from any material that is tolerant to the levels of heat generated by the heating element(s) 204 and other processing steps used to fabricate the heating unit 202 (e.g., oven reflow or wave flow soldering). Example materials may include, but are not limited to, polyester, polyimide, and silicone. In some implementations, the substrate may include a single layer of material. In other implementations, the substrate may include multiple layers of material that are bonded to one another.

A single substrate 200 can include one or more heating elements 204. The combination of substrate 200 and one or more heating elements 204 may be referred to herein as a "heating unit 202." A heating device 100 may include one or more heating units 202. For example, a heating device 100 may include a heating device package (e.g., FIGS. 1A, 10B, and 13C) that includes one or more heating units 202.

In some implementations, a heating element 204 may be formed from an electrical conductor that can provide resistive heating. The heating element 204 may be formed from a metallic material. Example metallic materials may include, but are not limited to, nichrome, FeCrAl alloy, cupronickel, and platinum. In implementations in which the substrate 200 includes a metallic layer, the heating element 204 may be formed by removing (e.g., etching) excess portions of the metallic layer from the substrate 200. In these implementations, the remaining metallic layer may form the heating element 204. In other implementations, the heating element 204 may be formed from wires that are connected to the substrate 200. For example, the wire heating elements may be embedded in the substrate or sandwiched between two layers of the substrate. In one specific example, a heating unit 202 may include a polyimide or polyester sheet with etched metal heating elements. In another specific example, a heating unit 202 may include a wire sandwiched between two silicone layers that are vulcanized together (e.g., ½ mm thickness total). In another specific example, a heating unit 202 may include an etched metal layer sandwiched between silicone layers.

The substrate 200 can include one or more heating elements 204 that can be arranged in a variety of different ways. In some implementations, a substrate 200 can include a single heating element 204 (e.g., FIG. 2B). In other implementations, a substrate 200 can include multiple heating elements 204 (e.g., FIG. 2C). The multiple heating elements 204 may be separate from one another. In other cases, any number of heating elements 204 may be connected in series and/or parallel.

The heating elements 204 may have a linear and/or curved shape. Some of the heating elements 204 illustrated in the figures (e.g., FIG. 2C) are laid out in a tortuous shape in order to distribute heat along the surface of the substrate 200 that delivers heat to the user's body. In other examples, the heating elements 204 can be laid out in a circular shape (e.g., FIG. 2E) to generate a circular heating zone. It is contemplated that the heating elements 204 may be laid out in other shapes in addition to those illustrated herein.

If the heating unit 202 includes multiple heating elements 204, the multiple heating elements 204 can be arranged in a variety of different ways. In some implementations, the heating elements 204 can be arranged next to one another (e.g., FIG. 2C). In other implementations, the heating elements 204 may be arranged such that one heating element 204 surrounds another heating element 204. In still other implementations, a heating element 204 may be intertwined with another heating element 204 in a different manner.

Figure 2B:
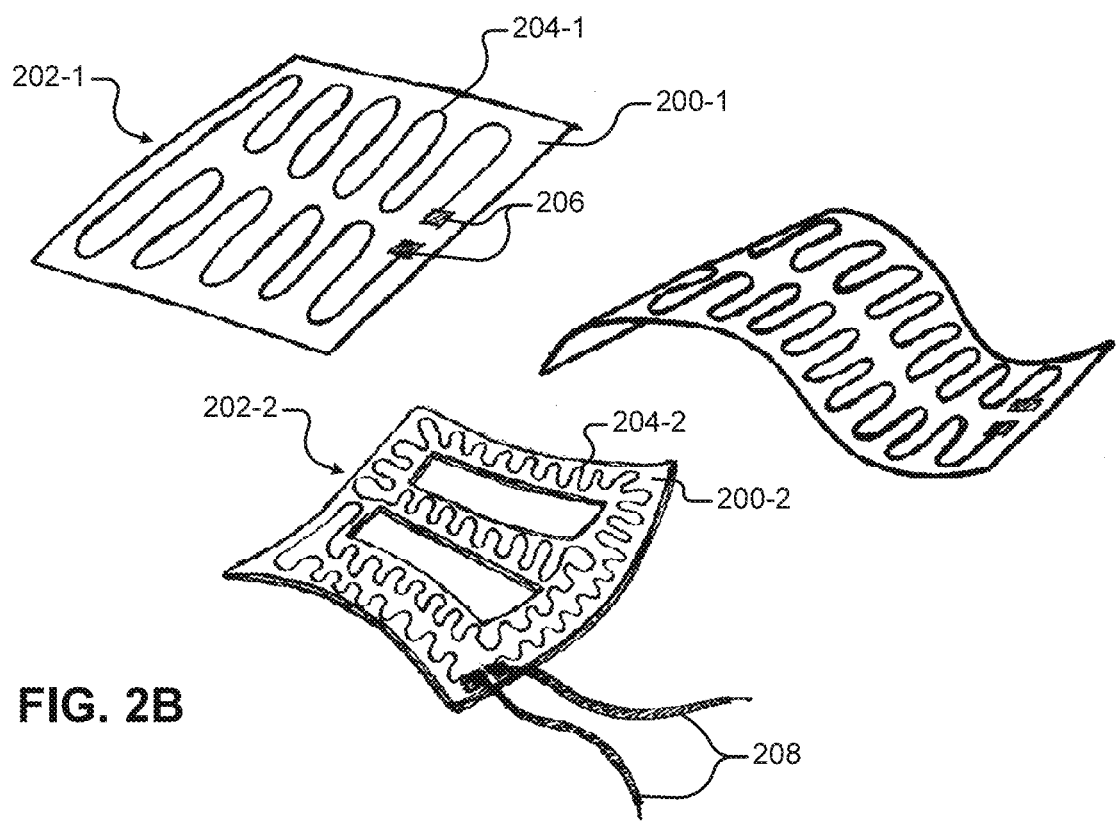
Figure 2C:
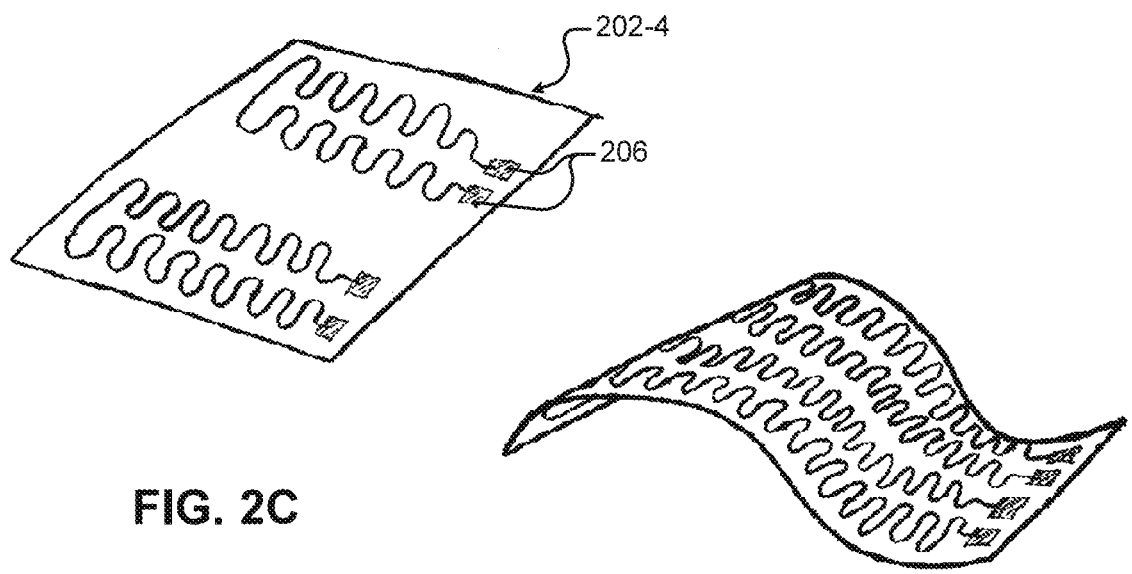
Figure 2D:
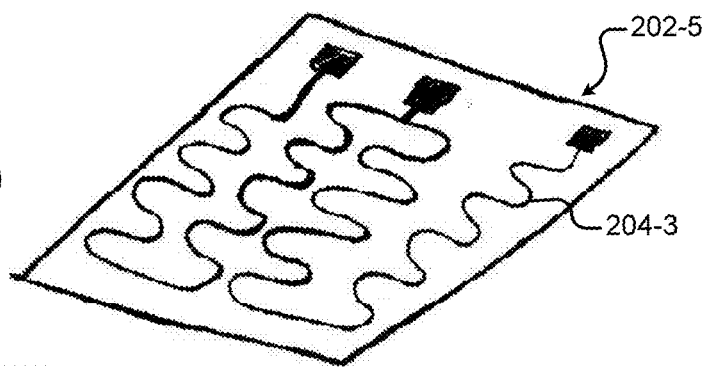
Figure 2E:
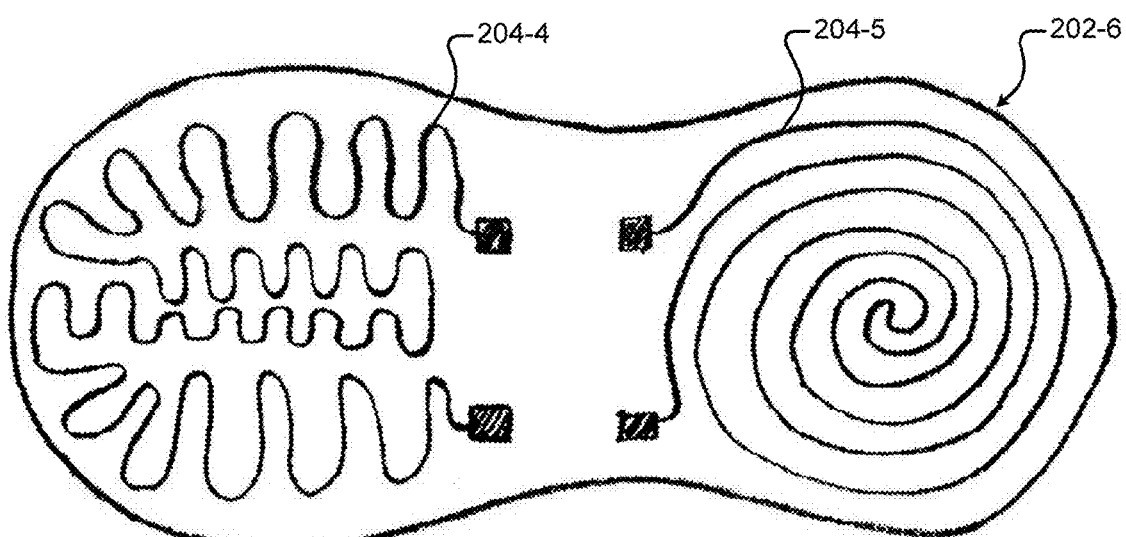
Figure 2F:
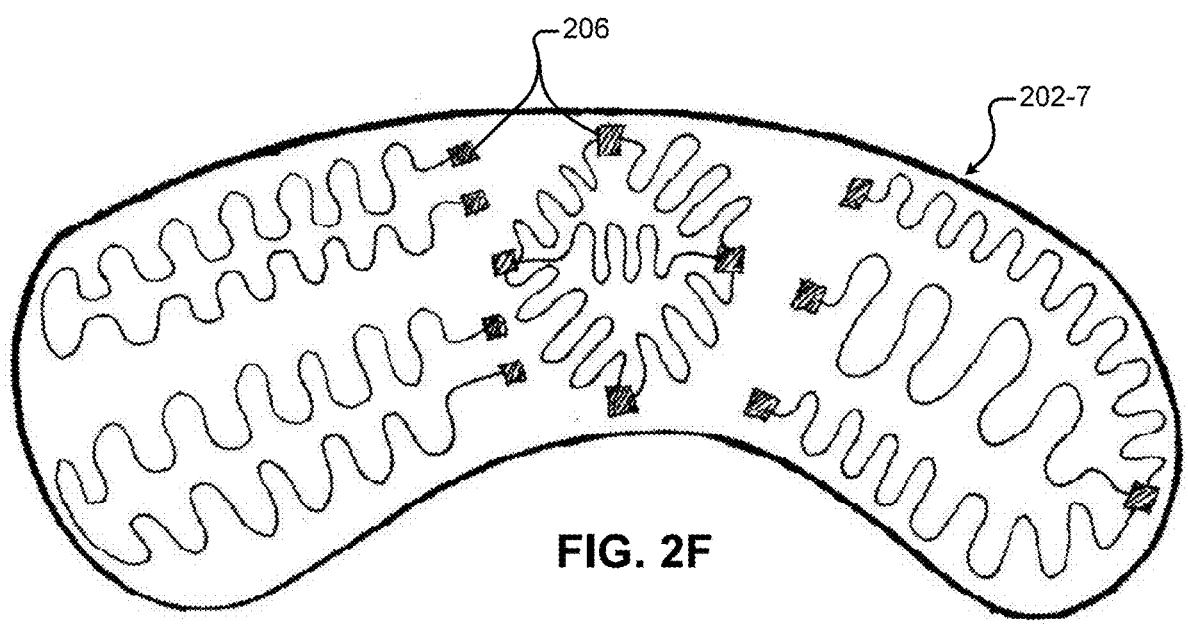
Figure 3A:
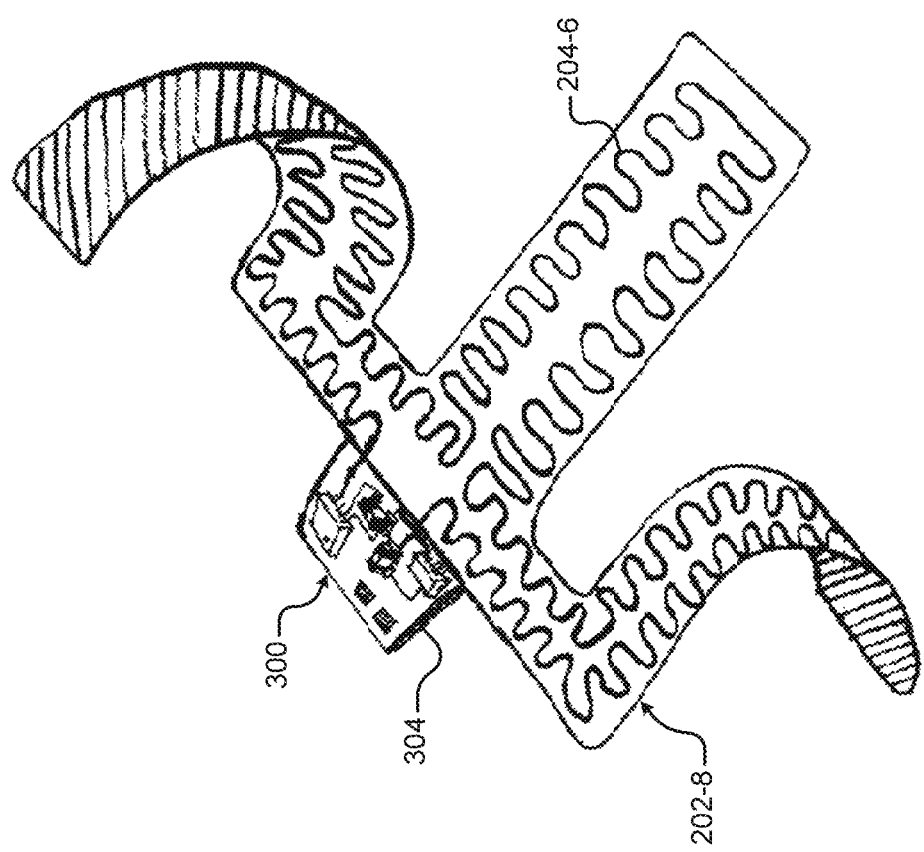
FIGS. 3A-3D illustrate example heating units connected to heating device electronics.
Figure 3B:
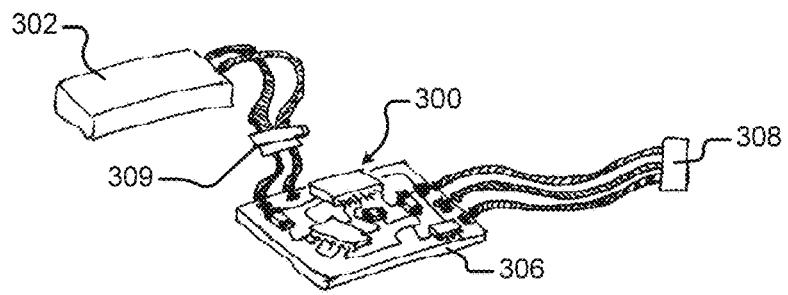

Referring to FIG. 2B, the heating units 202 may include heating element contacts 206. The heating element contacts 206 are electrically coupled to the heating elements 204. In some examples, the heating element contacts 206 may be formed from the same material as the heating element 204. For example, the heating element contacts 206 may be the ends of wires used for heating elements 204 or etched areas fabricated along with etched heating elements 204.

The heating element contacts 206 may provide points where electrical contact (e.g., a low resistance contact) can be made with the heating element 204. For example, the device electronics 300 may electrically couple to the heating elements 204 via heating element contacts 206. A heating element 204 may include two or more heating element contacts 206. In some implementations, a single heating element 204 may include heating element contacts 206 at each end of the heating element 204 (e.g., FIG. 2B). Additionally, or alternatively, a heating element 204 may include multiple heating element contacts 206 along the heating element 204 (e.g., FIG. 2D). Although the device electronics 300 may be coupled to the heating elements 204 via heating element contacts 206 and wires 208, the device electronics 300 may be coupled to the heating elements 204 via other types of electrical coupling. For example, in some implementations, the device electronics 300 may be included on the substrate 200 and may be connected to the heating elements 204 via a continuous connection, such as a set of metal traces between the device electronics 300 and the heating elements 204.

The device electronics 300 deliver power to a heating element 204 via heating element contacts 206 for the heating elements 204. For example, the device electronics 300 may deliver power to a single heating element 204 having two heating element contacts 206 by delivering power to the heating element 204 between the two contacts 206. As another example, if the heating element 204 includes three contacts (e.g., FIG. 2D and FIG. 2F), the device electronics 300 may deliver power to a first portion of the heating element 204 between a first pair of heating element contacts 206 on opposite sides of the first portion of the heating element 204. Additionally, in this example, the device electronics 304 may deliver power to a second portion of the heating element 204 between a second pair of heating element contacts 206 on opposite sides of the second portion of the heating element 204. In this example, one of the three heating element contacts 206 is included in both the first and second pairs of heating element contacts 206.

The device electronics 300 control heat generated by the heating elements 204 by controlling the delivery of power to the heating elements 204. For example, the device electronics 300 may control power delivered to a heating element 204 by controlling the voltage applied across the heating element 204 (i.e., between two contacts 206). As another example, the device electronics 300 may control the power delivered to a heating element 204 by controlling the current through the heating element 204. In some implementations, the heating device 100 (e.g., the device electronics 300) may include maximum power delivery values, such as a threshold power/current/voltage level at which the heating device 100 may limit the delivery of power to one or more heating elements 204.

The layout of the heating elements 204 defines the heating zones. In some implementations, the shape of the substrates 200 can be configured to match the heating zones. For example, with respect to the substrate 200-3 of FIG. 2A that includes a plurality of lobes 210, each of the lobes 210 can include one or more heating elements 204. In this example, each of the lobes 210 may include a heating zone.

In some implementations, the substrate 200 may include an adhesive layer (not illustrated). The adhesive layer can attach to the substrate 200 on one surface and adhere to the user's skin on the other surface. The skin adhesive layer may include, but is not limited to, silicone gels, acrylic adhesives, polyurethane gels, and hydrogels. The adhesive layer may include a removable cover layer that can be peeled from the adhesive layer to expose the adhesive layer. The removable cover layer may be a smooth layer that adheres to the underlying adhesive but does not adhere to the user. In some implementations (e.g., FIG. 10D), the adhesive layer and removable cover layer may be attached to the device package instead of the substrate 200 of the heating unit 202. In some implementations, the adhesive layer may be removable. For example, the adhesive layer may include an adhesive or other type of attachment for connecting to the substrate/package. In some implementations, the heating device 100 may include other types of adhesive layers (not shown) used in construction of the heating device 100, such as adhesive layers that adhere different packaging components to one another.

The device electronics 300 can control heat generated by the heating elements 204 based on a heating profile, user input, and/or sensor data (e.g., in the manual/automatic/mixed mode). The device electronics 300 may also perform a variety of other functions described herein. For example, the device electronics 300 can provide communication with the user device 102, control charging of the battery 302, and control interactions with user interface devices.

The device electronics 300 can be mounted in a variety of different locations. In some implementations, the device electronics 300 can be mounted (e.g., soldered) to the substrate 200 (e.g., FIG. 3A). In FIG. 3A, the device electronics 300 are included on a portion of the substrate 304 that is more rigid than the rest of the substrate. In other implementations, the device electronics 300 may be attached to a flexible portion of the substrate.

Although the device electronics 300 can be mounted to a substrate 200, in some implementations, at least a portion of the device electronics 300 can be mounted in another location. For example, with respect to FIG. 3B, the device electronics 300 can be mounted to a printed circuit board (PCB) 306 that is external to the substrate 200, but included in the device package. In these implementations, the PCB 306 including the device electronics 300 can be electrically coupled to the heating elements 204 via the heating element contacts 206.

Figure 3C:
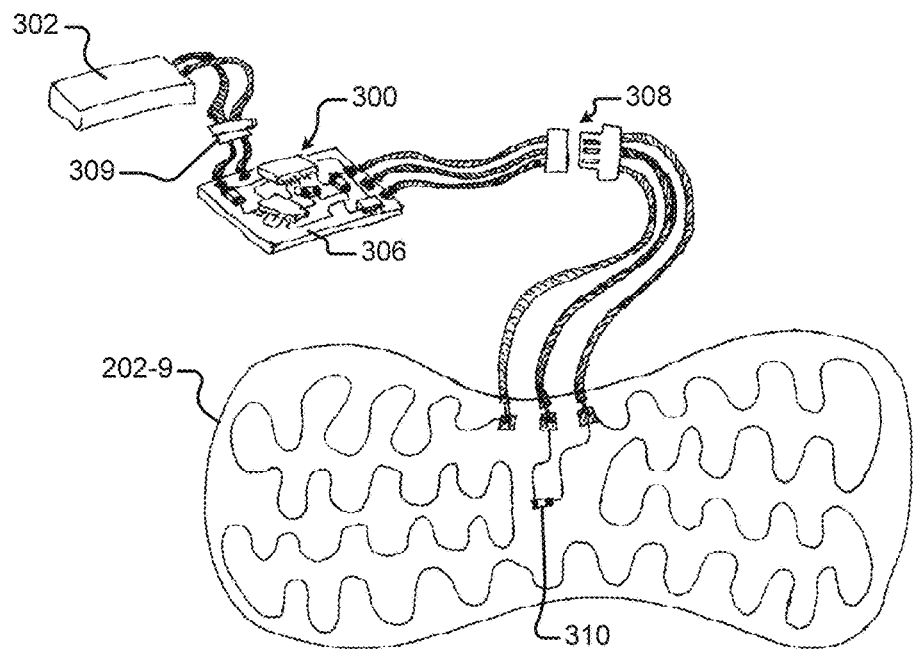
Figure 3D:
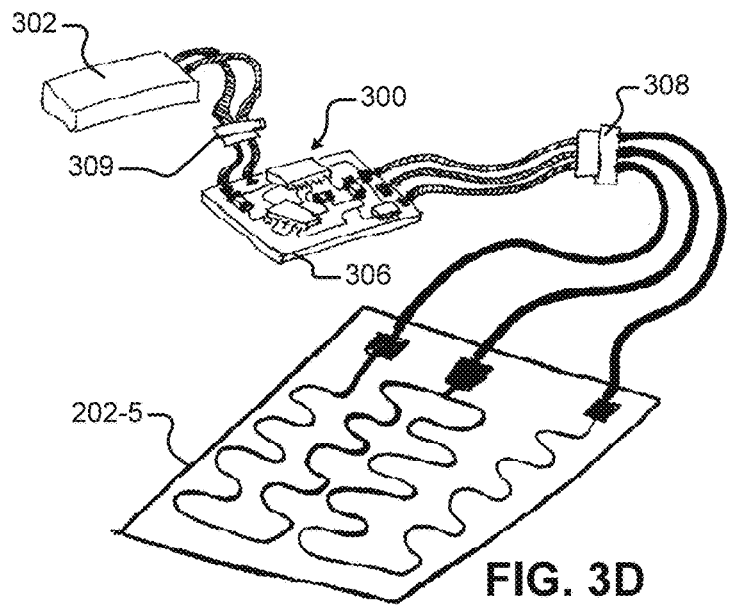

In some implementations, an external PCB 306 can be wired (e.g., permanently) to the heating element contacts 206. For example, the external PCB 306 can be soldered or otherwise connected to the heating element contacts 206 (e.g., via wires). In other implementations, as illustrated in FIGS. 3B-3D, the heating device 100 can include a heating unit connector 308 that can electrically couple the external PCB 306 to the heating elements 204. The heating unit connector 308 can include two connection components that can be disconnected from one another so that the external PCB 306 and the heating elements 204 can be disconnected from one another. The heating unit connector 308 can include an electronics side and a heating unit side. The two sides of the connector can be connected to electrically couple the device electronics 300 and the heating elements 204. The illustrated connector 308 is a low-profile connector, such as a Molex 36877-0004 connector. The connector 308 may have a positive-latching connector design so that the connector 308 does not become detached during use. Additionally, the connector 308 may be water-proof to allow for easy cleaning or moisture exposure during use. In some implementations, the PCB 306 can be connected to the heating elements 204 with other types of detachable connectors than those illustrated. For example, the external PCB 306 may include a socket into which the heating unit can be inserted, such as a Universal Serial Bus (USB) connection or other low profile power connector. As an additional example, the heating unit 202 may include a socket into which the external PCB wires/connectors can be inserted.

The heating unit 100 may also include a battery connector 309. The battery connector 309 can include two connection components that can be disconnected from one another so that the external PCB 306 and the battery 302 can be disconnected from one another. The battery connector 309 may include similar connectors as described with respect to the heating unit connector 308.

In implementations where the device electronics 300 are detachable from the heating unit(s) 202 (e.g., via the heating unit connector 308), different heating units 202 having different arrangements of heating elements 204 (e.g., layout/number of heating elements) and sensors may be interchangeable with the same device electronics 300. In other cases, a new heating unit 202 having the same arrangements as the old heating unit 202 could be swapped out (e.g., in the case the old heating unit is broken or worn out).

FIGS. 3C-3D illustrate how different heating units 202 having different heating element and sensor arrangements can be connected to the device electronics 300 via the heating unit connector 308. In FIG. 3C, the device electronics 300 can connect to two heating element contacts 206 for a single heating element 204. The device electronics 300 in FIG. 3C can also connect to a temperature sensor 310 included on the substrate 200. In FIG. 3C, the device electronics 300 can deliver power to the heating element 204 via the heating element contacts 206 and also determine the temperature indicated by the temperature sensor 310.

In FIG. 3D, the device electronics 300 are connected to a heating unit 200-5 that is different than the heating unit 202-9 of FIG. 3C. In FIG. 3D, the heating unit 202-5 includes three heating element contacts for a single heating element, whereas the heating unit 202-9 of FIG. 3C includes a heating element and a temperature sensor 310. Although the heating element and sensor arrangement are different, the device electronics 300 may be configured to operate the heating units 200 of FIG. 3C and FIG. 3D. For example, the device electronics 300 can be configured to deliver power to the heating element of FIG. 3C and determine the temperature indicated by the temperature sensor 310. The device electronics 300 can then be reconfigured to deliver power to the heating element of FIG. 3D via the three heating element contacts.

In some implementations, the device electronics can deliver power to the heating elements 204 and measure temperature using the same circuits. For example, if the temperature sensor 310 is a resistive temperature sensor (e.g., a thermistor or resistance temperature detector), the device electronics 300 may include circuits that deliver power to the sensor 310 in a manner similar to the heating elements 204, determine the resistance of the sensor 310, and determine temperature based on the determined resistance. In other implementations, the device electronics 300 may include additional components that interface with the temperature sensor 310, such as circuits that interface with a thermocouple or a digital temperature sensor. The device electronics 300 may include switches (e.g., discrete switches and/or switches included on a microcontroller) that may be used to reconfigure the functionality for each of the contacts. Although the figures of 3C-3D illustrate reconfiguration of the device electronics 300 to operate with three different types of connections (e.g., heating element and sensor connections), device electronics 300 may be configured to operate while connected to any number of connections.

As described with respect to FIGS. 3C-3D, the device electronics 300 can be configured (e.g., using switches) to couple to sensors and/or heating elements 204 using the same contacts. In some implementations, the device electronics 300 may be configured to operate with a variety of different heating units 202 having a different number of contacts, a different number of heating elements 204, different arrangements of heating elements 204, and/or different types of sensors. The device electronics 300 may determine how to operate with different heating units 202 in a variety of different ways. In some implementations, a user may manually configure the device electronics 300 (e.g., using a GUI on the user device 102) to operate with a specific heating unit 202. For example, the user may enter a model number of the heating unit 202 into the GUI that indicates to the user device 102 and/or heating device 100 how to configure the device electronics 300 for operating the specific heating unit 202. In some implementations, the device electronics 300 may automatically detect the specific heating unit 202 attached to the device electronics 300 and then correctly operate the specific heating unit 202. The device electronics 300 may automatically detect the heating unit 202 in a variety of ways, such as via applying test voltage/current to determine heating element arrangement/resistance and whether a sensor is attached. In some cases, a heating unit 202 may include an identification circuit (e.g., a ROM) that indicates details of the heating unit 202 to the device electronics 300, such as the number of heating elements 204, the arrangement of heating elements 204, and the number/arrangement of sensors. The device electronics 300 may determine the configuration of the heating unit 202 and how to operate the heating unit based on communication with the identification circuit (e.g., by reading the ROM).

Figure 1C:
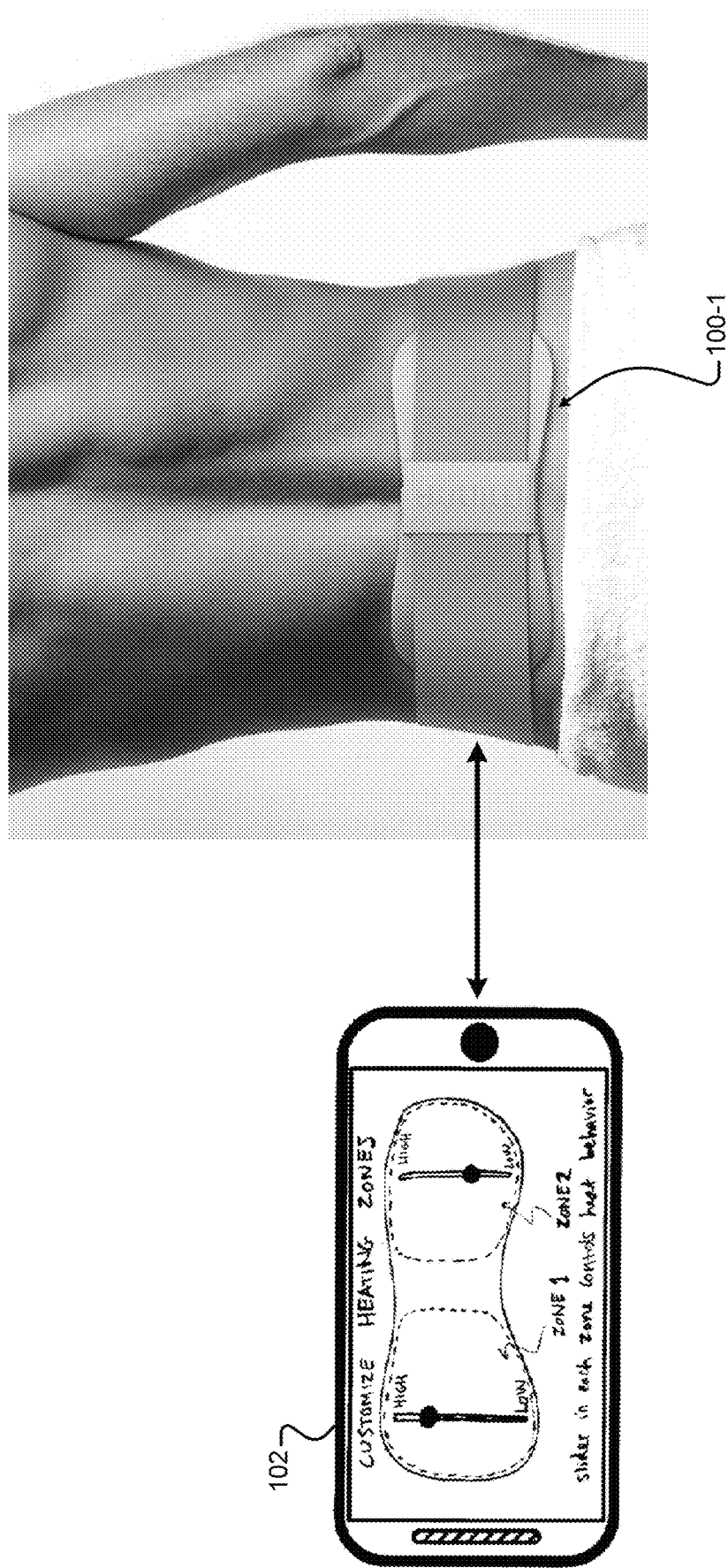

FIG. 1C and FIG. 4 illustrate a heating device in communication with a user device (e.g., a cell phone). The device electronics 300 can include wireless/wired communication technology that communicates with the user device 102. As described herein with respect to FIG. 8, the user device 102 can communicate with remote computing devices 802 via a network 804, such as the internet. The user device 102 can also provide a variety of functionality with respect to the heating device 100. In some implementations, the user device 102 may generate a GUI (e.g., FIGS. 9A-9K) that the user may use to perform a variety of different operations with respect to the heating device 100. For example, the user may interact with the GUI to control heating of the heating device 100. In some examples, the user may interact with GUI element controls to control heating. In other examples, the user may select a heating profile and upload the heating profile to the heating device 100 using the GUI. The user may select a profile on the heating device 100 to run, select a heating profile from the user device 102 to load onto the heating device 100, and/or retrieve a heating profile from a remote server 802 to run on the heating device 100. The user may also monitor various heating device parameters, such as the battery status, the currently running heating profile (e.g., a heating map), and the remaining time for which the heating device 100 may run the heating profile. Additional features of the user device 102, heating device 100, and aspects of communication between the devices 100, 102 are described herein.

FIG. 4 is a functional block diagram of an example heating device 400. The various modules included in the heating device 400 represent functionality (e.g., circuits and other components) included in the heating devices 100. Modules of the present disclosure may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits, etc.). Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein. The device electronics 300 of the heating devices 100, 400 described herein are only example device electronics. As such, the types of electronic components used to implement the device electronics may vary based on design considerations.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

The heating device 400 includes a processing module 402 (e.g., a processor and/or microcontroller), a communication module 404, an interface module 406, a power module 408, a heating control module 410, and a temperature sensing module 412. The heating device 400 may also include a battery 414, heating elements 416-1, 416-2, . . . , 416-N, and one or more sensors (e.g., a temperature sensor 418). The processing module 402 communicates with the modules included in the heating device 400. For example, the processing module 402 may transmit/receive data to/from the modules and other components of the heating device 400. As described herein, the modules may be implemented by various circuit components. Accordingly, the modules may also be referred to as circuits (e.g., a communication circuit, temperature sensing circuit, heating control circuit, interface circuit, and power circuit).

The processing module 402 may communicate with the memory 420. The memory 420 may include computer-readable instructions that, when executed by the processing module 402, cause the processing module 402 to perform the various functions attributed to the processing module 402 herein. The memory 420 may include any volatile, non-volatile, magnetic, or electrical media, such as RAM, ROM, NVRAM, EEPROM, Flash memory, or any other digital media. In some implementations, the processing module 402 may include a microcontroller which may include additional features associated with other modules, such as an integrated Bluetooth Low Energy transceiver.

The temperature sensing module 412 is electrically coupled to the temperature sensor 418. The temperature sensor 418 indicates the temperature in the area in which the temperature sensor 418 is located. The temperature sensing module 412 may determine the temperature in the location of the temperature sensor 418. In some implementations, the temperature sensor 418 may generate a temperature signal that indicates the temperature in the area. For example, the temperature sensor 418 may generate a digital signal that the temperature sensing module 412 may use to determine the temperature. As another example, if the temperature sensor 418 is a passive thermistor, the temperature sensing module 412 may measure a current/voltage generated by the temperature sensor 418 and determine the temperature based on the measured current/voltage.

The interface devices 422 may include user-feedback devices and/or user input devices. For example, user-feedback devices may include, but are not limited to, a display (e.g., a touchscreen display), vibration devices, lighting devices (e.g., LEDs), and a speaker. The interface module 406 can control the user-feedback devices. For example, the interface module 406 may include display control/driver circuits, vibration control circuits, LED control circuits, speaker control circuits, and/or other control circuits. In some implementations, the processing module 402 may control the interface devices 422 via the interface module 406. For example, the processing module 402 may generate control signals that the interface module 406 uses to control the interface devices 422. For example, the interface module 406 may include circuits that deliver power/data to the display/vibration/lighting devices, while the processing module 402 controls the delivery of power/data to the display/vibration/lighting devices.

Example user input devices include, but are not limited to, buttons (e.g., manual buttons and/or capacitive touch sensors), switches, and a touchscreen. The interface module 406 may include circuits for receiving user input signals from the user input devices. The processing module 402 may receive the user input signals from the interface module 406 and take a variety of actions based on the user input signals. For example, the processing module 402 may detect a user pushing an on/off button and then power on (i.e., turn on) the heating device 100 in response to detection of the button push. As another example, the processing module 402 may detect a user pushing an on/off button while the heating device 100 is powered on. In this example, the processing module 402 may power off (i.e., turn off) the heating device 100 in response to detection of the button push. As another example, the processing module 402 may detect a user pushing a heating control button (e.g., +/−buttons) and then increment/decrement the heat generated by the heating elements 416 (or temperature setting) based on detection of the button push.

The communication module 404 can include circuits that provide wired and/or wireless communication with the user device 102. In some implementations, the communication module 404 can include wired communication circuits, such as USB communication circuits. In some implementations, the communication module 404 can include wireless communication circuits, such as Bluetooth circuits and/or WiFi circuits.

Using the communication module 404, the heating device 400 and the user device 102 can communicate with each other. The processing module 402 can transmit/receive data to/from the user device 102 via the communication module 404. Example data may include heating profiles and other information requests, such as status updates (e.g., charging status, battery charge level, and/or heating device configuration settings). The processing module 402 can also receive instructions/commands from the user device 102 (e.g., user-input instructions), such as instructions to increase/decrease heating. In some implementations, the processing module 402 can receive instructions/commands from the user device 102 to power on or power off the heating device 100. For example, the user device 102 may transmit a power-on/power-off instruction to power on/off the heating device 100. In some implementations, the processing module 402 (e.g., a microcontroller) may include circuits that provide wired/wireless communication (e.g., USB/Bluetooth). In some implementations, the user device 102 can transfer update data to the heating device 400 to update the software/firmware of the heating device 400.

The heating device 400 may include a battery 414 (e.g., a rechargeable or non-rechargeable battery). An example battery may include a Lithium-Ion or Lithium-Polymer type battery, although a variety of battery options are possible. A power source (e.g., a wall adapter power cord or USB power plug) can be plugged into the power input port (e.g., FIG. 1A) of the heating device 400 to charge the battery 414. The heating device 400 includes a power module 408 that may control charging of the battery 414, regulate voltage(s) of the device electronics 300, regulate power output to the device electronics 300, and monitor the state of charge of the battery 414. In some implementations, the battery itself may contain a protection circuit module (PCM) that protects the battery from high current discharge, over voltage during charging, and under voltage during discharge. In some implementations, the power module 408 may include circuits configured to modulate the voltage and current into the battery 414 during charging. For example, the power module 408 may include a Microchip MCP73832 charge control IC and supporting passive components. The power module 408 may also include electro-static discharge (ESD) protection.

In some implementations, the power module 408 may control charging of the heating device 400 from the user device 102. For example, the heating device 400 may draw power from the user device 102 (e.g., a laptop or tablet), which may allow the heating device 400 to run longer. In some implementations, the power module 408 may control charging of the user device 102 from the heating device 400. For example, the heating device 400 can deliver power to the user device 102 (e.g., a phone or tablet) to extend the battery life of the user device 102, which the user may be using to control the heating device 400. In some cases, if the user device 102 is in communication with the heating device 400 and the battery is running low on the user device 102, the user device 102 may prompt the user to plug into the heating device 400 in order to charge the battery of the user device 102. In other cases, if the user device 102 is in communication with the heating device 400 and the battery 414 is running low on the heating device 400, the heating device 400 may prompt the user to plug the heating device 400 into the user device 102 in order to charge the battery 414 of the heating device 400 (e.g., prompt via a GUI on the user device 102).

The processing module 402 along with the heating control module 410 can control the amount of heat generated by the heating elements 416. For example, the heating control module 410 can include electronics that control the amount of power delivered to the heating elements 416. In one example, the heating control module 410 can include electronics that switch on/off the delivery of power to the individual heating elements 416. As another example, the heating control module 410 can include electronics that can incrementally adjust the power delivery to the heating elements 416 (e.g., adjust current and/or voltage).

The processing module 402 may control the heating control module 410 to deliver power to the heating elements 416 according to user input and/or a heating profile. In some implementations, the heating control module 410 may include metal-oxide semiconductor field-effect transistor devices (MOSFETs) (e.g., power MOSFETs) that are controlled by a gate voltage generated by the processing module 402 (e.g., a microcontroller). In implementations where MOSFET devices are used to control current through the heating elements 416, the MOSFETs may be controlled via pulse-width modulation (PWM) signals or on/off commands generated by the processing module 402 (e.g., microcontroller).

The processing module 402 may control the heating control module 410 in a variety of different modes (e.g., a manual mode, automatic mode, and mixed mode). In the manual mode, the processing module 402 may control the heating control module 410 to deliver power based on user input received via the user input devices on the heating device 400 and/or based on user input received from the user device 102 (e.g., via wireless communication). In the automatic mode, the processing module 402 may control the heating control module 410 to deliver power according to a heating profile. In the mixed mode, the processing module 402 may control the heating control module 410 to deliver power according to a heating profile and/or user input.

The heating device 400 (e.g., memory 420) may store heating profiles that include data indicating how to deliver power to one or more heating elements 416. For example, the heating profiles may include data indicating the voltage (e.g., analog voltage level and/or digital average with PWM) to apply to one or more heating elements 416 over time. As another example, the heating profiles may include data indicating the current to deliver to one or more heating elements 416 over time. A heating profile may include one or more heating element profiles. A heating element profile may include data indicating how to deliver power to a single heating element 416 (e.g., between two heating element contacts). In one example, if the heating device 400 includes two heating elements 416, the heating profile may include two heating element profiles.

The heating profile (e.g., including multiple heating element profiles) can be stored in a variety of ways. In general, the data stored in the heating profile indicates to the processing module 402 and heating control module 410 how to deliver power to the heating element(s) 416. In some implementations, the heating profile may include a plurality of digital values indicating current/voltage to be delivered to the heating element(s) 416 over time. In other examples, the heating profile may be stored as a function that yields current/voltage over time. Note that in some cases, the values stored in the heating profiles may not be voltage or current values over time, but instead may be digital values (e.g., PWM control values) used by the processing module 402 and/or the heating control module 410 to cause power to be delivered to the heating element(s) 416 over time.

FIGS. 5A-5E illustrate example current versus time curves that the heating device 100 may generate according to heating profiles stored on the heating device 100. The time values associated with the curves may vary, depending on the implementation. As such, the units of time are not explicitly noted on the graphs. In some implementations, the graphs may represent a duration on the order of seconds (e.g., 10-30 seconds in duration). In other implementations, the graphs may represent a duration on the order of minutes (e.g., 1-5 minutes). Although the Y-axis is labeled as current (i), the curves may also represent voltage/power delivered to heating elements.

Figure 5A:
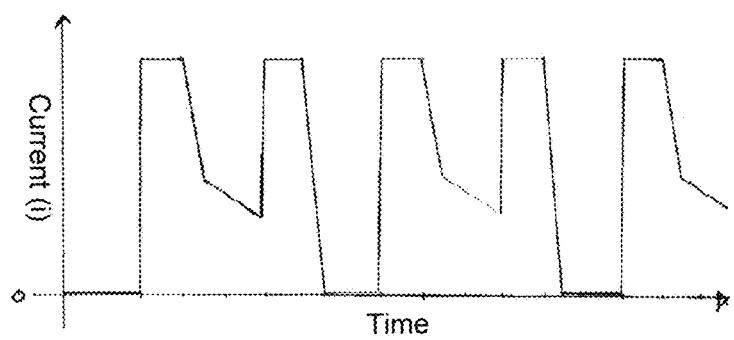
FIGS. 5A-5E are example current versus time graphs for a heating device.
Figure 5B:
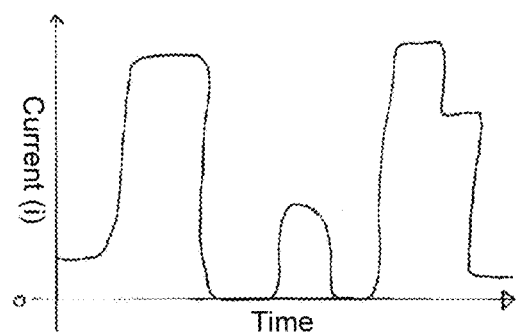
Figure 6C:
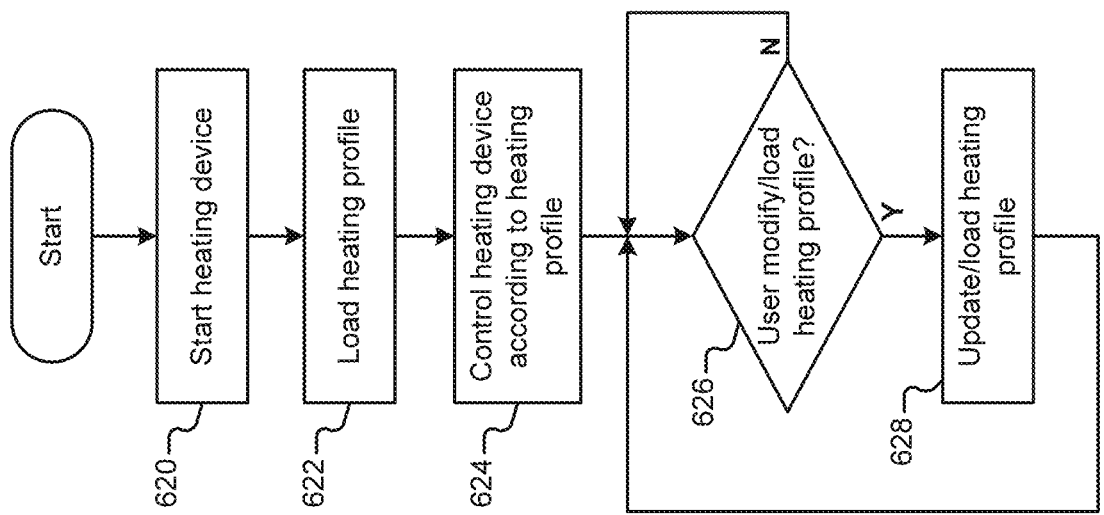
FIGS. 6A-6C are flow diagrams that illustrate different modes of heating device operation.
Figure 6B:
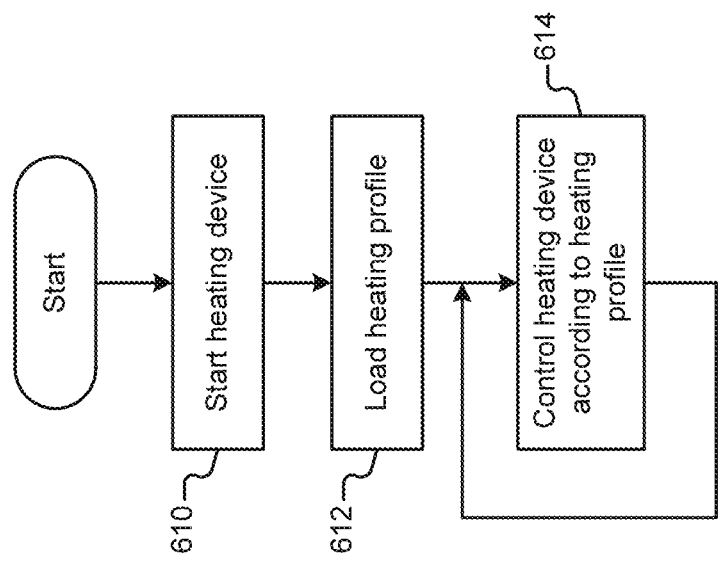
Figure 6A:
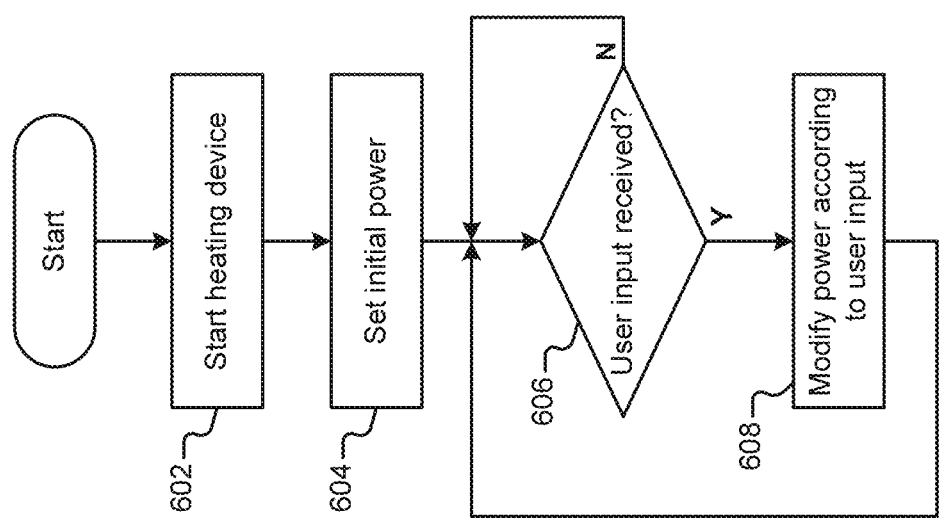

FIGS. 5A-5B illustrate current versus time for a single heating element. FIG. 5A illustrates delivering power to a heating element in a repetitive pattern. FIG. 5B illustrates delivering power to the heating element in a more irregular pattern. The pattern in FIG. 5B may be repeated (e.g., periodic) or non-repetitive.

Figure 5C:
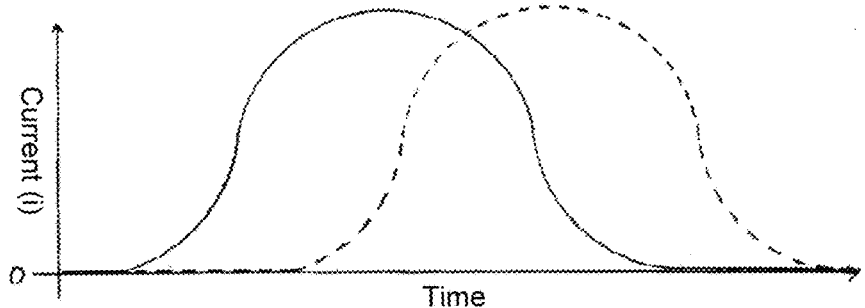
Figure 5D:
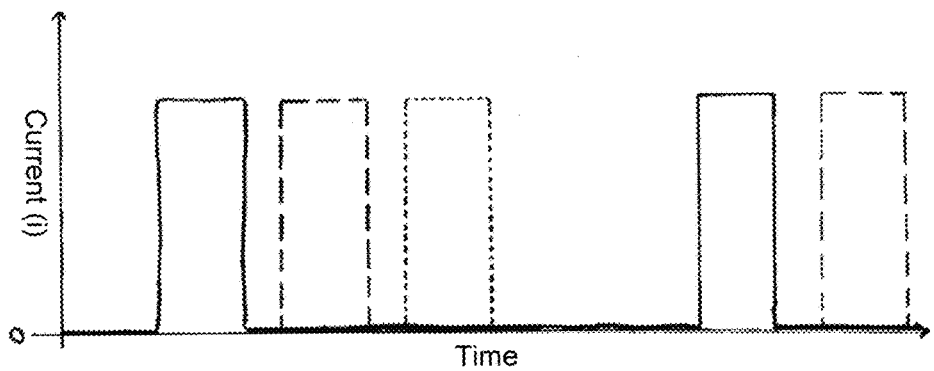

FIGS. 5C-5D illustrate current versus time for multiple heating elements. FIG. 5C illustrates a first and second current delivered to first and second heating elements. The first curve (solid line) may be stored as a first heating element profile for the first heating element. The second curve (broken line) may be stored as a second heating element profile for a second heating element. The heating profile for FIG. 5C may include both the first and second heating element profiles. Note that the two heating element profiles of FIG. 5C store the same current curve, but the current curves are offset in time from one another. FIG. 5D illustrates three current curves for three separate heating elements. The three curves include one solid curve and two broken curves. The three current curves are similar in shape, but offset in time from one another.

In some implementations, the user may perceive the offsetting of similar curves as a wave of heat that passes across the heating device 100. For example, if a heating device 100 has first and second heating elements next to one another and operates according to FIG. 5C, the user may first feel the heat generated by the first heating element and then feel a similar heating in the adjacent second heating element as though the heat is flowing across the heating device from one heating element to the next. In some implementations, the heating device 100 and/or user device 102 may include controls (e.g., buttons and/or GUI elements) that the user can use to cause the time offset between two or more heating elements.

Figure 5E:
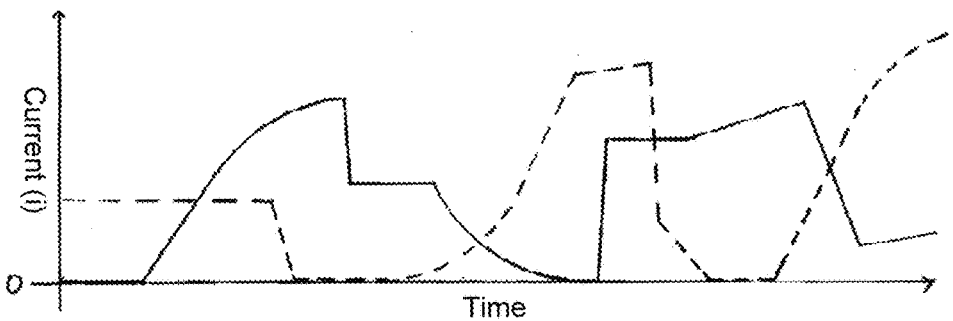

FIG. 5E illustrates two different current curves for two separate heating elements. Each of the current curves in FIG. 5E may be repeated or non-repetitive. The current curves of FIG. 5E may provide an irregular pattern of heating that the user may perceive as unpredictable.

FIGS. 5A-5E illustrate a variety of different heating patterns. Heating profiles may include patterns similar to, or different from, the illustrated heating patterns (e.g., regular/irregular/repetitive/non-repetitive). Additionally, a heating profile may include heating patterns that transition from repetitive to non-repetitive and/or from regular to irregular (or vice versa) over time. As described herein, a user may create new heating patterns or modify existing heating patterns while using the heating device or working offline.

The duration of heating pulses (e.g., as illustrated in FIG. 5D) deliverable by the heating device may vary depending on a variety of parameters. In some implementations, the duration of heating pulses may be selected based on response times of the heating device 100 and/or the user's ability to perceive the delivered heat. For example, response times of the heating device 100 (e.g., heating elements 204) affecting the time required to deliver heat to a user may determine the minimum duration of heating pulses. As another example, a user's ability to perceive the changes in heating being delivered may determine the minimum duration of heating pulses. For example, if a user is unable to differentiate heating pulses having a duration of less than one second from heating pulses having a duration of one second, then the minimum pulse duration may be set to one second. The ability of a user to perceive changes in heating may depend on the region of the body to which the heating device 100 is applied. Accordingly, the minimum duration of heating pulses may also depend on where the heating device 100 is to be applied. In some implementations, the pulses illustrated in FIG. 5D may have a duration on the order of a second or more, although the pulses may be set to a duration of less than a second if perceptible by the user.

In some implementations, the heating device 100 can control power delivered to the heating elements 204 based on a sensed and/or estimated temperature. For example, the heating device 100 may control the delivery of power to meet a target temperature that is adjustable by the user. As another example, the heating device 100 may control the delivery of power such that the temperature remains less than a threshold temperature, such as a temperature threshold set by a user or a maximum allowable temperature (e.g., in factory settings).

The heating device 100 can control the delivery of heat to the user based on the temperature of the heating device 100 in proximity to the user (e.g., the temperature of a heating zone). In some implementations, the heating device 100 can include one or more temperature sensors (e.g., 310 in FIG. 3C and 1124 in FIG. 11B) that sense temperatures in one or more heating zones. In implementations where the heating device 100 includes one or more temperature sensors, the heating device 100 can control heating based on temperature indicated by the temperature sensor.

In implementations where the heating device 100 does not include a temperature sensor, the processing module 402 may estimate the temperature and control heating based on the estimated temperature. The processing module 402 may estimate the temperature based on one or more factors, such as the amount of power delivered to the heating elements 204 (e.g., voltage or current) and the amount of time over which the power has been delivered. In some implementations, the memory 420 may include temperature estimation models and/or tables that the processing module 402 may use in order to estimate temperature. For example, the models/tables may indicate an estimated temperature for power values and/or a heating profile over time. The processing module 402 may also determine the temperature based on a combination of temperature indicated by the temperature sensors and the estimated temperature. In some implementations, the memory 420 may include models/tables that use sensed temperatures to estimate additional temperatures.

Although the heating device 100 can control heating based on temperature (e.g., a target temperature), in some implementations, the heating device 100 can control heating based on alternative and/or additional parameters, such as an amount of energy/heat delivered to a user. For example, the heating device 100 may control the delivery of heat to reach a target amount or rate of energy/heat delivery. The heating device 100 may determine the amount of energy/heat delivered based on a variety of parameters, such as the delivered current/voltage and the amount of time over which the current/voltage was delivered.

In some implementations, the heating device 100 may include components that indicate an amount of pressure placed on the heating device 100 (e.g., a pressure sensor). Such components may be embedded in and/or attached to the substrate 200 or device packaging. In these implementations, the heating device 100 may control heating based on the indicated pressure (e.g., as indicated by the pressure sensor). In one example, the heating device 100 may decrease an amount of heat being delivered to the user if the pressure sensing components indicate that the heating device 100 is pressed more firmly against the user, as the pressure may be indicative of a close contact and better heat transfer to the user. In another example, the heating device 100 may be configured to increase heating in response to increased pressure placed on the heating device 100. In this example, if a user presses their hand on top of the heating device to increase pressure on the heating device 100, the heating device 100 may respond by delivering more heat to the area.

FIGS. 6A-6C illustrate example methods describing operation of the heating device 100 in different modes of operation. FIG. 6A illustrates an example method describing operation of the heating device 100 in the manual mode. In FIG. 6A, the heating device 100 is initially started (e.g., using an on/off button) at block 602. At block 604, the heating device 100 (e.g., the device electronics 300) sets an initial power delivery to the one or more heating elements 204. At block 606, the heating device 100 then waits for user input, which may include user interaction with manual controls (e.g., user input buttons) on the heating device 100 and/or user interaction with a GUI on the user device 102. Example user input may include incrementing/decrementing heat (e.g., power delivery) to be delivered to the user. If the heating device 100 receives user input, the heating device 100 may modify power delivery to the one or more heating elements 204 according to the user input at block 608.

FIG. 6B illustrates an example method describing operation of the heating device 100 in the automatic mode. In FIG. 6B, the heating device is initially started at block 610. Upon starting, the heating device 100 may load a heating profile at block 612. For example, the heating device 100 may load a stored heating profile or may receive a heating profile from the user device 102. At block 614, the heating device 100 controls heat (e.g., power delivery) for one or more heating elements 204 according to the loaded heating profile.

FIG. 6C illustrates an example method describing operation of the heating device 100 in the mixed mode. In blocks 620-624 of FIG. 6C, the heating device 100 is initially started, loads a heating profile, and controls heat according to the heating profile, as described with respect to FIG. 6B. In the mixed mode, at block 626, the user may modify the heating profile and/or load another heating profile onto the heating device 100. For example, the user may provide user input that modifies the currently running heating profile via manual controls on the heating device 100 and/or GUI controls on the user device 102. The user may also load new heating profiles to run on the heating device 100. For example, the user may select a new heating profile stored on the heating device 100 or download a heating profile from the user device 102 to the heating device 100. In block 628, the heating device 100 may run the new profile until the user modifies the new profile and/or loads another heating profile.

A positive heating experience for the user may include the immediate delivery of heat to the user's body at the user-desired heating level. However, the ability of the heating device 100 to deliver immediate heat may be limited due to various power delivery limitations associated with the battery and/or other device electronics. For example, limited power output from the battery may prevent the heating device 100 from immediately reaching a desired temperature and/or heat output. As another example, initial power provided to the heating elements 204 may be absorbed by materials in the heating device 100, which may prevent immediate heat transfer to the user. FIGS. 7A-7C are directed to techniques for operating a heating device 100 in a manner that may provide the user with a perception of immediate heat delivery without exceeding power limitations of the battery.

FIG. 7A illustrates an example heating unit 202-10 including four heating elements arranged symmetrically on the substrate. The first heating element 204-7 and the second heating element 204-8 are associated with first and second heating zones, respectively. The first heating element 204-7 covers a first heating zone having a smaller area than the second heating zone covered by the second heating element 204-8. In the example of FIG. 7A, the first heating zone is centrally located on the right side of the substrate. The second heating zone is located around the periphery of the first heating zone.

In order to provide immediate heat delivery to a user, the heating device 100 may be configured to first provide an excess of power to the heating element associated with the smaller area (e.g., the first heating element 204-7). Excess power may refer to an amount of power per area of heating zone that is greater than that desired by the user over the long term in either the first or second heating zones. The provision of excess power may rapidly heat the smaller heating zone. In some cases, the power delivery limitations of the heating device 100 may limit the ability of the heating device 100 to deliver enough power to immediately heat more heating zones, but may allow for immediate heating of a smaller heating zone. Providing the user with immediate heating in such a manner may provide a pleasing user experience. Additionally, depending on positioning of the heating device 100 on the user's body, the user may not be able to immediately perceive that only a smaller portion of the heating unit is being heated. In this case, the immediate heating may be perceived as being provided across the additional heating zones. The user may perceive immediate heating on the order of seconds (e.g., 3-5 seconds).

After heating the smaller heating zone for a period of time, the heating device 100 may begin providing more power to the larger heating zone (e.g., the second heating zone) to bring the larger heating zone to the user's desired power level. The heating device 100 may also decrease power to the smaller heating zone toward the user's desired power level. After decreasing/increasing power to the smaller/larger heating zones, the smaller and larger heating zones may level out at the user's desired power level(s) for the zones.

In some implementations, the heating device 100 may control the initial power delivery to the smaller heating zone based on a detected temperature associated with the smaller heating zone. For example, the heating device 100 may ramp the power delivery up to a threshold temperature (e.g., a user-specified maximum temperature) and then limit the power delivery such that the threshold temperature is not exceeded.

Implementation of immediate heating may vary based on a variety of factors. Example factors that may affect implementation of immediate heating include, but are not limited to, the area of the heating zones, the amount of heating element material in the heating zones (e.g., length/diameter of wire), heating element geometry within the heating zone, the resistivity of the heating elements, and the voltage/current applied to the heating elements. Although substantially concentric heating zones are illustrated in FIG. 7A, other heating devices may include other arrangements of heating elements/zones. Although immediate heating may be implemented using two heating elements defining two heating zones, immediate heating may be implemented using other numbers of heating elements and heating zones.

FIG. 7B illustrates power delivery per area of heating zone for the first heating element 204-7 and the second heating element 204-8 of FIG. 7A. In FIG. 7B, the first heating element 204-7 receives excess power to provide immediate heating to the user. The first heating element 204-7 delivers power to the user for a period of time before the second heating element 204-8 begins delivering power. Power delivered to the first heating element 204-7 is decreased upon ramping power to the second heating element 204-8. In some implementations, the power delivery per area can be operated as a step function (e.g., the first heating element 204-7). The power delivery per area may also be operated in another manner (e.g., a ramp function as illustrated with respect to the second heating element 204-8). FIG. 7B illustrates a single set of traces for two heating elements. In other implementations, the traces may converge to the same power level or cross one another.

FIG. 7C illustrates a method for providing immediate heating to a user. The heating device 100 may provide immediate heating in a variety of scenarios, such as when the heating device 100 is being turned on or when any burst of heat is desired. In some implementations, the user may manually set the desired power level (e.g., using the GUI). In other implementations, the desired power level may be set according to the heating profile. The method of FIG. 7C is described with respect to FIGS. 7A-7B.

Initially, in block 700, the heating device 100 delivers excess power to the first heating element 204-7 in the first heating zone. After a period of time, in block 702, the heating device 100 starts delivery of power to the second heating element 204-8 in the second zone. In block 704, the heating device 100 increases power to the second heating element 204-8 and decreases power to the first heating element 204-7. In some implementations, the heating device 100 may start increasing power to the second heating element 204-8 at approximately the same time as the heating device 100 starts decreasing power to the first heating element 204-7. In block 706, the heating device 100 maintains the delivery of power to the first and second heating elements 204-7, 204-8.

FIG. 8 illustrates a plurality of user devices 800-1, 800-2, . . . , 800-N in communication with a remote server 802 via a network 804. Each of the user devices 800 is in communication with a different heating device 806-1, 806-2, . . . , 806-N. In FIG. 8, different users may each own/operate one of the user devices 800 and one of the heating devices 806. The remote server 802 may be owned/operated by a party other than the users. For example, the remote server 802 may be operated by the developer/manufacturer of the heating devices 806. In these examples, the developer/manufacturer of the heating devices 806 can provide data and programs to the remote server 802 for download by the user devices 800.

In some implementations, the remote server 802 can provide one or more programs (e.g., applications) to the user devices 800. The one or more programs may be executed by the user devices 800 to interact with the heating devices 806. For example, the one or more programs may generate GUIs on the user device 800 which the user may use to interact with the heating device 806 (e.g., see FIGS. 9A-9K). The user devices 800 may download and execute the one or more programs in order to interact with the heating device 806 (e.g., after the user purchases the heating device).

In some implementations, the remote server 802 may store data that can be accessed by the user devices 800. For example, the remote server 802 can store heating profiles. In some implementations, the heating profiles may be created by the owner/operator of the remote server 802 and uploaded to the remote server 802. In another example, the heating profiles may be created by one or more of the users and uploaded to the remote server 802. Users may download the heating profiles and load the heating profiles on their heating devices 806. Providing the heating profiles for download may help new and existing users conveniently acquire and try new heating profiles.

A heating profile may also include associated data. The associated data may include heating device information that indicates the type of heating device and/or heating unit with which the heating profile may be used. In one example, the associated data may include heating device identification numbers (e.g., model numbers) indicating the type of heating device with which the heating profile is compatible. As another example, the associated data may indicate that the heating profile should be used with a certain device/unit having a certain configuration of heating elements and/or sensors.

In some implementations, the users can store user data on the remote server 802. Example user data may include the types of conditions for which the user uses the heating device 806 along with data indicating how effective various heating profiles are in alleviating the condition. For example, the user may upload a heating profile and additional data along with the heating profile indicating the condition for which the heating profile is used and how effective the heating profile is in alleviating the condition (e.g., a score from 1-10). The remote server 802 can make recommendations to users based on uploaded user data. For example, the remote server 802 can recommend heating profiles to users with a condition if the heating profiles are indicated as effective by other users for the same/similar conditions.

FIGS. 9A-9K illustrate example GUIs that can be displayed on the user devices. Users may use the example GUIs to: 1) control the heating device, 2) transfer data to the heating device, 3) retrieve data from the heating device, 4) transfer data to the remote server, 5) retrieve data from the remote server, and perform other operations, such as creating and modifying heating profiles. In FIGS. 9A-9K, the user devices 900-1, 900-2, 900-11 include a touchscreen that overlays the GUIs. A user can interact with the GUI by interacting with the touchscreen display (e.g., touching/swiping the touchscreen display). In other implementations, a user device may include additional user inputs, such as buttons, that the user may use to control the heating device 100. The GUIs of FIGS. 9A-9K are only example GUIs used to illustrate various example features of the user device, and as such, do not represent an exhaustive set of features that may be provided by the user device.

Figure 9A:
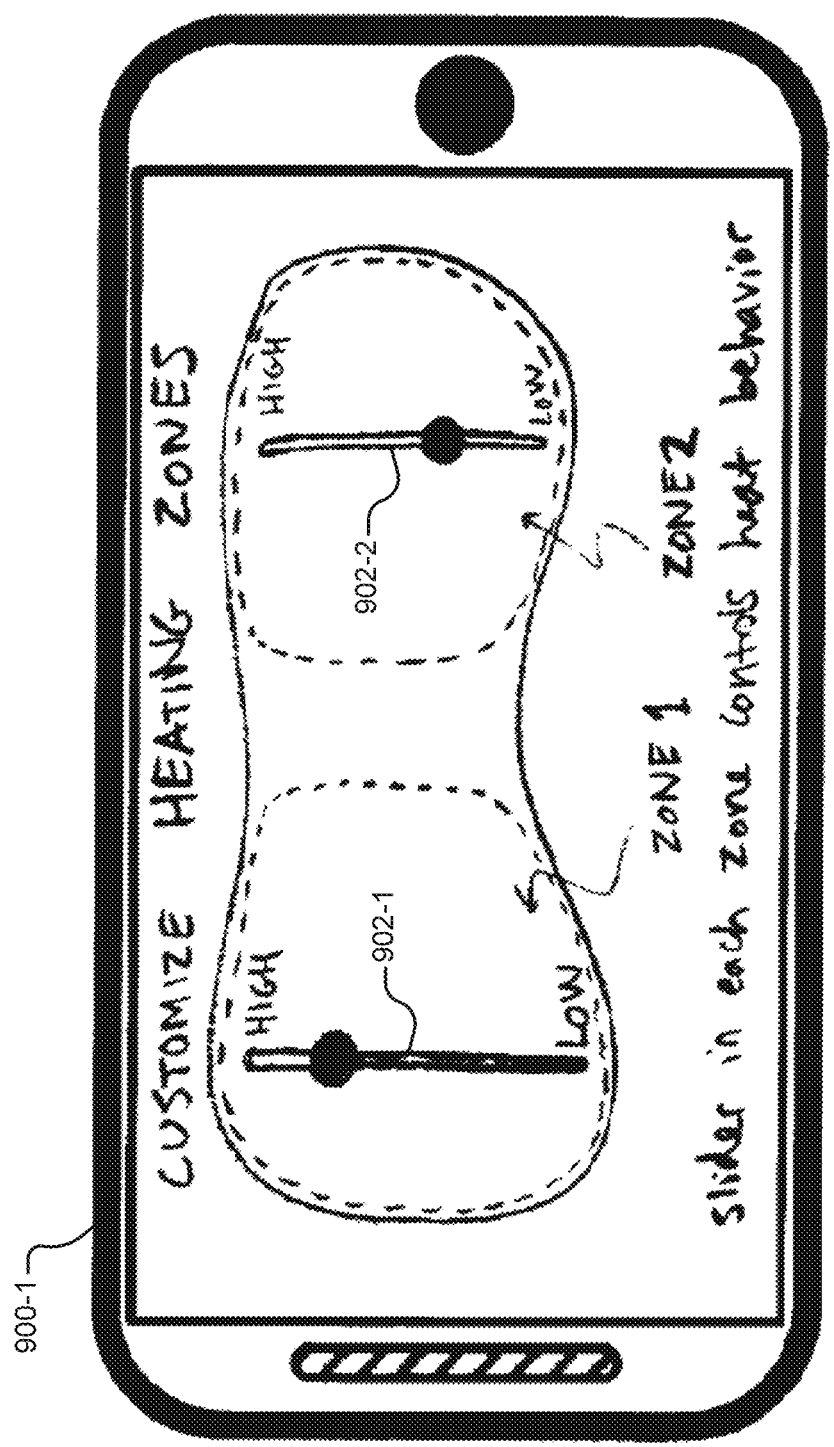
FIGS. 9A-9K illustrate example graphical user interfaces (GUIs) on a user device in communication with a heating device.

FIG. 9A illustrates a GUI that the user may use to control the heating device 100 (e.g., in the manual mode). In FIG. 9A, the GUI controls a heating device 100 having two heating zones, where each heating zone includes one or more heating elements 204. The user can interact with two different GUI elements 902-1, 902-2 (e.g., sliders), each of which controls heating to the different heating zones. For example, the user may slide (e.g., swipe) the slider icons 902-1, 902-2 in the high/low direction to increase/decrease the amount of heating in the heating zones. Although sliding GUI elements are illustrated, in other implementations, other GUI elements may be used to control heating, such as graphical buttons (e.g., +/−buttons) or dials. Although GUI elements for incrementing/decrementing heat are illustrated in FIG. 9A, other GUIs may include other controls, such as controls that control both heating zones at the same time or controls that can be used to offset the timing of different heating zones (e.g., to create a wave of heat).

Figure 9C:
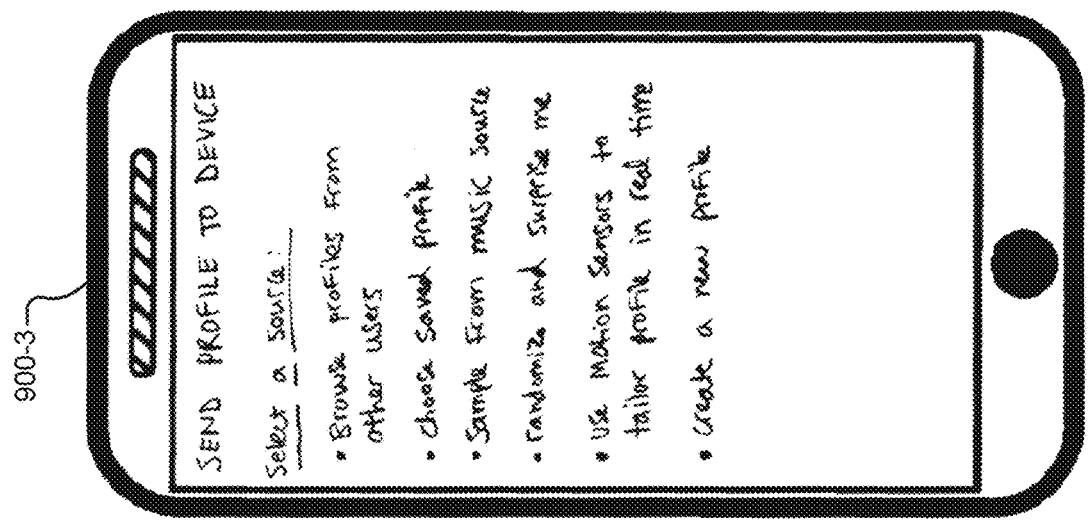
Figure 9B:
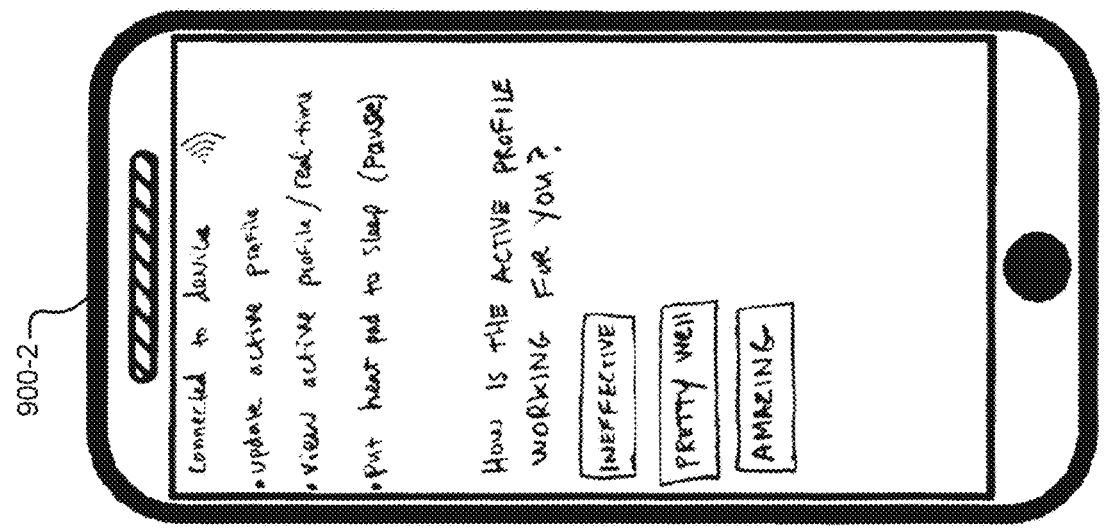

FIGS. 9B-9C illustrate GUIs that provide information to the user, provide controls for the user, and acquire feedback from the user. The GUI in FIG. 9B indicates that the user device 900-2 is connected to a heating device 100. The GUI also gives the user various controls for the heating device 100. For example, the user can: 1) update the active heating profile running on the heating device 100, 2) view the active heating profile in real-time in another GUI, and 3) put the heating device 100 to sleep. Additionally, the GUI prompts the user for feedback indicating how effective the heating profile is for the user.

FIG. 9C illustrates a GUI that allows the user to select a new heating profile to run on the heating device 100 and/or modify a current heating profile. The user can select a new heating profile from other users (e.g., from the remote server 802), select a profile saved on the user device 900-3 or remote server 802, or select a random profile. The user can also create a new profile. In some implementations, the heating profiles can be assigned names (e.g., by the user/creator) so that the user can identify the heating profile.

Additionally, the user may use motion sensors or music to generate a profile. In the case of generating profiles based on motion, the heating device 100 may detect motion patterns from the motion sensor (such as a walking motion) and/or may respond to real-time changes in the user's motion. For example, the heating device 100 may detect a regular periodic frequency within the user's motion. In response to this detected frequency, the heating device 100 can deliver pulses of heat to coincide with the user's motion. Further, in order to have the pulse of heat arrive at the user's body in-phase with his/her periodic motion, the heating device may delay/offset the pulse of heat by a given amount (based on the thermodynamic properties of the device package). In the case of generating profiles based on music, the user may choose an audio stream on the user device 900-3 (either downloaded onto the user device 900-3 or streaming on the internet). The audio stream's contents can be processed (e.g., by an external computing device and/or the heating device 100) to find underlying rhythms and frequency patterns, which can then be converted to heat delivery profiles. For example, if an audio stream has a melody that rises and falls at a given rate, then a profile can be created to match it. A benefit of using music as a seed for generating new profiles is that it allows for varied and diverse profiles without the need for a high degree of user input. Another example benefit of using music to generate profiles is that the user may listen to the music while experiencing the music-generated profile, so that the effect of the heating device 100 is combined with the effect of hearing the music stream.

Figure 9D:
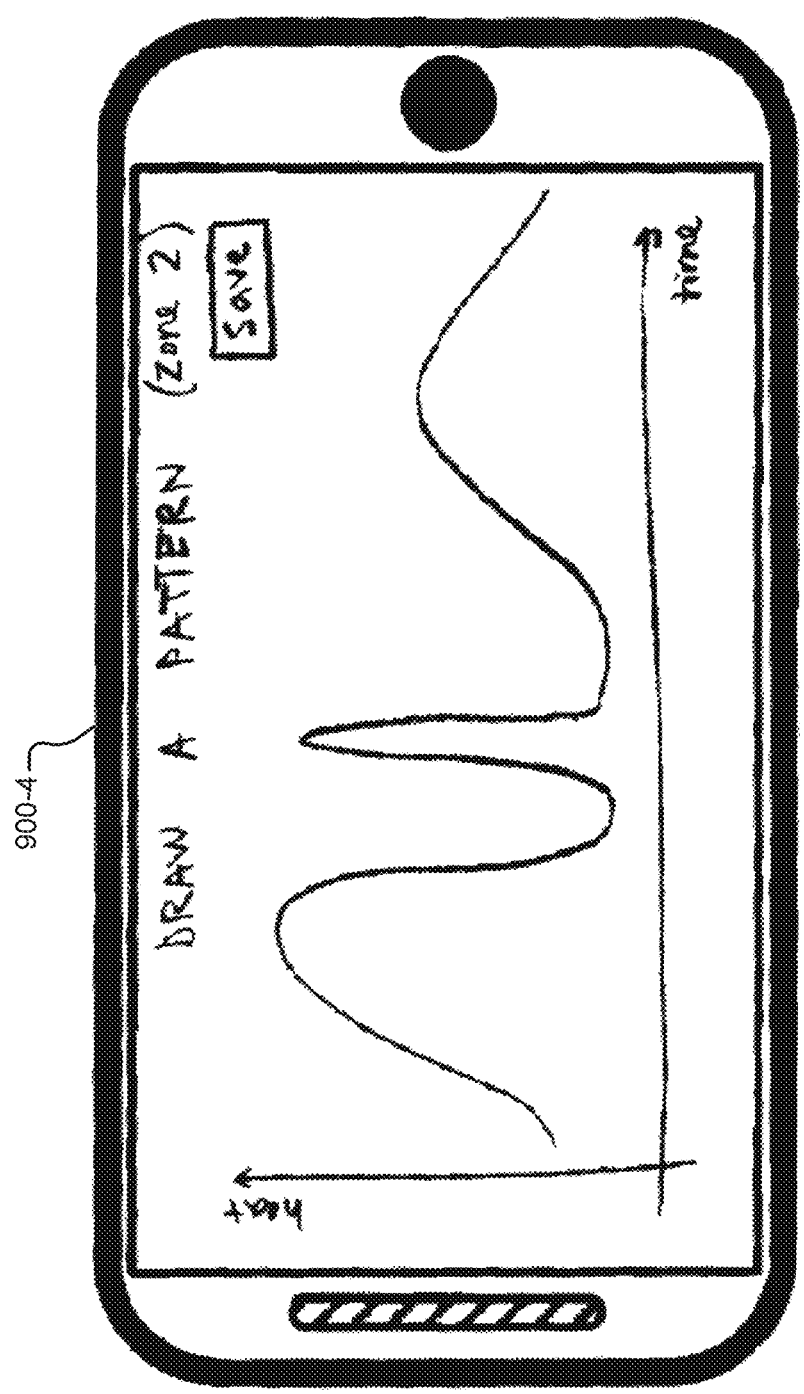

FIG. 9D illustrates a GUI that allows a user to create a custom heating profile. In the GUI, the user may draw a heating pattern (e.g., with their finger or stylus). The user may then save the heating pattern (i.e., heating profile) and upload the heating pattern to the heating device 100. The user can retrieve and modify the saved heating pattern at a later time.

Figure 9G:
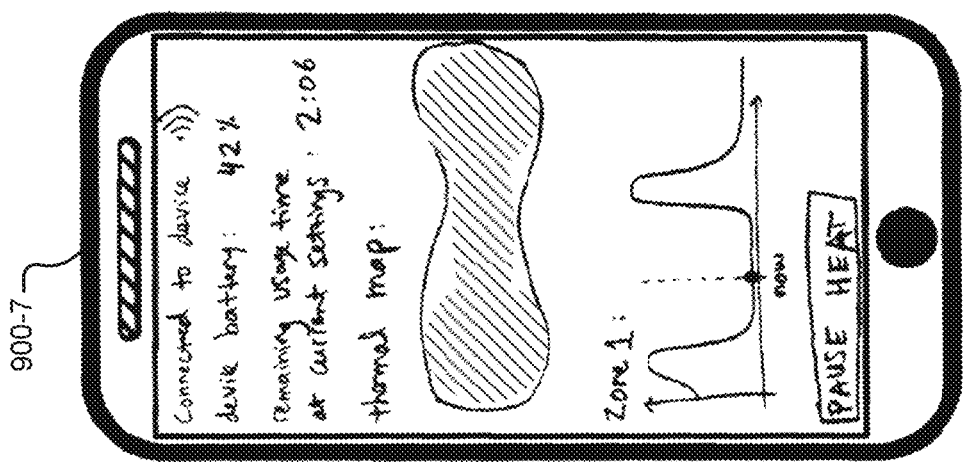
Figure 9F:
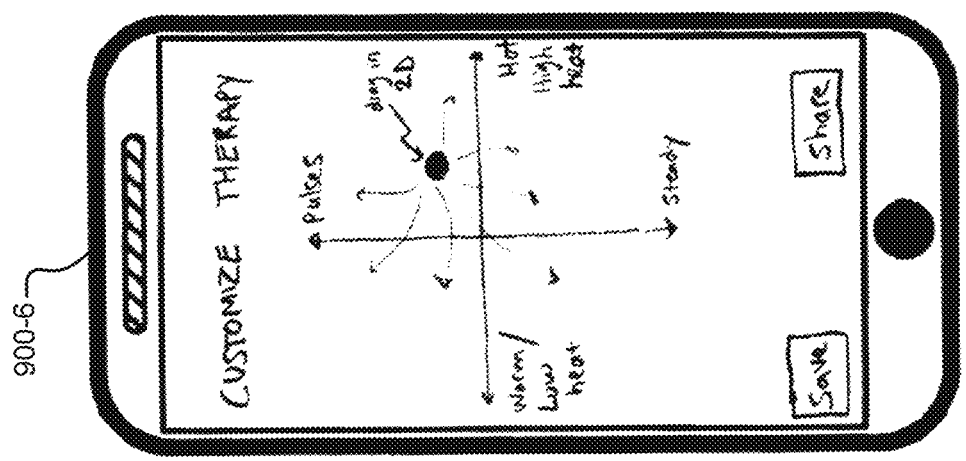
Figure 9E:
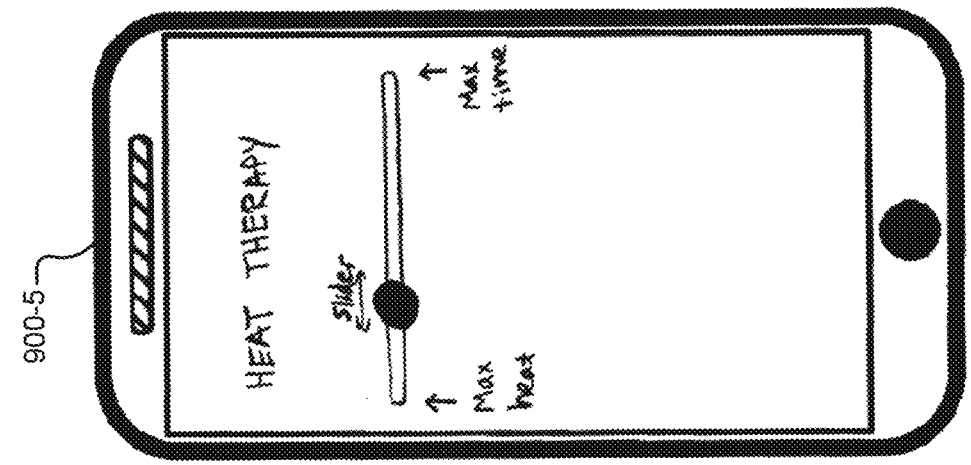

FIGS. 9E-9F illustrate GUIs that allow a user to specify their desires for a heating profile, which may then be generated automatically by the user devices 900-5, 900-6. In FIG. 9E, the user can adjust a slider left or right to indicate that they would like maximum heat or maximum heating device operating time. In general, a greater amount of heat may yield a shorter operating time when the heating device 100 is running on a battery. The GUI provides the user with the choice of whether to increase heat or increase operating time. The heating device 100 may adjust the amplitude of the current heating pattern according to the user's selection and/or select another heating pattern based on the selected operating time and/or heating.

The GUI of FIG. 9F illustrates a graph with four quadrants and a point that the user may position within the quadrants to control the intensity of heat and whether the heating is steady or in pulses. The user may drag the dot in the X direction to increase/decrease the amount of heat delivered to the user. The user may drag the dot in the Y direction to modify the rate of pulses delivered to the user. For example, dragging the dot toward the pulses portion of the Y axis may cause an increase in pulse frequency, whereas dragging the dot toward the steady portion of the Y axis may cause the pulse frequency to decrease (e.g., steady=no pulses).

FIG. 9G illustrates a GUI that conveys heating device information to the user, including: 1) the connection status between the user device 900-7 and the heating device, 2) the battery status of the heating device, and 3) the remaining operating time for the heating device at the current settings (e.g., the current heating profile). The GUI also illustrates a thermal map of the heating device that indicates the heat in different heating zones. Additionally, the GUI illustrates the heating profile running in zone 1 of the heating device. Over time, the illustrated heating profile may scroll from left to right as the heating device executes the heating profile. This allows the user to visualize the past/present/future behavior of the heating profile. The user may pause the heating device by pressing the "PAUSE HEAT" button in the GUI.

Figure 9J:
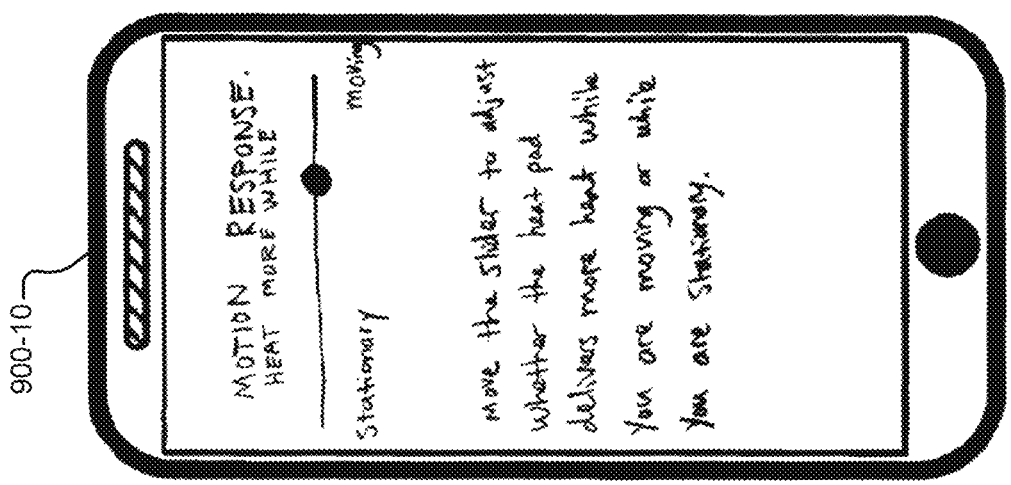
Figure 9I:
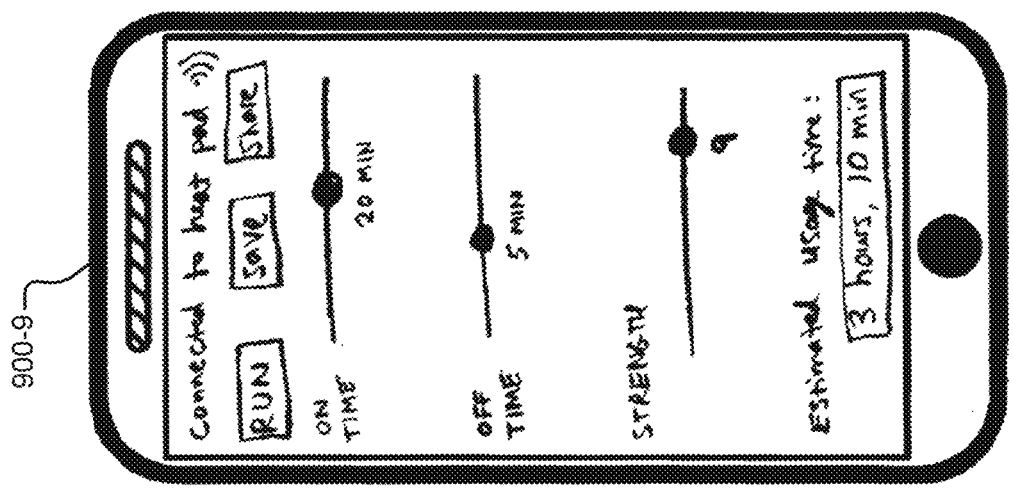
Figure 9H:
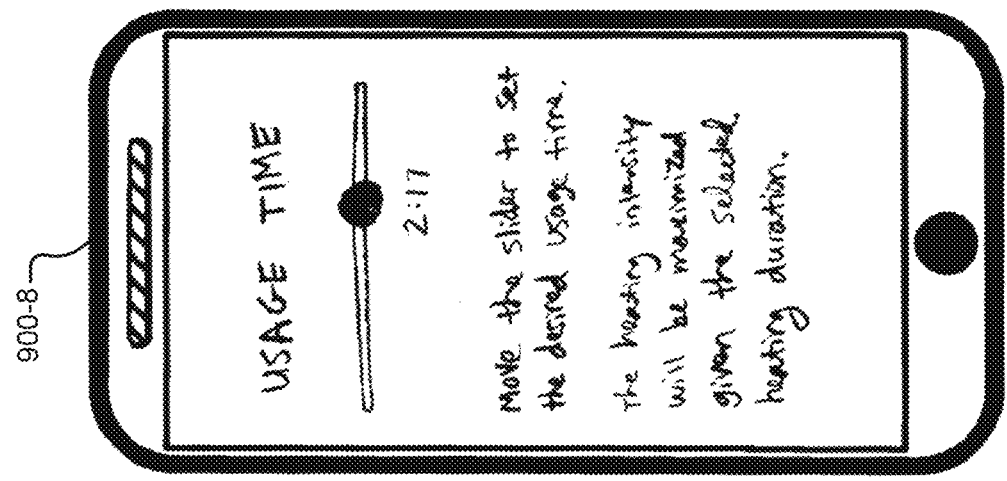

FIG. 9H illustrates a GUI that allows the user to select a desired usage (operation) time for the heating device 100. For example, the user may slide the slider to the right/left to increase/decrease the usage time. The user device 900-8 and/or the heating device 100 may then update the current heating profile or generate a new heating profile based on the selected usage time.

FIG. 9I illustrates a GUI that allows the user to control how long a heating profile is run, how long a heating profile is turned off, and the strength of the heating profile. For example, the user may use a slider GUI element to set an on time that sets how long the heating profile should run. The user may also use a slider GUI element to set an off time that sets how long the heating device 100 should cease heating (e.g., pause) after running for the on time. The heating device 100 may then repeat the on/off behavior for the selected on/off times. The user can use a slider GUI element to set the strength (e.g., the power) associated with the heating profile, where a greater strength may increase the power delivery for a given heating profile. The user device 900-9 may then calculate the estimated usage time for the heating device 100 according to the present battery level, the on/off times, and the strength. The GUI displays the estimated usage time to the user (e.g., 3 hours, 10 min). Modifying the on time and off time can extend/reduce the battery life (i.e., the estimated usage time) of the heating device 100.

FIG. 9J illustrates a GUI that allows a user to tailor the motion response of the heating device 100. As described herein, the heating device 100 can determine the motion of the user based on a motion sensor included in the heating device 100 and/or a motion sensor included in the user device 900-10. The user may move the slider GUI element to the left or right to adjust whether the heating device 100 provides more heat while the user is stationary or moving.

Figure 9K:
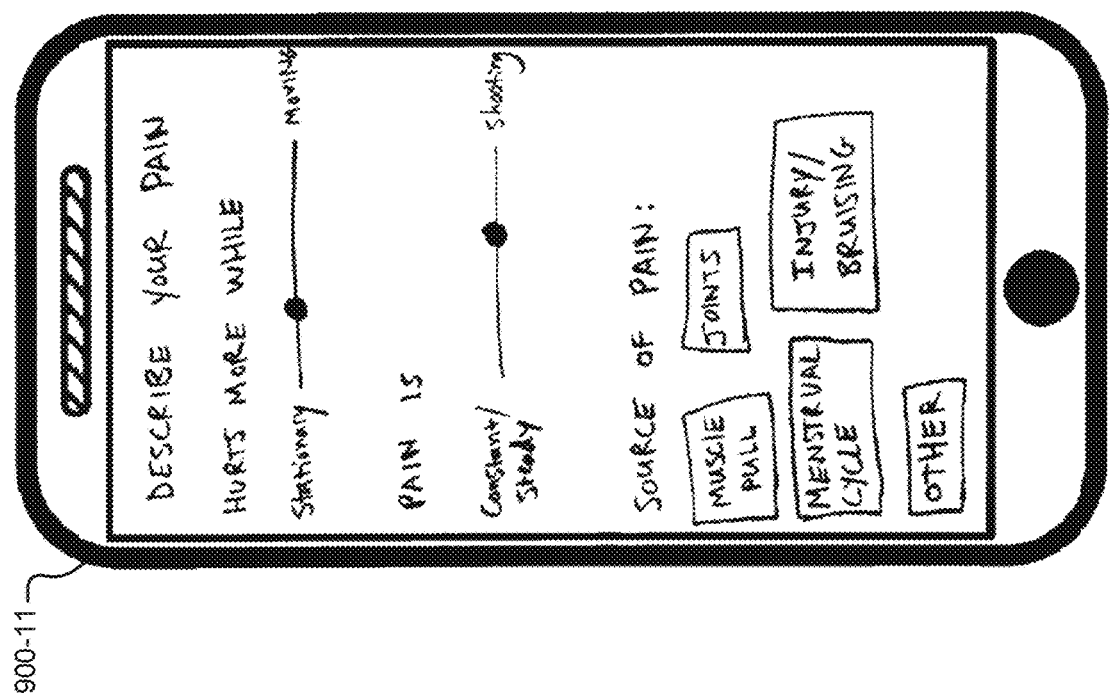

FIG. 9K illustrates a GUI that acquires user information. The GUI prompts the user to describe their pain based on whether the user is stationary/moving. The GUI also prompts the user to describe their pain in terms of whether it is consistent/steady or shooting. Additionally, the GUI prompts the user to indicate their source of pain. The user information acquired via the GUI may be stored on the user device 900-11 and/or the remote server 802. At a later time, the user may indicate which heating profile(s) are most effective in comforting the pain described in the GUI. The effectiveness of one or more heating profiles with respect to the reduction/elimination of pain described in the GUI may be stored at the remote server 802 and/or user device 900-11 and be used to make recommendations to the user or other users, as described herein.

The heating device 100 can include a device package that can house one or more heating units 202, device electronics 300, and other components (e.g., a battery). The device package may include flexible portions that conform to a user's body. FIGS. 1A-1C and 11A-15B illustrate different example heating devices having different packages.

Figure 10A:
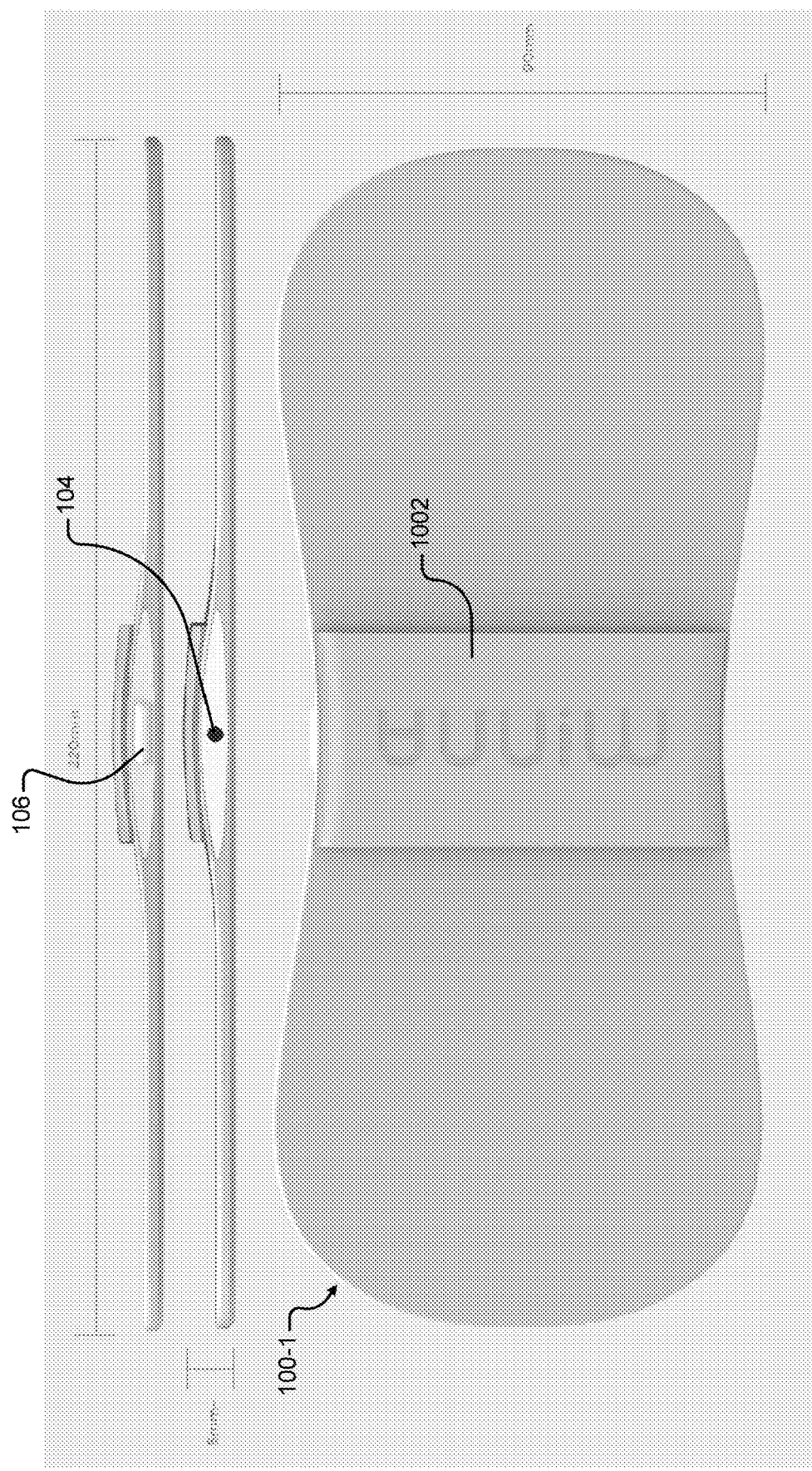
FIGS. 10A-15 illustrate additional example heating devices.

FIGS. 1A-1C and FIGS. 10A-10D illustrate a first heating device 100-1. The first heating device package can include one or more heating elements 204 arranged in any manner throughout the package. The first heating device 100-1 can be applied to different parts of the user's body, such as the user's back (FIG. 1C). The first device package can include one or more belt loops 1002 that receive a belt 1004 used to hold the heating device 100-1 to a user's body. The belt 1004 is fastened together using a clasp 1005. With respect to FIG. 10A, the first heating device 100-1 can include a user input button 106 (e.g., an on/off button) and a power input port 104. In FIG. 10A, the first heating device 100-1 may have approximate dimensions of 220 mm by 90 mm, with an approximate thickness of 5 mm. Note that the dimensions included in the figures for the various heating devices 100 are only example dimensions. Heating devices having other dimensions may be fabricated.

Figure 10B:
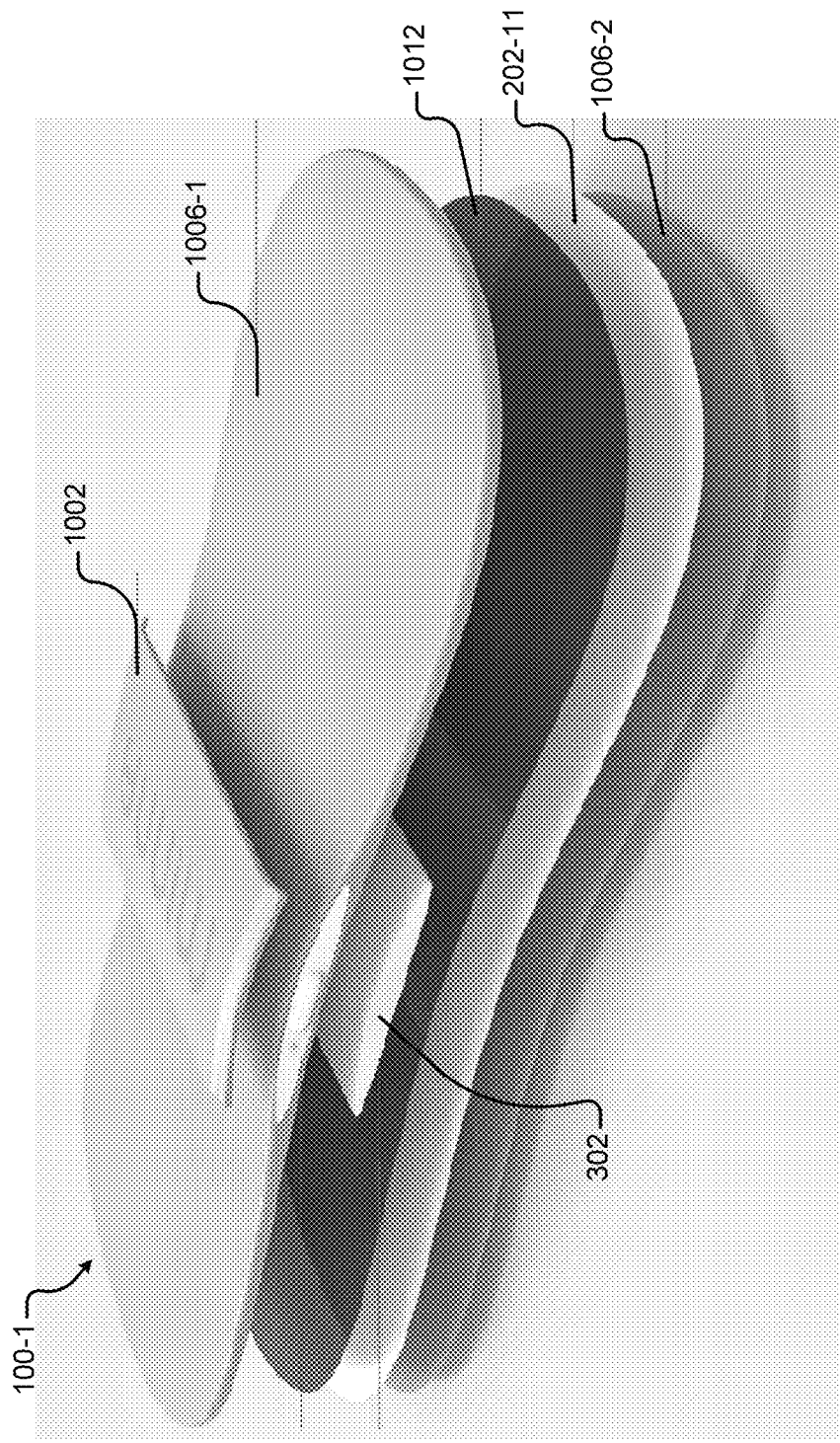
Figure 10C:
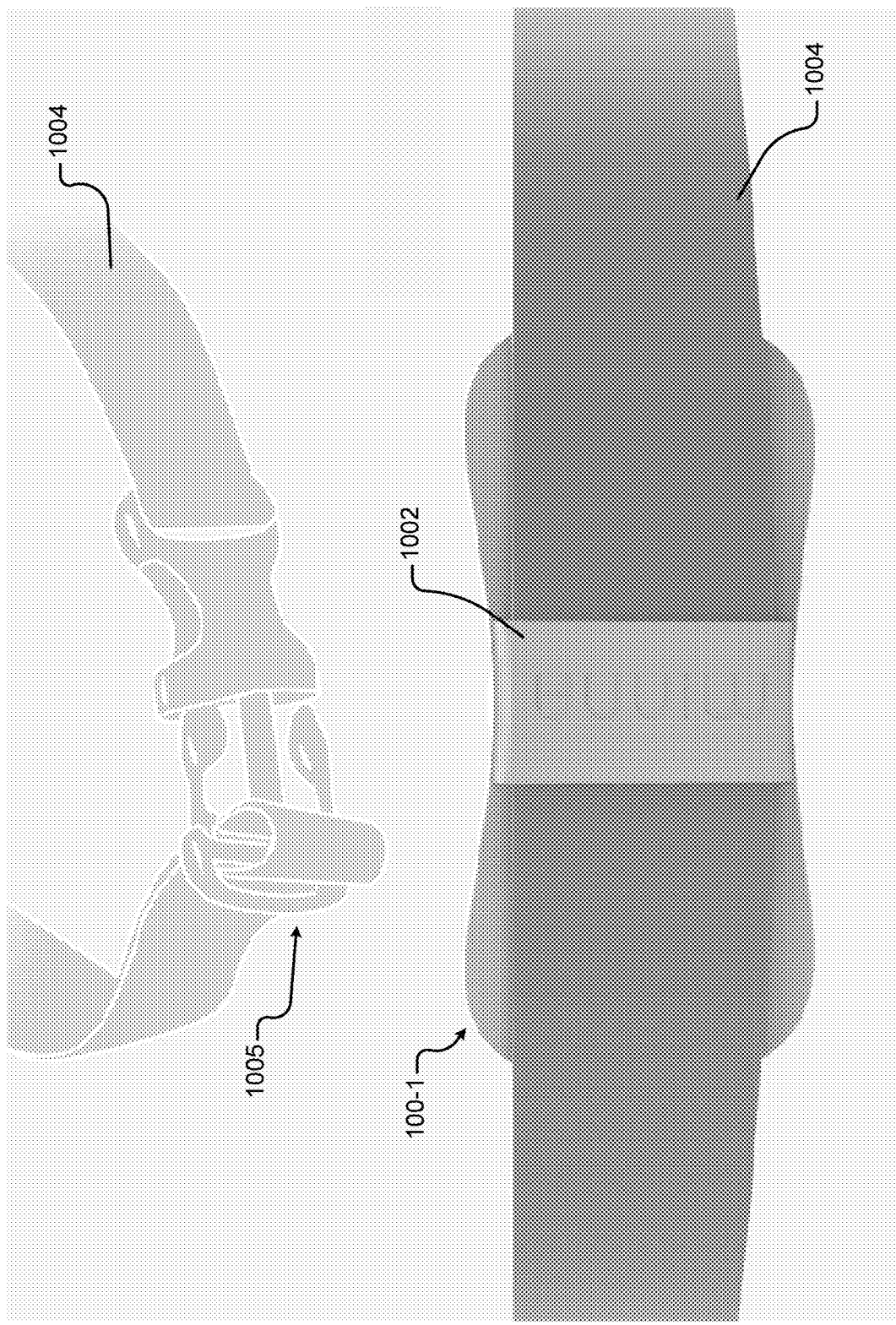
Figure 10D:
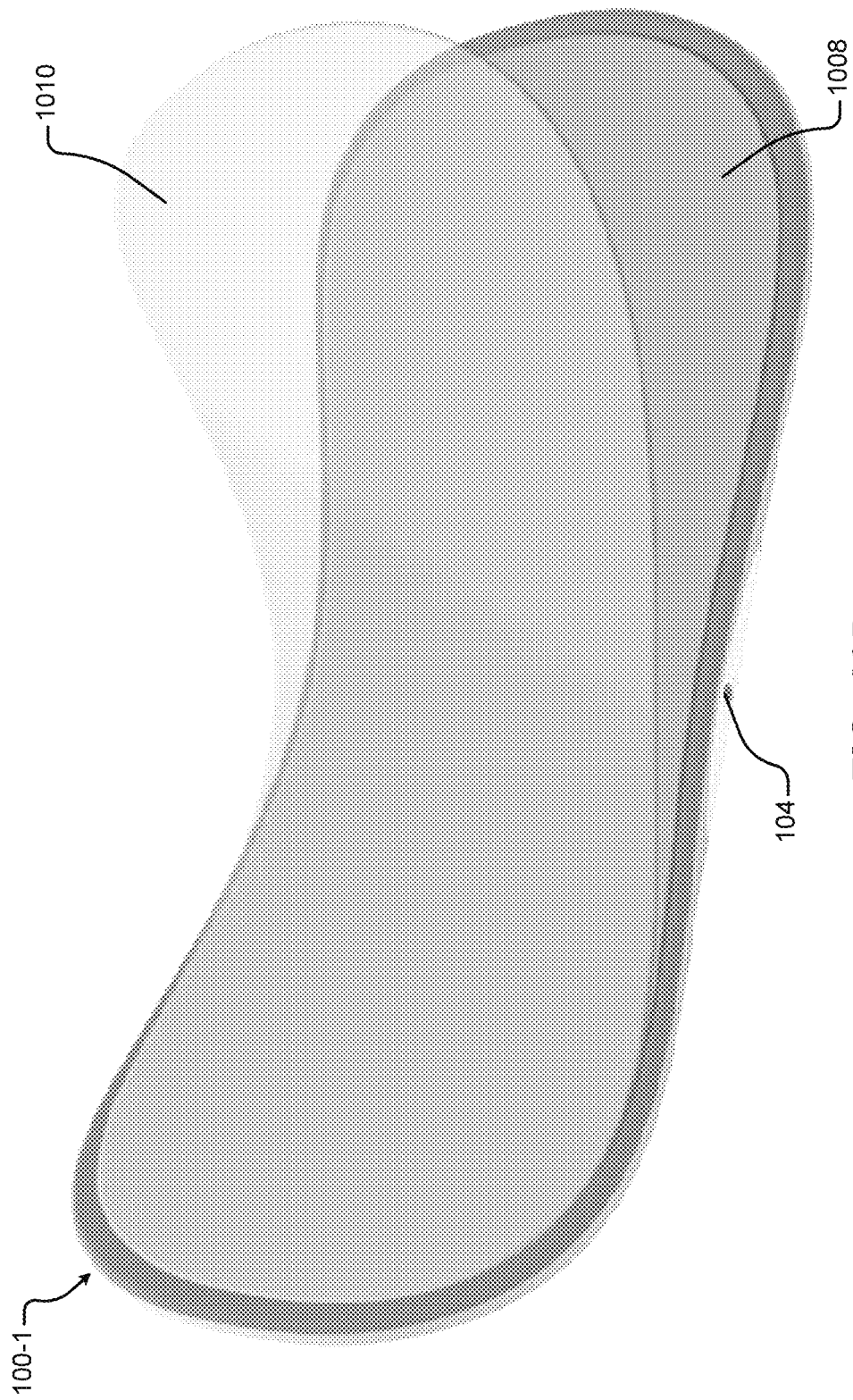

FIG. 10B illustrates an exploded view of the first heating device 100-1. The first heating device 100-1 includes an encapsulation 1006. The encapsulation 1006 is formed from an encapsulation top cover 1006-1 and an encapsulation bottom cover 1006-2. The encapsulation 1006 encapsulates components of the heating device 100-1, such as the heating unit 202-11, battery 302, and device electronics (not illustrated in FIG. 10B). The top/bottom covers 1006 in FIG. 10B can be flexible material that can be adhered together or connected in another manner, such as fused, vulcanized, ultrasonically welded, or thermally welded. In some implementations, the encapsulation 1006 may not entirely cover the heating unit 202-11. In these implementations, the heating unit 202-11, or other body contact layer (e.g., a thermally conductive layer) may contact the user (e.g., body or clothing). The encapsulation 1006 may be formed from materials including, but not limited to, cloth-based or fabric materials, molded flexible plastics/rubbers, foams, and synthetic fleece material. In some implementations, the heating device 100-1 may include material/structure that imparts some rigidity to the heating device 100-1. FIG. 10D illustrates an additional skin adhesive layer 1008 that may be attached to the encapsulation bottom cover 1006-2. A removable cover layer 1010 can be peeled from the adhesive layer 1008 to expose the adhesive layer 1008.

The first heating device 100-1 includes an insulation layer 1012 (e.g., an insulating foam) that may help increase the thermal efficiency of the heating device 100-1. The insulation layer 1012 may minimize heat flowing away from the body and away from the heating device 100-1. The insulation layer 1012 may include a thermally insulating material, such as a closed cell foam. In some implementations, the insulation layer 1012 may include material that reflects heat back toward the body. The insulation layer 1012 may also provide comfort to the user. For example, the insulation layer 1012 may include a material (e.g., a foam) that may provide a cushioning layer that conforms to the user's body and other components of the heating device 100-1. The insulation layer 1012 may rebound after conforming during use.

FIGS. 11A-11F illustrate a second example heating device 100-2. The heating device 100-2 includes a heating unit 202-12. The heating unit 202-12 includes a substrate and one or more heating elements (not illustrated) embedded within the substrate. For example, the heating elements may be resistive heating elements embedded within a polymer substrate. In a more specific example, the heating unit may be a flexible circuit board including resistive heating traces. The heating elements of the heating device 100-2 may be arranged in any manner described herein.

The heating device 100-2 includes a removable battery housing 1100. The battery housing 1100 includes a battery (not shown). In some implementations, the battery housing 1100 may also include device electronics. Accordingly, the battery housing 1100 may also be referred to as a "battery and electronics housing 1100." The user may remove/replace the battery housing 1100. For example, the user may replace the battery housing 1100 with other battery housings including fully charged batteries and/or batteries with different capacities. In some implementations, the battery housing 1100 may have a different geometry than that illustrated in FIGS. 11A-11F. For example, a battery housing including a battery with a larger capacity may have a larger volume and/or different shape than that illustrated in FIGS. 11A-11F.

Figure 11A:
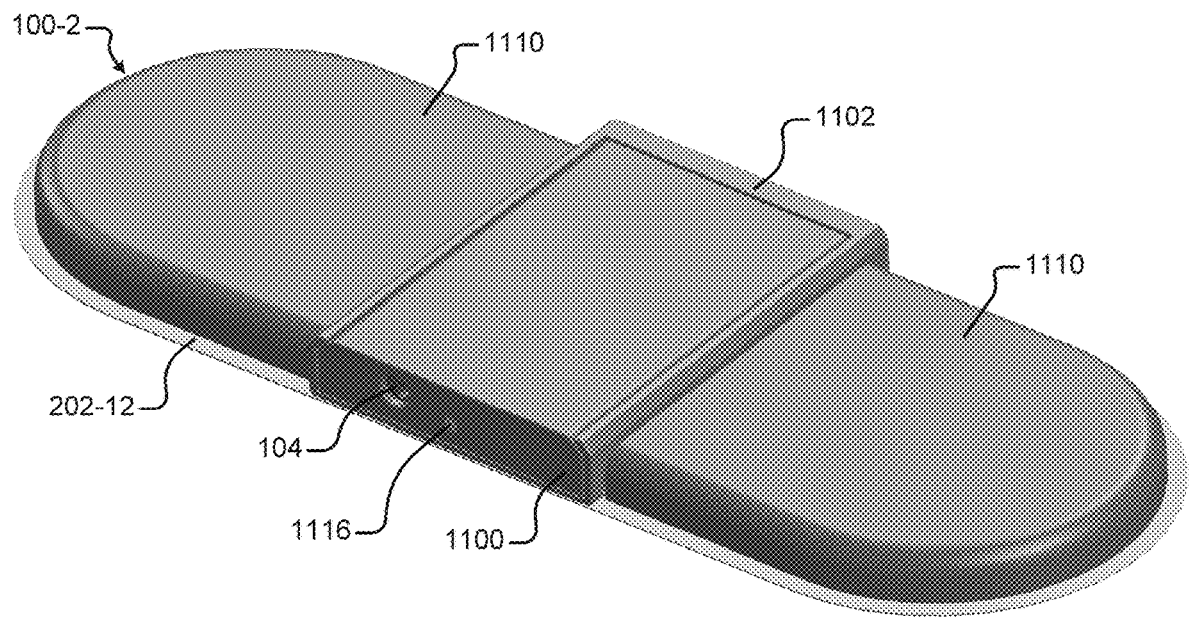
Figure 11B:
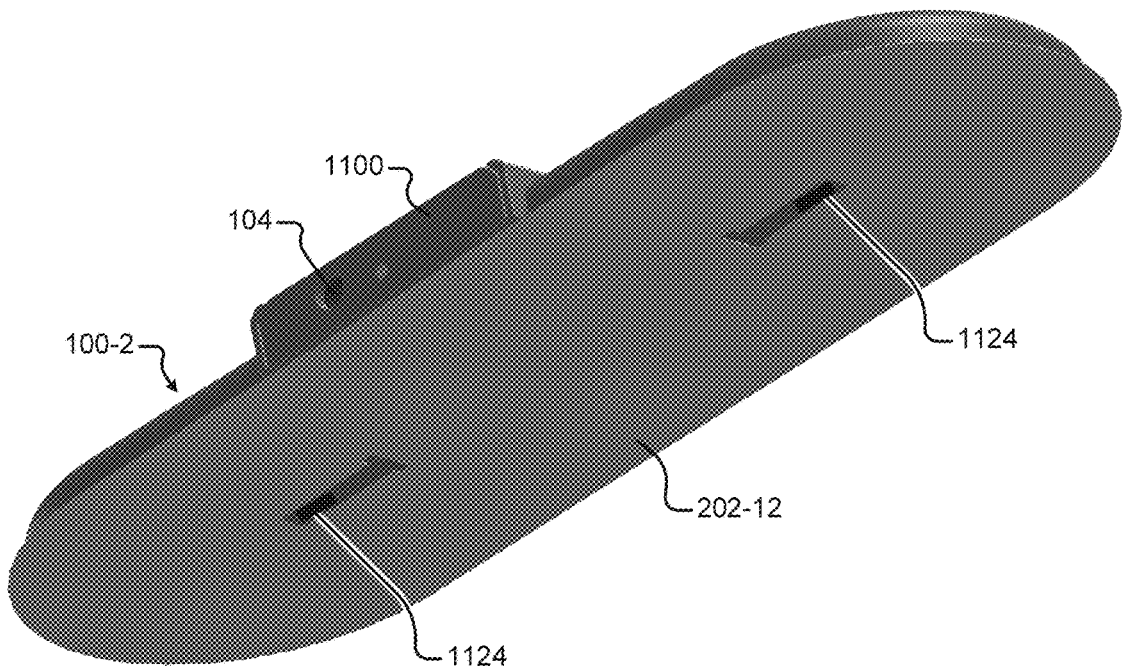
Figure 11C:
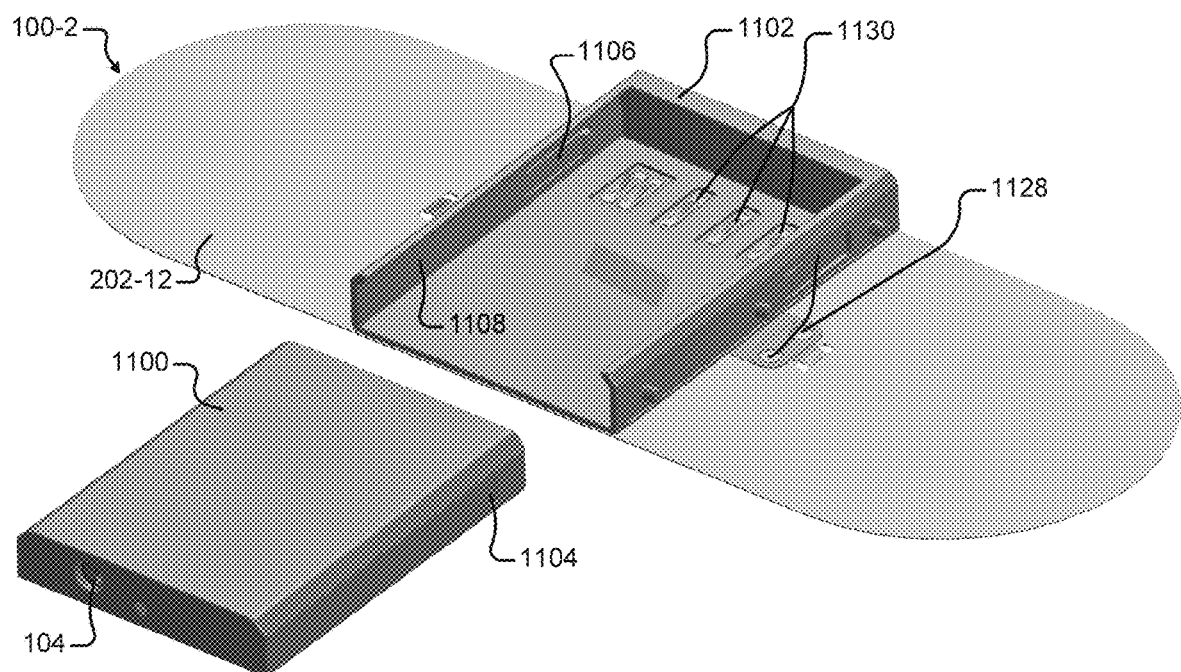
Figure 11D:
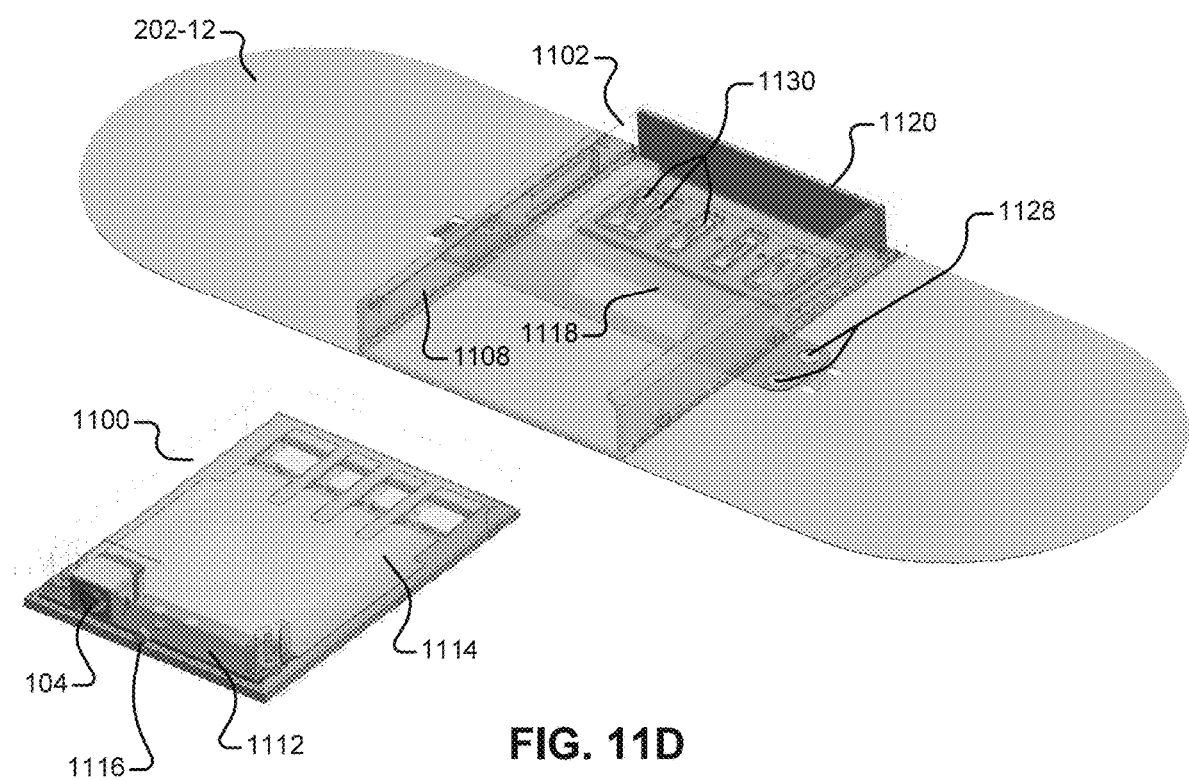
Figure 11E:
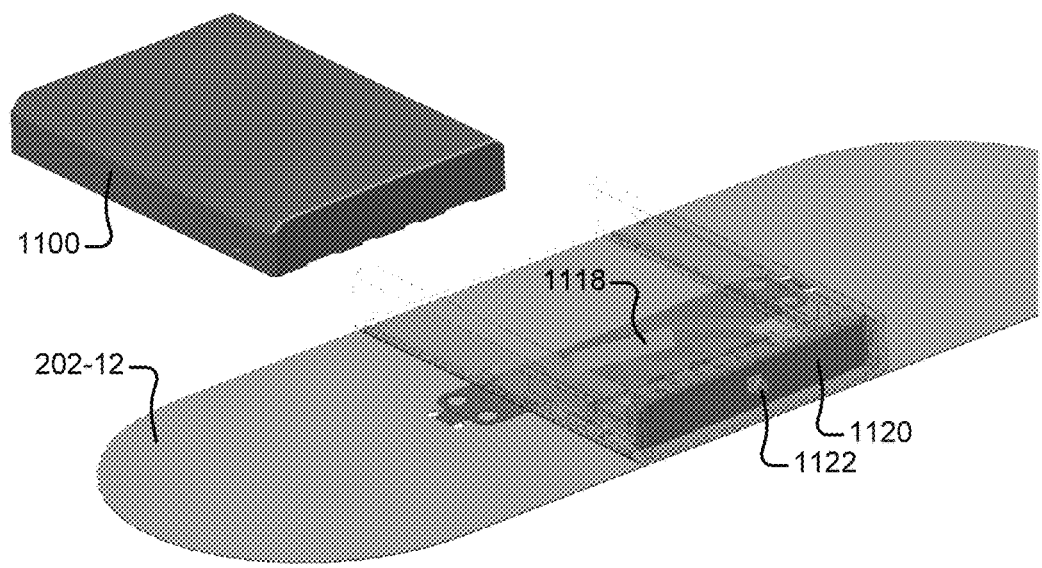
Figure 11F:
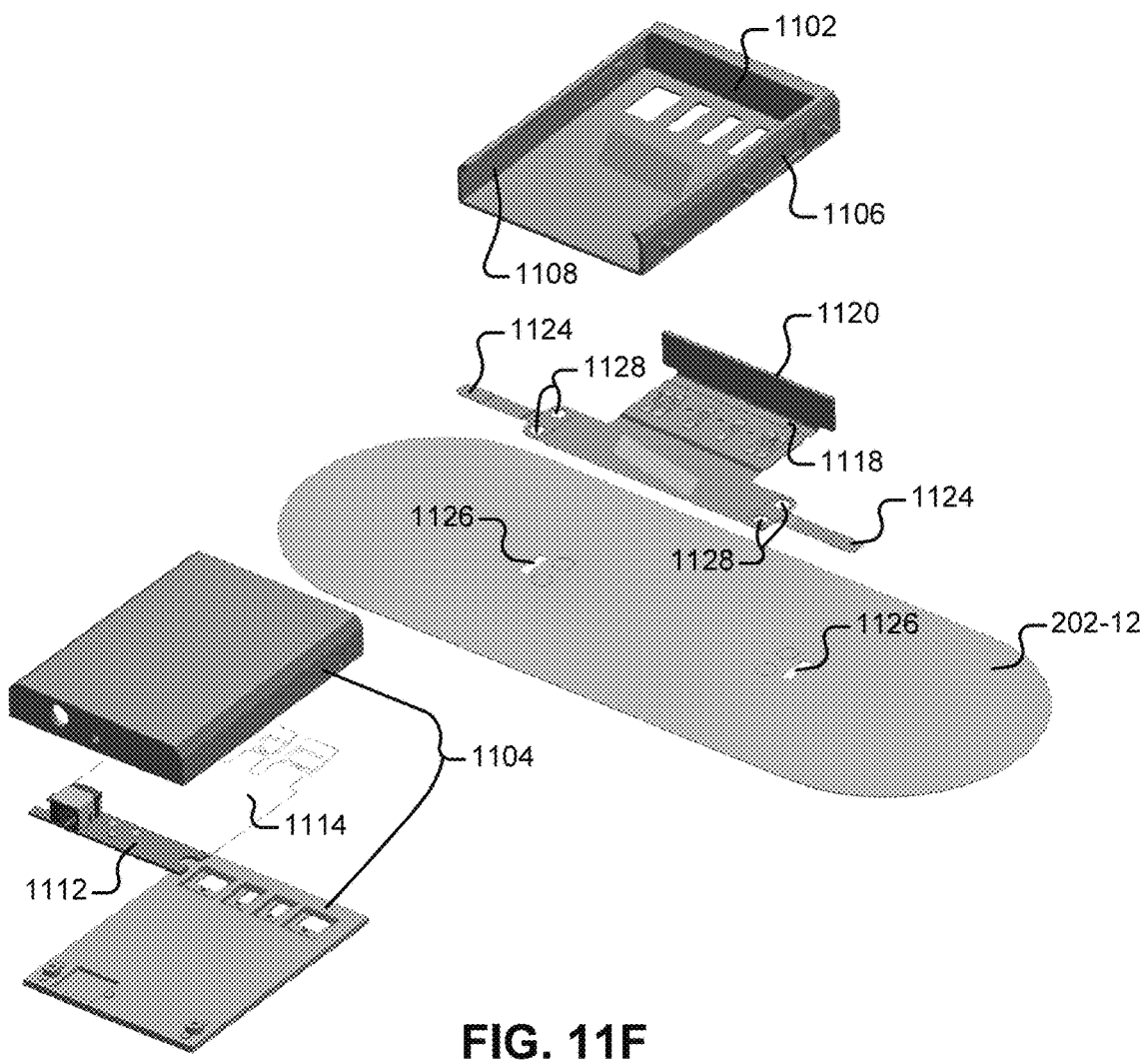

The battery housing 1100 mates with a receptacle 1102. In the example of FIG. 11C, the battery housing 1100 defines indentations 1104 that mate with retention clips 1106 included on the receptacle 1102. The user can slide the battery housing 1100 into the receptacle 1102 along rails 1108 defined by the receptacle. The battery housing 1100 is seated and retained in position by the mating between the retention clips 1106 and indentations 1104. When the battery housing 1100 is seated in the receptacle 1102, the user can apply a force to the battery housing 1100 to unseat the battery housing 1100 from the receptacle 1102. For example, the user can apply a force to the battery housing 1100 that causes the indentations 1104 to spread the retention clips 1106 and then causes the battery housing 1100 to slide out of the receptacle 1102 along the rails 1108. The illustrated battery housing 1100 and receptacle 1102 are only one example retention mechanism for a removable battery housing. The battery housing may be attached and retained by other retention mechanisms, such as an electrical connector (e.g., friction between electrical contacts), a magnetic latch, a push/push mechanism (e.g., such as on a ballpoint pen), and/or a mechanical hook/latch (e.g., a user actuated connector).

The heating device 100-2 includes an insulating foam padding 1110. The insulating foam 1110 may be formed from a flexible insulating material, such as a closed cell foam. The insulating foam 1110 is attached to the heating unit 202-12 on the side of the heating unit 202-12 facing away from the user's body during use. The insulating foam 1110 may increase the thermal efficiency of the heating device 100-2 by minimizing heat flowing away from the body. The insulating foam 1110 may also provide comfort to the user during use. For example, the insulating foam 1110 may even out the pressure against the user if the heating device 100-2 is sandwiched between the user and an object (e.g., a chair back). Specifically, in FIG. 11A, the insulating foam 1110 can help distribute pressure along the entire heating unit 202-12, which may otherwise be focused under the battery housing 1100 and receptacle 1102.

The heating device 100-2 includes multiple flexible and rigid PCBs. With respect to FIG. 11D and FIG. 11F, the battery housing 1100 includes a first rigid PCB 1112 and a first flexible PCB 1114 that are connected to one another. The first rigid PCB 1112 includes a power input port 104 and a battery indicator 1116. The battery indicator 1116 may indicate a variety of statuses associated with the battery, such as the charge level of the battery and whether the battery is being charged. The first flexible PCB 1114 includes electrical traces that connect the battery to the electronics included on the first rigid PCB 1112. The first flexible PCB 1114 also includes electrical traces that connect to the electrical contacts on the second flexible PCB 1118 (e.g., FIG. 11D). The first rigid PCB 1112, the first flexible PCB 1114, and/or the battery may also include circuits similar to those included in the power module 408 of FIG. 4.

The heating device 100-2 includes a second rigid PCB 1120 and a second flexible PCB 1118 that are connected to one another. The second rigid PCB 1120 includes device electronics described herein, such as electronics included in the communication module 404, processing module 402, memory 420, temperature sensing module 412, heating control module 410, and interface module 406. The LED on the heating device 1122 may indicate if the heating device 100-2 is turned on, if it is connected to a user device 102 (e.g., via Bluetooth), if it is heating, and/or the state of the battery.

The second flexible PCB 1118 can be attached to the heating unit 202-12 in a variety of ways. For example, the second flexible PCB 1118 can be bonded to the heating unit 202-12 using adhesive bonding, heat welding, ultrasonic welding, mechanical attachments, or other technique. The second flexible PCB 1118 includes temperature sensors 1124 that extend through openings 1126 defined in the heating unit 202-12. The temperature sensors 1126 are positioned between the heating unit 202-12 and the user during use. The second flexible PCB 1118 also includes electrical contacts 1128 that solder to the heating elements included in the heating unit 202-12.

The second flexible PCB 1118 includes electrical contacts 1130 (e.g., 6 illustrated contacts) that electrically couple the battery and electronics included in the battery housing 1100 to the device electronics included on the second flexible PCB 1118 and the second rigid PCB 1120. For example, the contacts 1130 may deliver power from the battery to the second flexible PCB 1118 and the second rigid PCB 1120. The electrical contacts 1130 may also provide for communication between components included in the battery housing 1100 and components on the receptacle side of the heating device 100-2. For example, the contacts 1130 may allow electronics on the second rigid PCB 1120 to determine the battery serial number/ID, the battery size, the state of charge, the battery temperature, the battery usage time, and other data.

The arrangement of PCBs and device electronics described with respect to FIGS. 11A-11F is only one example arrangement of PCBs and device electronics. In other examples, the heating device 100-2 may include other arrangements of PCBs and device electronics. For example, the heating device 100-2 may include other arrangements of flexible and/or rigid PCBs. As another example, the battery housing 1100 may include additional device electronics, such as device electronics included in the communication module 404, processing module 402, memory 420, temperature sensing module 412, heating control module 410, and interface module 406.

Note that the heating device 100-2 does not include a manual user input button. For example, the heating device 100-2 does not include an on/off button for turning the heating device 100-2 on/off. Instead of controlling the heating device 100-2 using manual buttons included on the heating device 100-2, the user may control the heating device 100-2 via the user device 102. For example, the user may interact with a GUI on the user device 102 to turn the heating device 100-2 on/off or place the heating device in a standby/sleep mode.

Figure 12A:
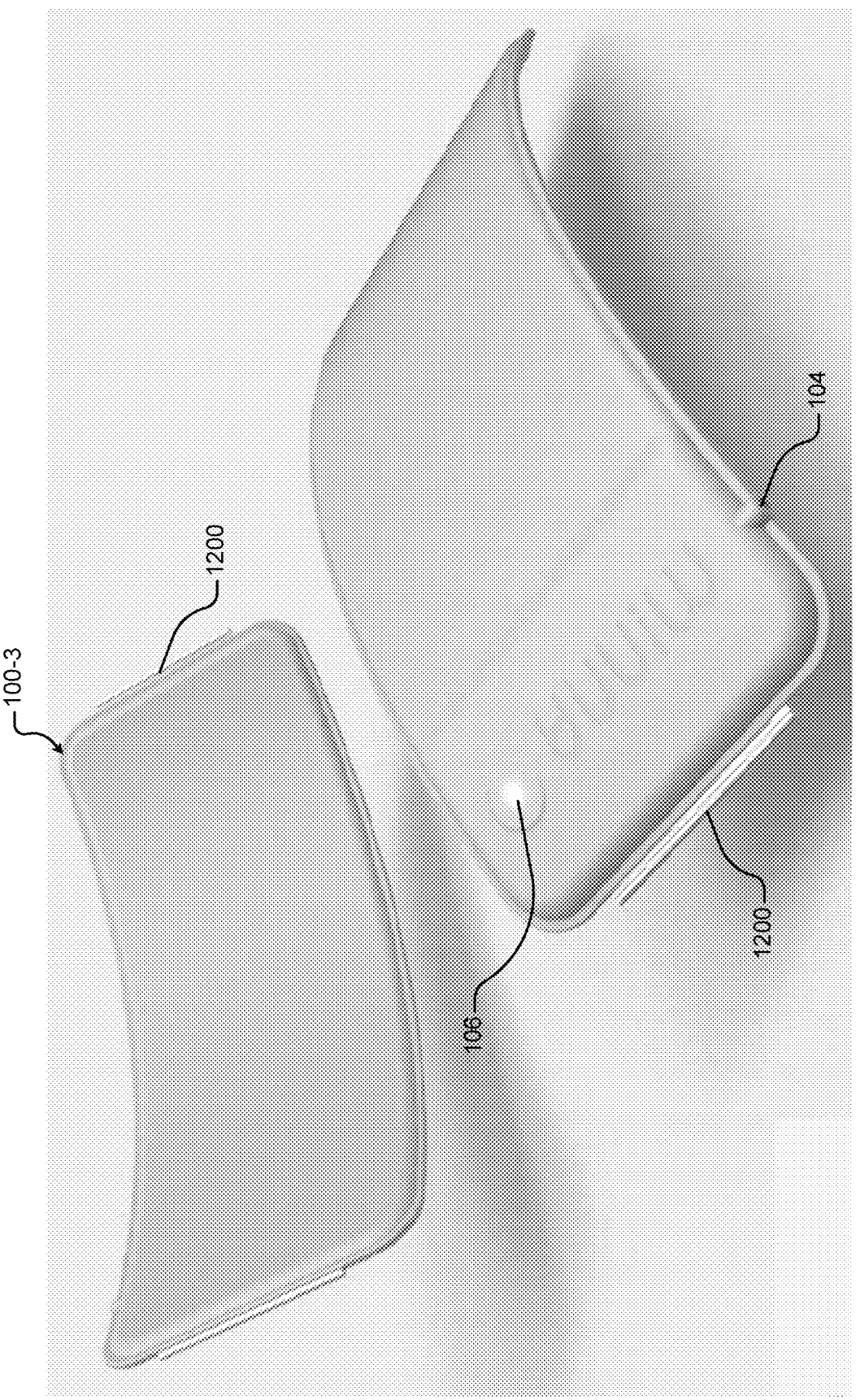
Figure 12B:
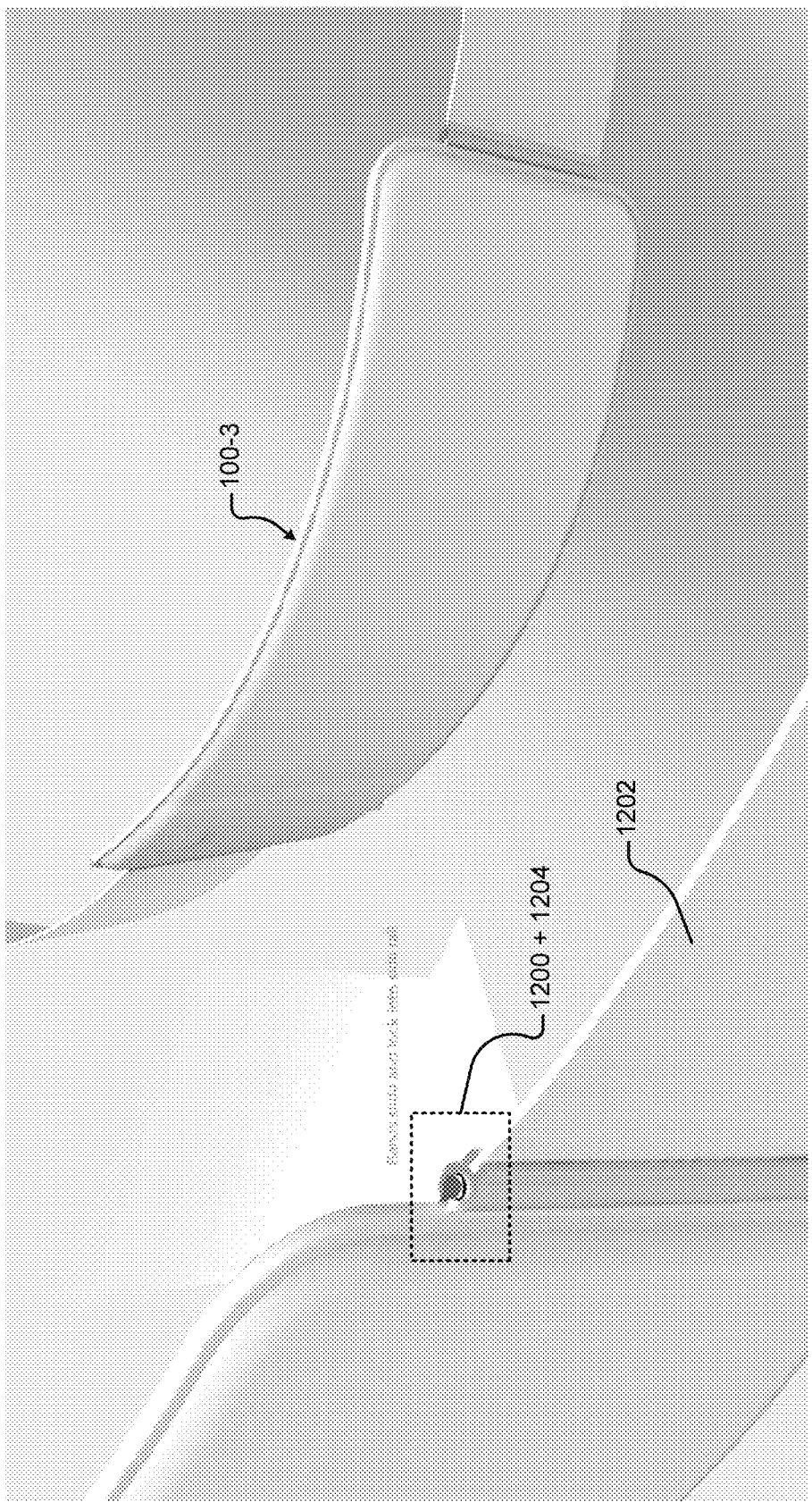
Figure 12C:
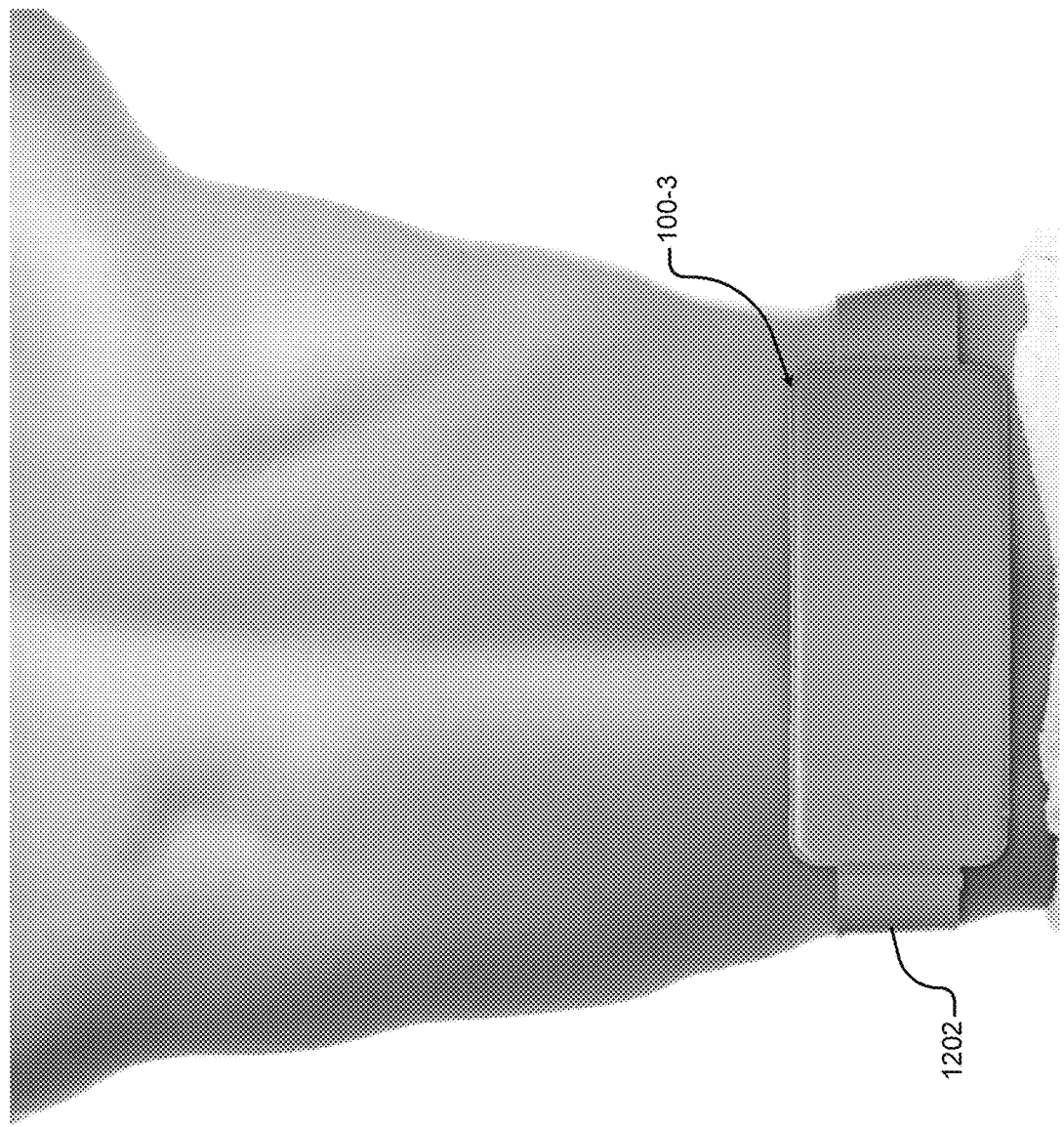

FIGS. 12A-12C illustrate a third heating device 100-3. The third heating device package can include one or more heating elements 204 arranged in any manner throughout the package. The third heating device 100-3 can be applied to different parts of the user's body, such as the user's back (FIG. 12C). The third device package can include one or more connectors 1200 (device connectors) that are configured to connect to a belt loop 1202 having connectors 1204 (belt connectors) that mate with the device connectors 1200 of the third device package (see FIG. 12B). With respect to FIG. 12A, the third heating device 100-3 can include a user input button 106 (e.g., an on/off button) and a power input port 104. The third heating device 100-3 may have approximate dimensions of 220 mm by 90 mm, with a thickness of approximately 5 mm.

The third heating device 100-3 of FIGS. 12A-12C may include similar layers as the first heating device 100-1, such as the encapsulation layers, heating unit, and insulation layer. The arrangement of the components within the third heating device 100-3 may be different than the arrangement of components within the first heating device 100-1. For example, the battery, user input button, and power input port of the third heating device 100-3 may be offset to one side, whereas these components are centrally located in the first heating device 100-1. In some implementations, the third heating device 100-3 may also include an adhesive layer (not illustrated) that may be attached to the encapsulation bottom cover.

Figure 13A:
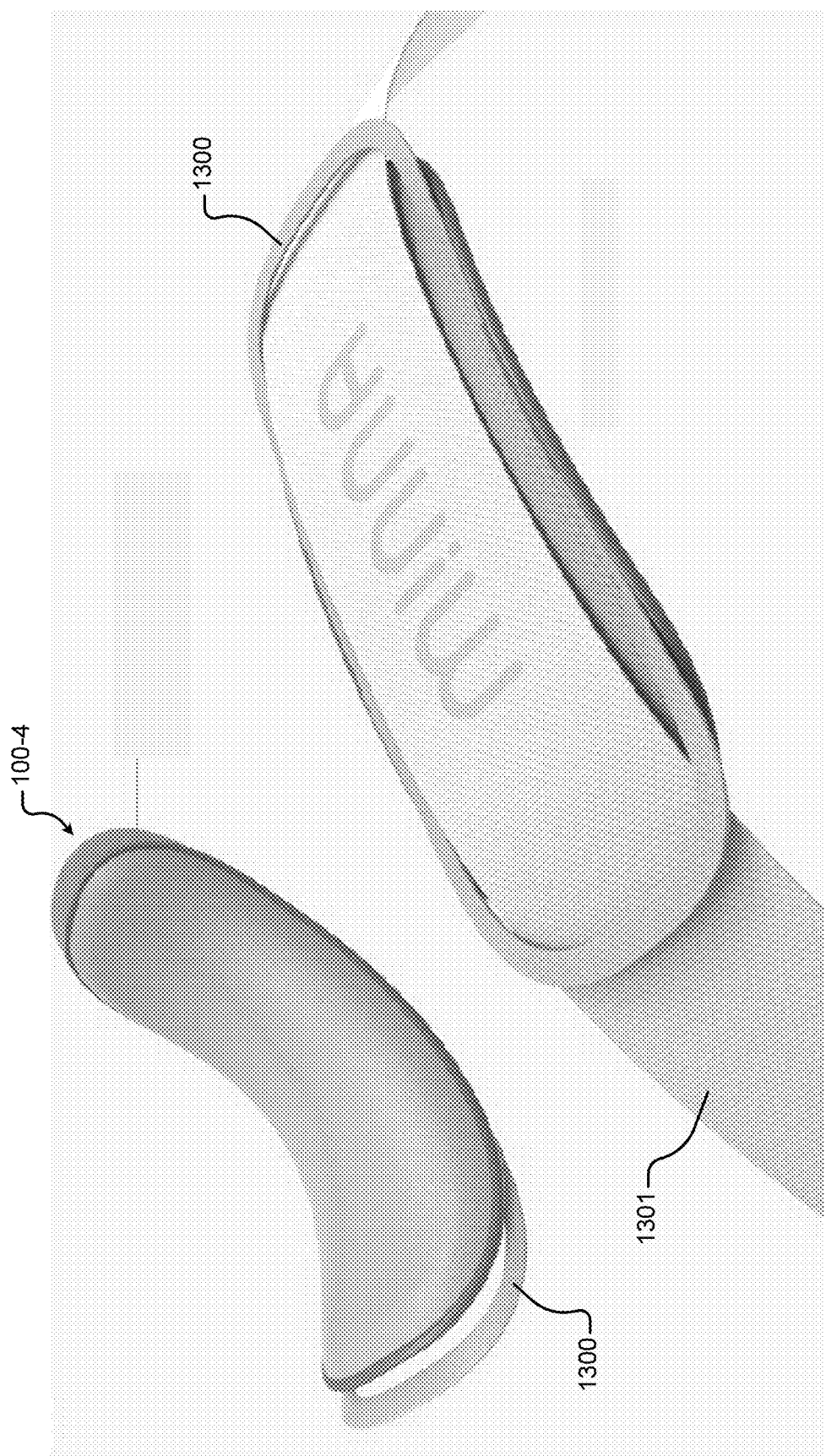
Figure 13B:
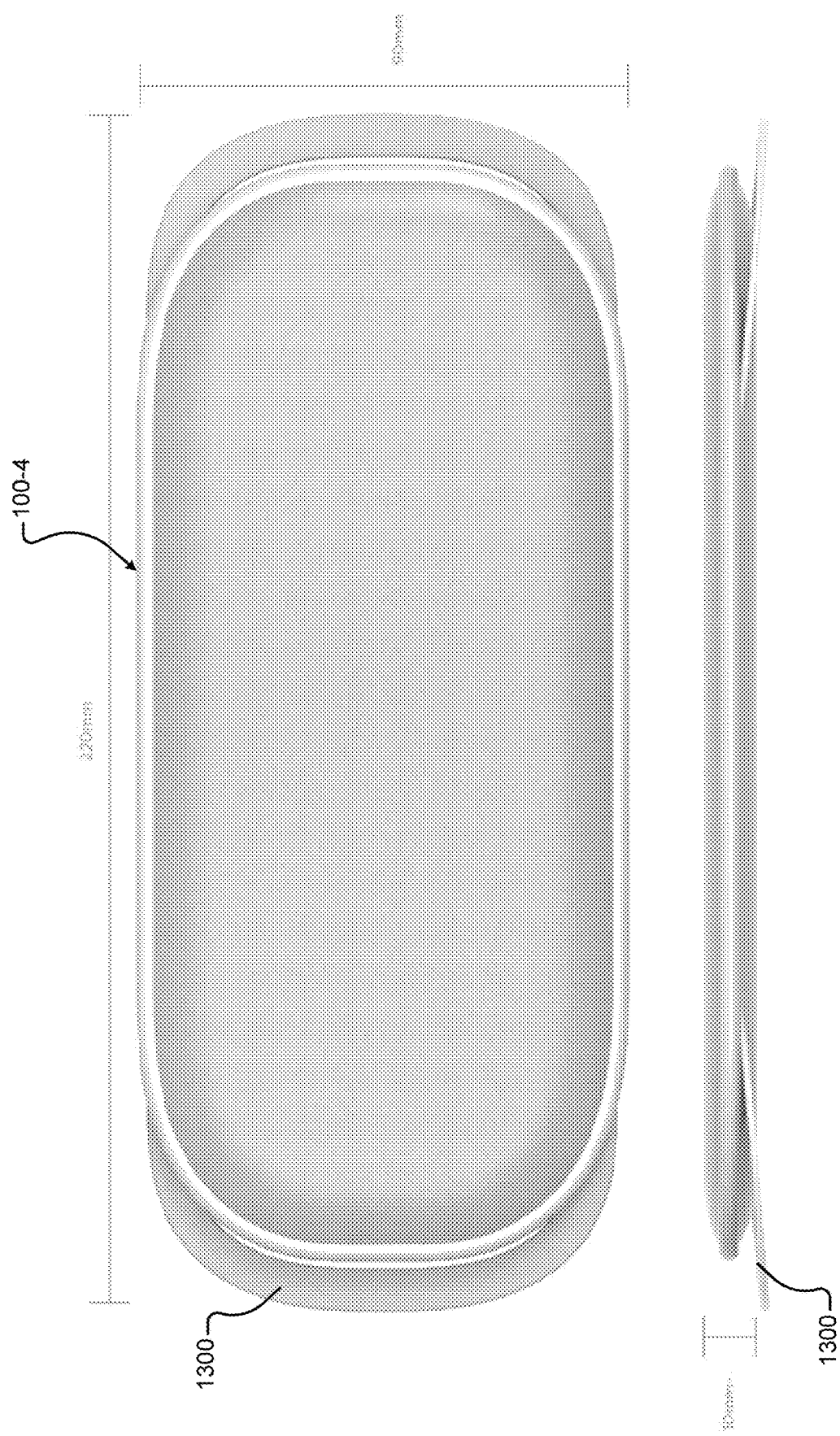

FIGS. 13A-13D illustrate a fourth heating device 100-4. The fourth heating device package can include one or more heating elements 204 arranged in any manner throughout the package. The fourth heating device 100-4 can be applied to different parts of the user's body (e.g., see FIG. 13D). The fourth device package can include one or more belt loops 1300 for receiving a belt 1301. The belt loops 1300 of the fourth device package, which are located at the edges of the fourth device package, may be integrated with the encapsulation top cover 1302. The fourth heating device 100-4 can include a user input button 106 (e.g., an on/off button) and a power input port. In FIG. 13B, the fourth heating device 100-4 may have approximate dimensions of 220 mm by 90 mm, with a thickness of approximately 10 mm.

Figure 13C:
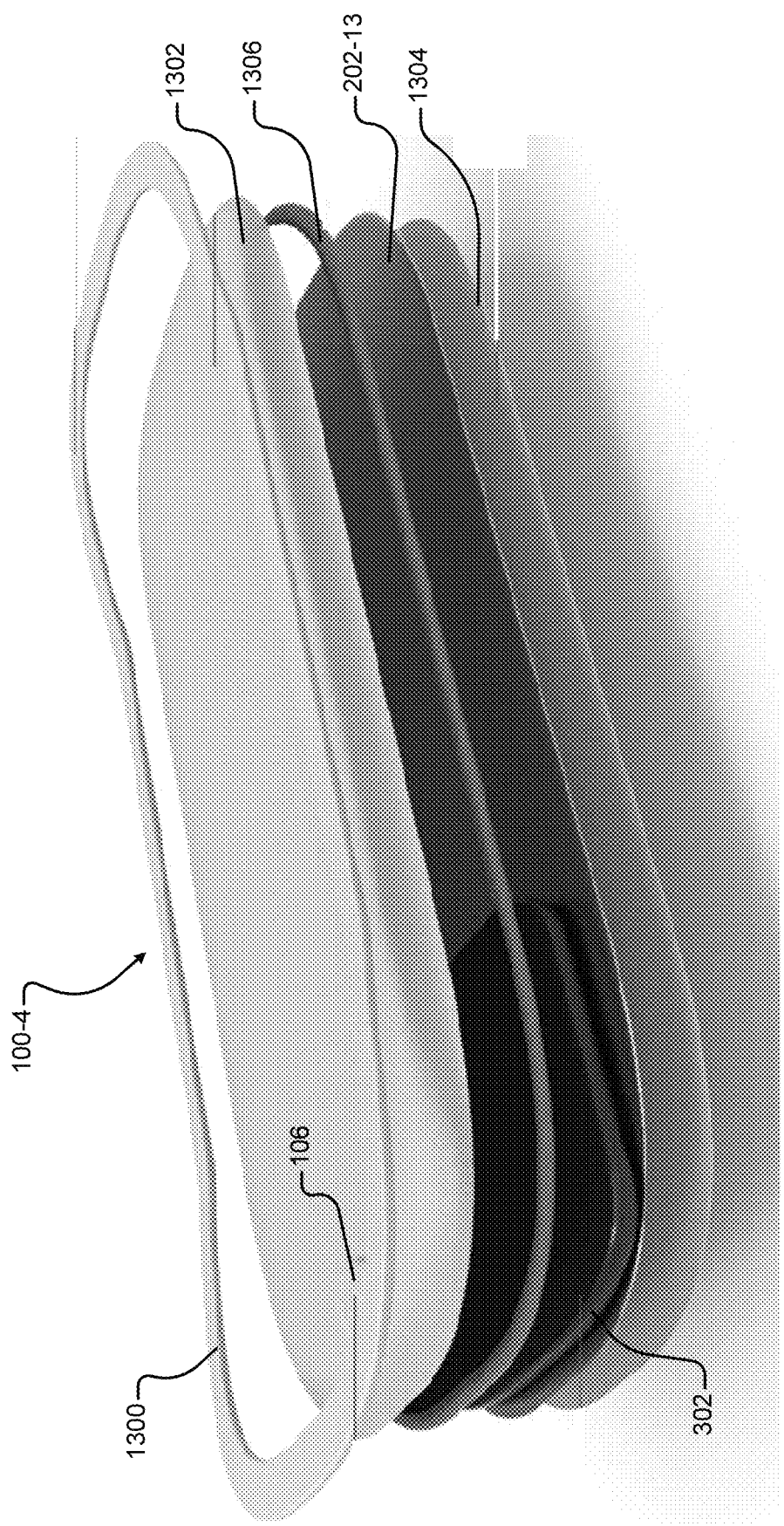
Figure 13D:

Referring to FIG. 13C, the fourth heating device 100-4 may include similar layers as the first heating device 100-1, such as the encapsulation layers 1302, 1304 and the heating unit 202-13. The fourth heating device 100-4 also includes a shape retention element 1306 (e.g., a moldable wire or plastically deformable material) that the user can use to form the fourth heating device 100-4 into a shape that is maintained by the shape retention element 1306. The shape retention element 1306 may be used to shape and fix the fourth heating device 100-4 to the user's body (e.g., around the shoulder in FIG. 13D, waist, arm, hand, leg, foot, neck, or head). For example, the shape retention element 1306 (e.g., the wire) may be pressed to conform to the user's body and maintain its shape so that the heating device 100-4 conforms to the user's body when the user removes their hand from the heating device 100-4. Since the belt loops 1300 are integrated into the perimeter of the fourth heating device 100-4, the belt loops 1300 may also conform to whatever shape the fourth heating device 100-4 takes. Although the shape retention element 1306 is included around the perimeter of the fourth heating device 100-4, a heating device may include shape retention elements along one or more axes of the heating device.

Figure 14A:
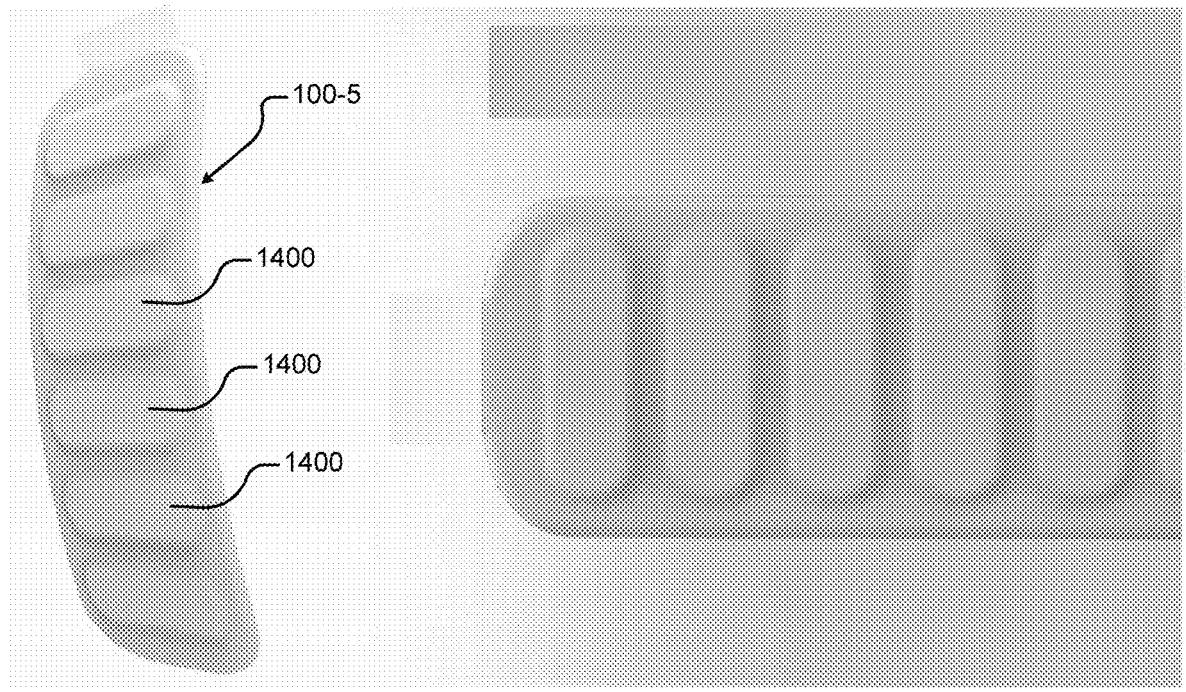
Figure 14B:
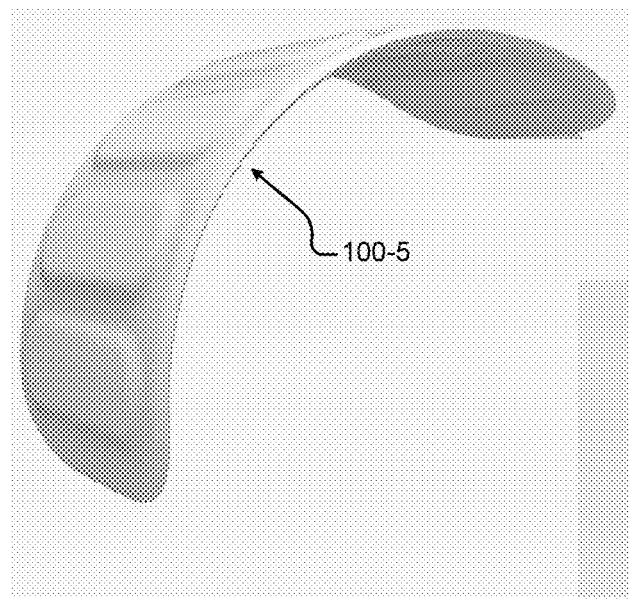
Figure 14C:

FIGS. 14A-14C illustrate a fifth heating device 100-5 having a fifth device package. The fifth device package separates different components into different pods 1400. The pods 1400 may include different components. In some examples, one or more pods 1400 may include the battery and device electronics. In these examples, the remaining pods may include heating units. In some implementations, the heating units may be distributed throughout the full surface of the heating device 100-5 or beneath some or all of the pods 1400. The fifth heating device 100-5 may include similar layers as the other heating devices, such as encapsulation layers, heating units, and an adhesive layer. Separation of the components into different pods 1400 may allow the heating device 100-5 to easily fold/roll in one direction. The flexibility of the fifth heating device 100-5 may help it conform to the user's body (e.g., a user's shoulder) as illustrated in FIG. 14C.

Figure 15:
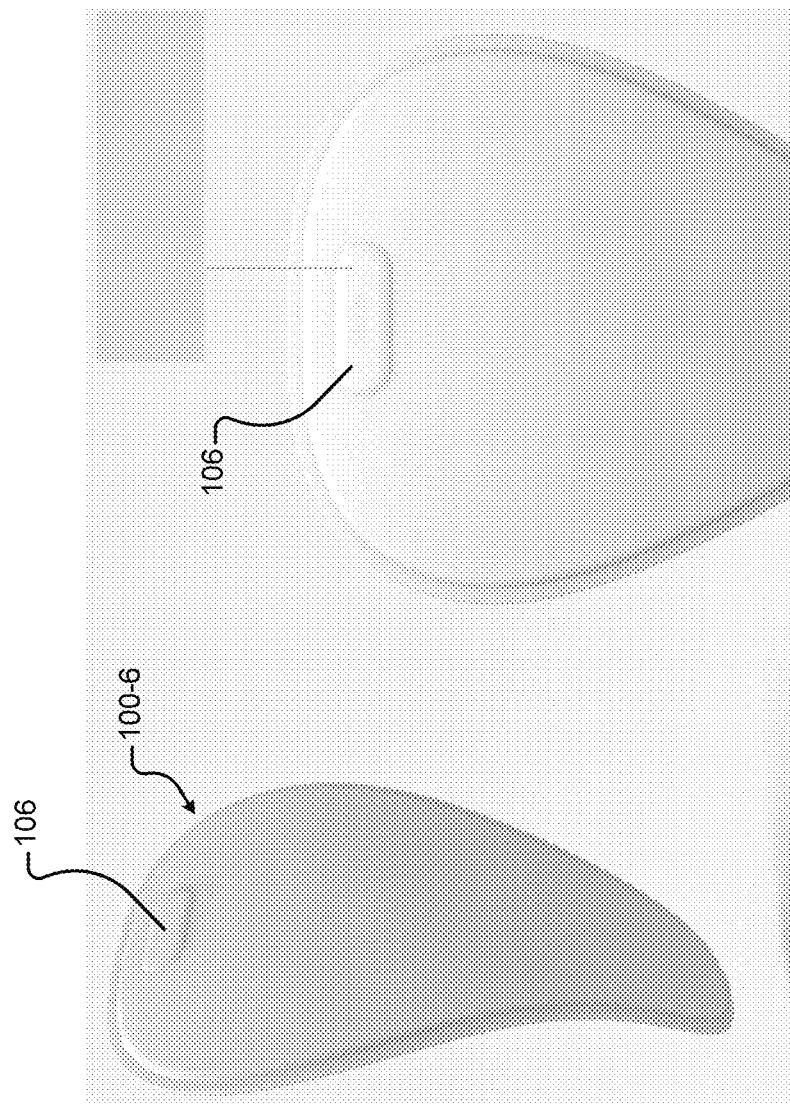

FIG. 15 illustrates a sixth heating device 100-6 having a sixth device package. The sixth heating device 100-6 is shaped to conform to a female's pelvic region. The sixth heating device 100-6 may include similar layers and components as the other heating devices, such as user input buttons, device electronics, a battery, encapsulation layers, heating units, and an adhesive layer. The sixth heating device 100-6 may be flexible so that it conforms to the user's body. In some implementations, the sixth heating device 100-6 (or any other heating device) may be made from water repellant materials.

Figure 16A:
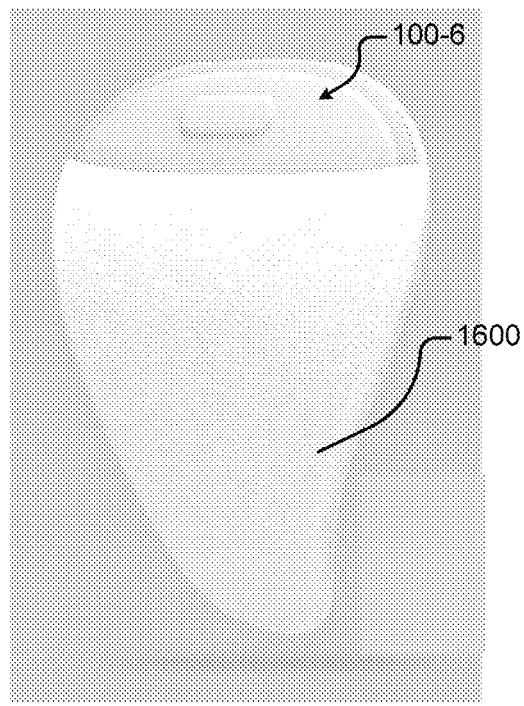
Figure 16B:
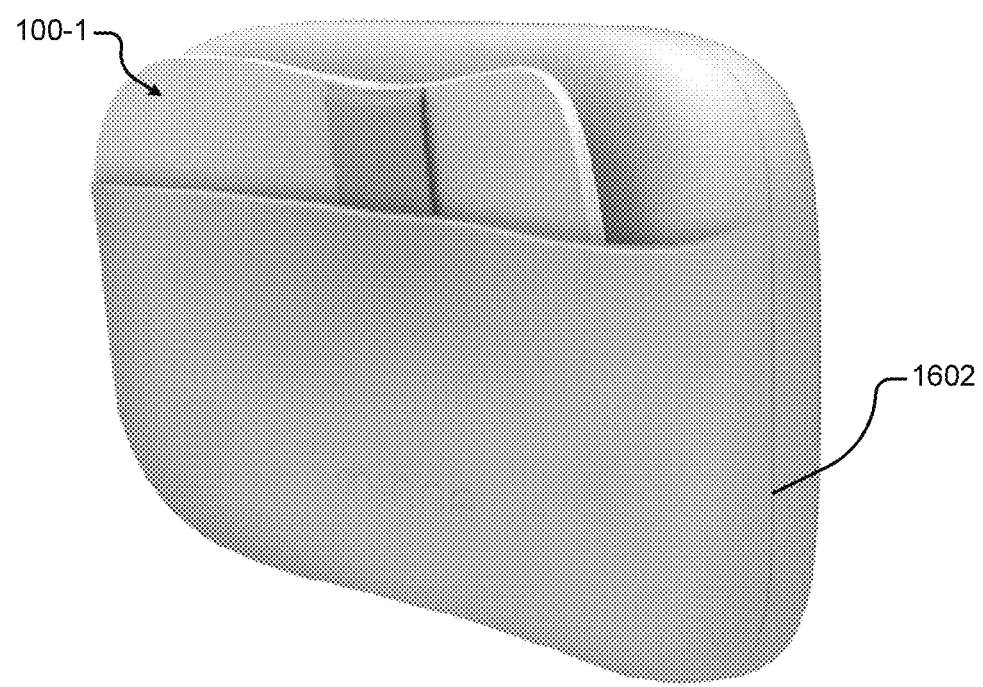

FIGS. 16A-16E illustrate various sleeves and garments that may be configured to hold the heating devices 100 described herein. FIG. 16A illustrates an example sleeve 1600 that holds the sixth heating device 100-6. The sleeve 1600 of FIG. 16A may be fabricated from a cloth material (e.g., cotton or other fabric). In some implementations, the sleeve 1600 may be fabricated from a material that spreads heat. In some implementations, the sleeve 1600 may be fabricated from a breathable material. FIG. 16B illustrates another sleeve 1602. The sleeve 1602 of FIG. 16B is a weighted sleeve configured to hold the first heating device 100-1. The weighted sleeve 1602 may apply pressure to the heating device 100-1 during use (e.g., while resting on the user).

Figure 16D:
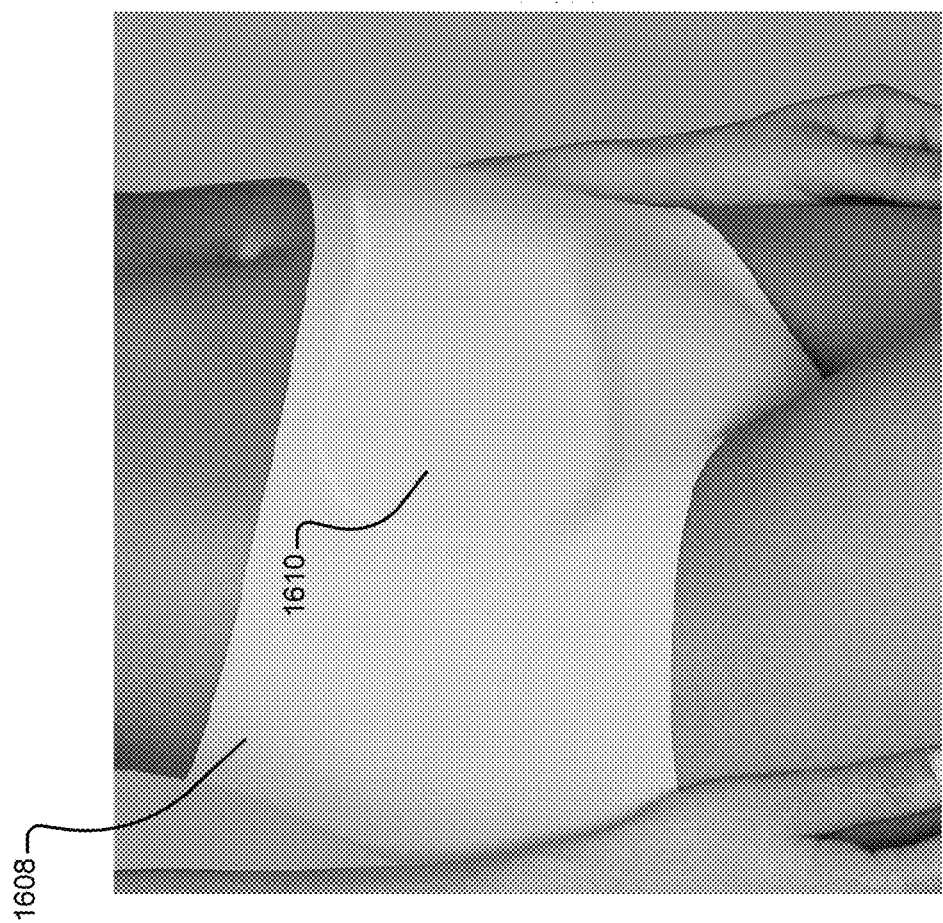
Figure 16C:
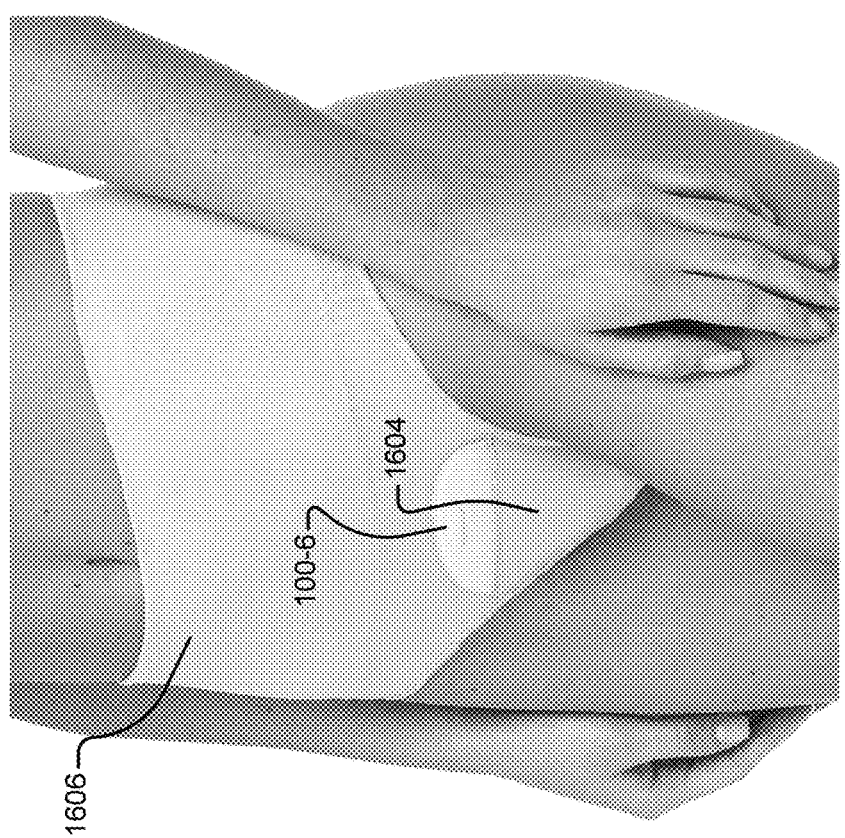

FIGS. 16C-16E illustrate garments that are configured to hold the heating devices 100. FIG. 16C is a female underwear garment 1606 including a device pouch 1604 that is shaped to hold the sixth heating device 100-6 in the pelvic region. FIG. 16D is another underwear garment 1608 including a device pouch 1610 for holding a heating device. Specifically, the garment 1608 of FIG. 16D includes a device pouch 1610 that holds the first heating device 100-1 above the pubic region. FIG. 16E illustrates an additional example underwear garment 1612 for a woman that includes a device pouch 1614 for holding the first heating device 100-1 in the user's lower back.

Various examples have been described. These and other examples are within the scope of the following claims.

What is claimed is:

1. A heating device comprising:
   a heating unit configured to deliver heat to a user's body, the heating unit comprising:
      a substrate; and
      a plurality of heating elements supported by the substrate;
   device electronics coupled to the heating elements, the device electronics configured to:
      wirelessly receive one or more heating profiles from an external computing device, wherein each of the heating profiles includes data indicating how power should be delivered to the heating elements over time; and
      deliver power to the heating elements according to the one or more heating profiles; and
   a device package comprising:
      the heating unit;
      the device electronics;
      a battery that provides power to the device electronics, wherein the device electronics and the battery are centrally located between the plurality of heating elements; and
      a belt configured to wrap around the user's body.

2. The heating device of claim 1, further comprising one or more belt loops attached to the device package, wherein the belt is configured to be inserted through the one or more belt loops and wrapped around the user's body.

3. The heating device of claim 1, wherein the device package encapsulates the heating unit and is configured to interface with the user's body such that the heating elements provide heat to the user's body via a portion of the device package that interfaces with the user's body, and wherein the device package includes a shape retention element configured to conform to the user's body under pressure applied by the user and maintain the shape of the device package after the pressure is removed.

4. The heating device of claim 1, further comprising a user input device configured to receive user input, wherein the user input device communicates with the device electronics, and wherein the device electronics are configured to modify the delivery of power to the heating elements in response to user input received by the user input device.

5. The heating device of claim 1, wherein the device electronics are configured to:
  wirelessly receive user-input instructions from the external computing device indicating how to modify the delivery of power to the heating elements according to user input received at the external computing device; and
  modify the delivery of power to the heating elements based on the received user-input instructions.

6. The heating device of claim 1, wherein the heating device further comprises a heating unit connector that is configured to:
  electrically couple the heating unit to the device electronics; and
  decouple the heating unit from the device electronics.

7. The heating device of claim 1, further comprising a plurality of temperature sensors, wherein each temperature sensor is located in proximity to a corresponding heating element, wherein each temperature sensor generates a temperature signal indicating the temperature in proximity to the temperature sensor, and wherein the device electronics are configured to deliver power to the heating elements based on one or more of the temperature signals.

8. The heating device of claim 1, wherein the battery is a removable battery.

9. The heating device of claim 1, further comprising a power input port configured to connect to an external power source, wherein the device electronics are configured to charge the battery when the external power source is connected to the power input port.

10. The heating device of claim 1, wherein the device electronics are configured to:
  wirelessly receive a power-off instruction from the external computing device;
  power off the heating device in response to the power-off instruction;
  wirelessly receive a power-on instruction from the external computing device; and
  power on the heating device in response to the power-on instruction.

11. The heating device of claim 1, wherein the belt is attached to the device package.

12. The heating device of claim 11, wherein the device package includes device package connectors, wherein the belt includes belt connectors that are configured to connect and disconnect from the device package connectors, and wherein the belt is removed from the device package when the belt connectors are disconnected from the device package connectors.

13. The heating device of claim 1, wherein the substrate is a flexible substrate, wherein the heating device further comprises a rigid housing that houses the battery and the device electronics, and wherein the rigid housing is attached to the substrate and centrally located between the plurality of heating elements.

14. The heating device of claim 13, wherein the battery is a removable battery, and wherein the rigid housing includes a battery receptacle configured to receive the removable battery.

15. The heating device of claim 1, further comprising one or more pieces of insulating foam padding that cover the heating elements on a side of the substrate that is opposite to a side of the substrate that delivers heat to the user's body.

16. A heating device comprising:
  a first heating element configured to deliver heat to a first portion of a user's body;
  a second heating element configured to deliver heat to a second portion of the user's body;
  one or more substrates that support the first and second heating elements;
  device electronics coupled to the first and second heating elements, the device electronics configured to:
    wirelessly communicate with an external computing device;
    wirelessly receive user-input instructions from the external computing device, the user-input instructions indicating an amount of power to deliver to each of the first and second heating elements; and
    deliver power to the first and second heating elements based on the user-input instructions; and
  a device package comprising:
    the first and second heating elements;
    the one or more substrates;
    the device electronics;
    a battery that provides power to the device electronics, wherein the device electronics and the battery are centrally located between the first and second heating elements; and
    a belt configured to wrap around the user's body.

17. The heating device of claim 16, further comprising one or more belt loops attached to the device package, wherein the belt is configured to be inserted through the one or more belt loops and wrapped around the user's body.

18. The heating device of claim 16, wherein the device package encapsulates the first and second heating elements and the one or more substrates, wherein the device package is configured to interface with the user's body such that the first and second heating elements provide heat to the user's body via a portion of the device package that interfaces with the user's body, and wherein the device package includes a shape retention element configured to conform to the user's body under pressure applied by the user and maintain the shape of the device package after the pressure is removed.

19. The heating device of claim 16, further comprising a user input device configured to receive user input, wherein the user input device communicates with the device electronics, and wherein the device electronics are configured to modify the delivery of power to the first and second heating elements in response to the user input received by the user input device.

20. The heating device of claim 16, wherein the device electronics are configured to:
  wirelessly receive a heating profile from the external computing device, wherein the heating profile includes data indicating how power should be delivered to the first and second heating elements over a period of time; and
  deliver power to the first and second heating elements according to the heating profile.

21. The heating device of claim 16, wherein the one or more substrates and the first and second heating elements comprise a heating unit, and wherein the heating device further comprises a heating unit connector that is configured to:

electrically couple the heating unit to the device electronics; and decouple the heating unit from the device electronics.

22. The heating device of claim 16, further comprising a plurality of temperature sensors, wherein each temperature sensor is located in proximity to a corresponding heating element, wherein each temperature sensor generates a temperature signal indicating the temperature in proximity to the temperature sensor, and wherein the device electronics are configured to deliver power to the first and second heating elements based on the one or more temperature signals.

23. The heating device of claim 16, wherein the battery is a removable battery.

24. The heating device of claim 16, further comprising a power input port configured to connect to an external power source, wherein the device electronics are configured to charge the battery when the external power source is connected to the power input port.

25. The heating device of claim 16, wherein the device electronics are configured to:

wirelessly receive a power-off instruction from the external computing device;

power off the heating device in response to the power-off instruction;

wirelessly receive a power-on instruction from the external computing device; and power on the heating device in response to the power-on instruction.

26. The heating device of claim 16, wherein the belt is attached to the device package.

27. The heating device of claim 26, wherein the device package includes device package connectors, wherein the belt includes belt connectors that are configured to connect and disconnect from the device package connectors, and wherein the belt is removed from the device package when the belt connectors are disconnected from the device package connectors.

28. The heating device of claim 16, wherein the one or more substrates are flexible substrates, wherein the heating device further comprises a rigid housing that houses the battery and the device electronics, and wherein the rigid housing is attached to the one or more flexible substrates and centrally located between the first and second heating elements.

29. The heating device of claim 28, wherein the battery is a removable battery, and wherein the rigid housing includes a battery receptacle configured to receive the removable battery.

30. The heating device of claim 16, further comprising one or more pieces of insulating foam padding that cover the first and second heating elements on sides of the one or more substrates that are opposite to sides of the one or more substrates that deliver heat to the user's body.

* * * * *